United States Patent
De Man et al.

(10) Patent No.: US 11,053,230 B2
(45) Date of Patent: Jul. 6, 2021

(54) 3-HYDROXY-IMIDAZOLIDIN-4-ONE COMPOUNDS AS INHIBITORS OF INDOLEAMINE 2,3-DIOXYGENASE

(71) Applicant: Netherlands Translational Research Center B.V., Oss (NL)

(72) Inventors: Adrianus Petrus Antonius De Man, Oss (NL); Joost Cornelis Marinus Uitdehaag, Oss (NL); Jan Gerard Sterrenburg, Oss (NL); Joeri Johannes Petrus De Wit, Oss (NL); Freek Van Cauter, Oss (NL); Nicole Wilhelmina Cornelia Seegers, Oss (NL); Antonius Maria Van Doornmalen, Oss (NL); Rogier Christian Buijsman, Oss (NL); Guido Jenny Rudolf Zaman, Oss (NL)

(73) Assignee: Netherlands Translational Research Center B.V.

( * ) Notice: Subject to any disclaimer, the term of this patent is extended or adjusted under 35 U.S.C. 154(b) by 0 days.

(21) Appl. No.: 16/642,756

(22) PCT Filed: Aug. 30, 2018

(86) PCT No.: PCT/EP2018/073357
§ 371 (c)(1),
(2) Date: Feb. 27, 2020

(87) PCT Pub. No.: WO2019/043103
PCT Pub. Date: Mar. 7, 2019

(65) Prior Publication Data
US 2020/0181128 A1     Jun. 11, 2020

(30) Foreign Application Priority Data
Sep. 1, 2017 (EP) ..................... 17189105

(51) Int. Cl.
| | | |
|---|---|---|
| *C07D 409/04* | (2006.01) | |
| *C07D 409/14* | (2006.01) | |
| *C07D 417/04* | (2006.01) | |
| *C07F 5/02* | (2006.01) | |

(52) U.S. Cl.
CPC ......... *C07D 409/04* (2013.01); *C07D 409/14* (2013.01); *C07D 417/04* (2013.01); *C07F 5/025* (2013.01)

(58) Field of Classification Search
CPC .................................................. C07D 409/04
See application file for complete search history.

(56) References Cited

U.S. PATENT DOCUMENTS 10,494,360 B2 * 12/2019 De Man ................ A61P 33/00

FOREIGN PATENT DOCUMENTS

| WO | WO9929310 A2 | 6/1999 |
|---|---|---|
| WO | WO2005111001 A1 | 11/2005 |
| WO | WO2006115188 A1 | 11/2006 |
| WO | WO2008036642 A2 | 3/2008 |
| WO | WO2008058178 A1 | 5/2008 |
| WO | WO2011056652 A1 | 5/2011 |
| WO | WO2012160464 A1 | 11/2012 |
| WO | WO2015150097 A1 | 10/2015 |
| WO | WO2015173764 A1 | 11/2015 |
| WO | WO2015188085 A1 | 12/2015 |
| WO | WO2017153459 A1 | 9/2017 |

OTHER PUBLICATIONS

Röhrig, Ute F., et al. "Challenges in the discovery of indoleamine 2, 3-dioxygenase 1 (IDO1) inhibitors." Journal of Medicinal Chemistry 58.24 (2015): 9421-9437.
Yue, Eddy W., et al. "Discovery of potent competitive inhibitors of indoleamine 2, 3-dioxygenase with in vivo pharmacodynamic activity and efficacy in a mouse melanoma model." Journal of Medicinal Chemistry 52.23 (2009): 7364-7367.
Dolušić, Eduard et al. "Indoleamine 2, 3-dioxygenase inhibitors: a patent review (2008-2012)." Expert Opinion on Therapeutic Patents 23.10 (2013): 1367-1381.
Shon, Woo-Leong, et al. "Severity of DSS-induced colitis is reduced in Ido1-deficient mice with down-regulation of TLR-MyD88-NF-kB transcriptional networks." Scientific Reports 5 (2015): 17305. (12 pages).
Park, Wooram, et al. "Advances in the synthesis and application of nanoparticles for drug delivery." Wiley Interdisciplinary Reviews: Nanomedicine and Nanobiotechnology 7.4 (2015): 494-508.
International Search Report and Written Opinion for International Application No. PCT/EP2018/073357; dated Oct. 1, 2018 (10 pages).

(Continued)

*Primary Examiner* — Golam M Shameem
(74) *Attorney, Agent, or Firm* — Mendelsohn Dunleavy, P.C.

(57) ABSTRACT

The invention relates to a compound of Formula (I): Formula (I), or pharmaceutically acceptable enantiomers, or salts thereof. The present invention also relates to the use of compounds of Formula (I) as selective inhibitors of indoleamine 2,3-dioxygenase. The invention also relates to the use of the compounds of Formula (I) for the treatment or prevention of diseases cancer, infections, central nervous system disease or disorder, and immune-related disorders, either as a single agent or in combination with other therapies.

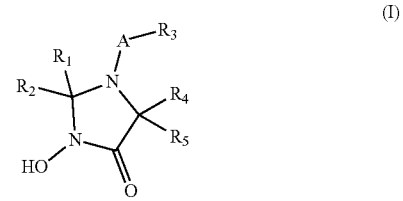

17 Claims, No Drawings

(56) References Cited

OTHER PUBLICATIONS

Ou, Xueling, et al. "Enhancement of dendritic cell-tumor fusion vaccine potency by indoleamine-pyrrole 2, 3-dioxygenase inhibitor, 1-MT" Journal of Cancer Research and Clinical Oncology 134.5 (2008): 525-533.

Seegers, Nicole, et al. "High-throughput fluorescence-based screening assays for tryptophan-catabolizing enzymes." Journal of Biomolecular Screening 19.9 (2014): 1266-1274.

Théate, Ivan, et al. "Extensive profiling of the expression of the indoleamine 2, 3-dioxygenase 1 protein in normal and tumoral human tissues." Cancer Immunology Research 3.2 (2015): 161-172.

Kristeleit, Rebecca, et al. "A randomised, open-label, phase 2 study of the IDO1 inhibitor epacadostat (INCB024360) versus tamoxifen as therapy for biochemically recurrent (CA-125 relapse)—only epithelial ovarian cancer, primary peritoneal carcinoma, or fallopian tube cancer." Gynecologic Oncology 146.3 (2017): 484-490.

Bluthe, R. M., et al. "Synergy between tumor necrosis factor α and interleukin-1 in the induction of sickness behavior in mice." Psychoneuroendocrinology 19.2 (1994): 197-207.

Reyes, Melvyn P., et al. "Quinolinic Acid Concentrations in Brain and Cerebrospinal Fluid of Patients with Intractable Complex Partial Seizures." Epilepsia 31.2 (1990): 172-177.

Saito, Kuniaki, et al. "Mechanism of Delayed Increases in Kynurenine Pathway Metabolism in Damaged Brain Regions Following Transient Cerebral Ischemia." Journal of Neurochemistry 60.1 (1993): 180-192.

Koblish, Holly K., et al. "Hydroxyamidine Inhibitors of Indoleamine-2, 3-dioxygenase Potently Suppress Systemic Tryptophan Catabolism and the Growth of IDO-expressing Tumors." Molecular Cancer Therapeutics 9.2 (2010): 489-498.

Matin, Azadeh, et al. "A fluorescence-based assay for indoleamine 2, 3-dioxygenase." Analytical Biochemistry 349.1 (2006): 96-102.

Yoshida, Ryotaro, et al. "Induction of indoleamine 2, 3-dioxygenase in mouse lung during virus infection." Proceedings of the National Academy of Sciences 76.8 (1979): 4084-4086.

Badland, Matthew, et al. "Thiophene and bioisostere derivatives as new MMP12 inhibitors." Bioorganic & Medicinal Chemistry Letters 21.1 (2011): 528-530.

Takikawa, Osamu, et al. "Mechanism of interferon-gamma action. Characterization of indoleamine 2, 3-dioxygenase in cultured human cells induced by interferon-gamma and evaluation of the enzyme-mediated tryptophan degradation in its anticellular activity." Journal of Biological Chemistry 263.4 (1988): 2041-2048.

Heyes, Melvyn P., et al. "Sources of the neurotoxin quinolinic acid in the brain of HIV-1-infected patients and retrovirus-infected macaques." The FASEB Journal 12.10 (1998): 881-896.

Yue, Eddy W., et al. "INCB24360 (Epacadostat), a Highly Potent and Selective Indoleamine-2, 3-dioxygenase 1 (IDO1) Inhibitor for Immuno-oncology." ACS Medicinal Chemistry Letters 8.5 (2017): 486-491.

Issa, Fuad, et al. "A Multidimensional Approach to Analysis of Cerebrospinal Fluid Biogenic Amines in Schizophrenia: II. Correlations with Psychopathology." Psychiatry Research 52.3 (1994): 251-258.

Ino, K., et al. "Indoleamine 2, 3-dioxygenase is a novel prognostic indicator for endometrial Cancer." British Journal of Cancer 95.11 (2006): 1555-1561.

Lu, Changyuan et al. "Inhibitory Substrate Binding Site of Human Indoleamine 2, 3-Dioxygenase." Journal of the American Chemical Society 131.36 (2009): 12866-12867.

Wainwright, Derek A., et al. "Durable Therapeutic Efficacy Utilizing Combinatorial Blockade Against IDO, CTLA-4, and PD-L1 in Mice with Brain Tumors." Clinical Cancer Research 20.20 (2014): 5290-5301.

Andre, Caroline, et al. "Diet-induced obesity progressively alters cognition, anxiety-like behavior and lipopolysaccharide-induced depressive-like behavior: focus on brain indoleamine 2, 3-dioxygenase activation." Brain, Behavior, and Immunity 41 (2014): 10-21.

Moroni, Flavio, et al. "The excitotoxin quinolinic acid is present in the brain of several mammals and its cortical content increases during the aging process." Neuroscience Letters 47.1 (1984): 51-55.

Devita, Vincent T. et al. "Cancer: Principles and Practice of Oncology" 6th edition, 2001, Lippincott Williams & Wilkins Publishers (2374 pages).

Favennec, Marie, et al. "The Kynurenine Pathway is Activated in Human Obesity and Shifted Toward Kynurenine Monooxygenase Activation." Obesity 23.10 (2015): 2066-2074.

Munn, David H., et al. "Selective Activation-Induced Apoptosis of Peripheral T Cells Imposed by Macrophages. A Potential Mechanism of Antigen-Specific Peripheral Lymphocyte Deletion." The Journal of Immunology 156.2 (1996): 523-532.

Vécsei' László, et al. "Kynurenines in the CNS: recent advances and new questions." Nature Reviews Drug Discovery 12.1 (2013): 64-82.

Makala, Levi HC, et al. "Leishmania major Attenuates Host Immunity by Stimulating Local Indoleamine 2, 3-Dioxygenase Expression." Journal of Infectious Diseases 203.5 (2011): 715-725.

Bonaccorso, Stefania, et al. "Depression induced by treatment with interferon-alpha in patients affected by hepatitis C virus." Journal of Affective Disorders 72.3 (2002): 237-241.

Reynolds, G. P. et al., "Increased Brain 3-hydroxykynurenine in Huntington's disease." Lancet (London, England) vol. 2 (1989): 979-980.

Uyttenhove, Catherine, et al. "Evidence for a tumoral immune resistance mechanism based on tryptophan degradation by indoleamine 2, 3-dioxygenase." Nature Medicine 9.10 (2003): 1269-1274.

Beatty, Gregory L., et al. "First-in-Human Phase I Study of the Oral Inhibitor of Indoleamine 2, 3-Dioxygenase-1 Epacadostat (INCB024360) in Patients with Advanced Solid Malignancies." Clinical Cancer Research 23.13 (2017): 3269-3276.

Fox, J. M., et al. "Inhibition of indoleamine 2, 3-dioxygenase enhances the T-cell response to influenza virus infection." The Journal of General Virology 94.Pt 7 (2013): 1451-1461.

Klockow, Jessica L. et al. "Development of a Fluorescent Chemosensor for the Detection of Kynurenine." Organic Letters 15.2 (2013): 235-237.

Maes, Michael, et al. "Relationships Between Lower Plasma L-Tryptophan Levels and Immune-Inflammatory Variables in Depression." Psychiatry Research 49.2 (1993): 151-165.

Schutz, Gunther, et al. "Purification and Properties of Rat Liver Tryptophan Oxygenase." Journal of Biological Chemistry 247.17 (1972): 5327-5332.

Heyes, Melvyn P., et al. "Quinolinic acid in tumors, hemorrhage and bacterial infections of the central nervous system in children." Journal of the Neurological Sciences 133.1 (1995): 112-118.

Munn, David H., et al. "Prevention of Allogeneic Fetal Rejection by Tryptophan Catabolism." Science 281.5380 (1998): 1191-1193.

Berge, Stephen M. et al. "Pharmaceutical Salts." Journal of Pharmaceutical Sciences 66.1 (1977): 1-19.

Reynolds, Gavin P., et al. "Brain Quinolinic Acid in Huntington's Disease." Journal of Neurochemistry 50.6 (1988): 1959-1960.

Kazda, Hana, et al. "Maternal, Umbilical, and Amniotic Fluid Concentrations of Tryptophan and Kynurenine after Labor or Cesarean Section." Pediatric Research 44.3 (1998): 368-373.

Orlikov, Alexie B. et al. "Kynurenine in Blood Plasma and DST in Patients with Endogenous Anxiety and Endogenous Depression." Biological Psychiatry 36.2 (1994): 97-102.

Cady, Susan G. et al. "1-Methyl-dl-tryptophan, β-(3-Benzofuranyl)-dl-alanine (the Oxygen Analog of Tryptophan), and β-[3-Benzo(b)thienyl]-DL-alanine (the Sulfur Analog of Tryptophan) Are Competitive Inhibitors for Indoleamine 2, 3-Dioxygenase." Archives of Biochemistry and Biophysics 291.2 (1991): 326-333.

Bonaccorso S., et al. "Increased Depressive Ratings in Patients With Hepatitis C Receiving Interferon-alpha-Based Immunotherapy Are Related to Interferon-alpha-Induced Changes in the Serotonergic System." Journal Clinical Psychopharmacology 22.1 (2002): 86-90.

Brandacher, Gerald, et al. "Prognostic Value of Indoleamine 2, 3-Dioxygenase Expression in Colorectal Cancer: Effect on Tumor-Infiltrating T cells." Clinical Cancer Research 12.4 (2006): 1144-1151.

(56) References Cited

OTHER PUBLICATIONS

March, J. "Advanced Organic Chemistry: Reactions, Mechanisms, and Structure." John Wiley & Sons, 2007 (2374 pages).

Zeng, Jun, et al. "Prevention of Spontaneous Tumor Development in a ret Transgenic Mouse Model by Ret Peptide Vaccination with Indoleamine 2, 3-Dioxygenase Inhibitor 1-Methyl Tryptophan." Cancer Research 69.9 (2009): 3963-3970.

Holmgaard, Rikke B., et al. "Indoleamine 2, 3-dioxygenase is a critical resistance mechanism in antitumor T cell immunotherapy targeting CTLA-4." Journal of Experimental Medicine 210.7 (2013): 1389-1402.

Muller, Alexander J., et al. "Inhibition of indoleamine 2, 3-dioxygenase, an immunoregulatory target of the cancer suppression gene Bin1, potentiates cancer chemotherapy." Nature Medicine 11.3 (2005): 312-319.

Lee, Alexander, et al. "IDO1 and IDO2 Non-Synonymous Gene Variants: Correlation with Crohn's Disease Risk and Clinical Phenotype" PLoS One 9.12 (2014): e115848, 15 pages.

Bianchi, Mauro, et al. "Central effects of tumor necrosis factor α and interleukin-1α on nociceptive thresholds and spontaneous locomotor activity." Neuroscience Letters 148.1-2 (1992): 76-80.

Sinz, Elizabeth H., et al. "Quinolinic Acid Is Increased in CSF and Associated With Mortality After Traumatic Brain Injury in Humans." Journal of Cerebral Blood Flow & Metabolism 18.6 (1998): 610-615.

Sanni, Latifu A., et al. "Dramatic changes in oxidative tryptophan metabolism along the kynurenine pathway in experimental cerebral and noncerebral malaria." The American Journal of Pathology 152.2 (1998): 611-619.

Gould, Philip L "Salt selection for basic drugs." International Journal of Pharmaceutics 33.1-3 (1986): 201-217.

Greene, Theodora W. et al. "Protective Groups in Organic Synthesis", Third Edition. (1999) John Wiley & Sons, Inc. 1-799.

\* cited by examiner

3-HYDROXY-IMIDAZOLIDIN-4-ONE COMPOUNDS AS INHIBITORS OF INDOLEAMINE 2,3-DIOXYGENASE

The present invention relates to 3-hydroxyimidazolidin-4-one derivatives, to pharmaceutical compositions comprising these compounds and their use in therapy. In particular, the present invention relates to the use of 3-hydroxyimidazolidin-4-one derivatives for the treatment and/or prevention of cancer, infections, central nervous system disease or disorders, and immune-related disorders.

The present invention relates to 3-hydroxyimidazolidin-4-one compounds which modulate the activity of indoleamine 2,3-dioxygenase, in particular inhibit the activity of indoleamine 2,3-dioxygenase. Indoleamine 2,3-dioxygenase (IDO1, EC 1.13.11.52) is an oxidoreductase that catalyzes the first and rate-limiting step of the kynurenine pathway of L-tryptophan degradation. L-tryptophan is an essential amino acid required for the synthesis of proteins and the production of the neurotransmitter 5-hydroxy tryptamine (serotonin) and niacin (vitamin B3). Both L-tryptophan and L-tryptophan metabolites formed along the kynurenine pathway are regulators of the local immune response. IDO1 plays an important role in immune tolerance. Studies of mammalian pregnancy have indicated that IDO1 expressed in the placenta protects the fetus against the maternal immune response, thus preventing fetal rejection in utero (Munn, D. H., et al., Science 281: 1191; 1998). Tumor cells expressing IDO1 create a similar state of immune tolerance (Uyttenhove, C., et al., Nat. Med. 9: 1269; 2003). IDO1 expressed in mouse tumor cells prevented their rejection by pre-immunized mice and this effect could be reverted by 1-methyl-L-tryptophan (1-MT), a low-potency inhibitor of IDO1 (Uyttenhove, C., et al.). 4-amino-N-(3-chloro-4-fluorophenyl)-N'-hydroxy-1,2,5-oxadiazole-3-carboximidamide (compound 51), a potent IDO1 inhibitor showed reduction of tumor growth in a mouse model for melanoma (Yue, E. W., et al., J. Med. Chem. 52: 7364; 2009). Two other potent IDO1 inhibitors from the same chemical series suppressed tumor growth in a mouse model for colon cancer (Koblish, H. K., et al., Mol. Cancer Ther. 9: 489; 2010). Many human tumors constitutively express IDO1 (Uyttenhove, C., et al.). In a series of 866 human tumors from diverse tissue-type origin more than half (i.e., 56%) expressed IDO1 (Theate, I., et al., Cancer Immunol. Res. 3: 161; 2014). High expression of IDO1 correlated with poor prognosis in a variety of cancers, including colorectal and endometrial cancer (Brandacher, G., et al., Clin. Cancer Res. 12: 1144; 2006; Ino, K., et al., Br. J. Cancer 95: 1555; 2006). In the absence of an immunologic stimulus, IDO1 is generally absent in most normal human tissues and cells (Theate, I., et al.).

Above data provide the biological basis for the use of IDO1 inhibitors as an approach for selective anti-cancer therapy.

It is understood that IDO1 inhibitors exert their anti-tumour activity either directly by affecting IDO1-expressing tumors or indirectly by inhibiting IDO1 in immune cells in the microenvironment of the tumor (Munn, D. H., et al., J. Immunol. 156: 523; 1996).

IDO1 inhibitors can be applied in anti-cancer therapy as single anti-cancer agent (monotherapy) or in combination with other anti-cancer agents. Administration of the IDO1 inhibitor 1-methyl-tryprophan (1-MT) increased the efficacy of various chemotherapeutic agents, e.g., cis-platin, doxo-rubicin, cyclophosphamide and paclitaxel in a mouse breast cancer model (Muller, A. J., et al., Nat. Med. 11: 312; 2005). 1-MT also increased the efficacy of a cancer vaccine in a syngeneic mouse lung carcinoma model (Ou, X., et al., J. Cancer Res. Clin. Oncol. 134: 525; 2008) and in a transgenic mouse model (Zeng, J., et al., Cancer Res. 69: 3963; 2009). 1-MT also increased the efficacy of antibodies targeting the immune checkpoints PD-1 and CTLA4 in mouse tumor models for melanoma and glioblastoma (Holmgaard, R. B., et al., J. Exp. Med. 210: 1389; 2013; Wainwright, D. A., et al., Clin. Cancer Res. 20: 5290; 2014).

IDO1 inhibitors may also be applied in anti-cancer therapy with other agents that activate the immune response, such as radiotherapy, or cellular therapies that attack tumor cells directly, such as natural killer cell or T cell therapies.

Certain viral infections, such as influenza virus, attenuate host immunity by stimulating local IDO1 activity (Yoshida, R., et al., Proc. Natl. Acad. Sci. USA 76: 4084; 1979). Treatment of influenza virus-infected mice with the IDO1 inhibitor 1-MT enhanced T cell response against the virus (Fox, J. M., et al., J. Gen. Virol. 94: 1451; 2013). Also certain parasitic infections, for instance, infection with *Leishmania major*, attenuates host immunity by stimulating IDO1 expression (Makala, L. H. C., et al., Journal of Infectious Diseases 203: 715; 2011). Treatment of these parasitic infections with the IDO1 inhibitor 1-MT reduced the parasite burden (Makala, L. H. C., et al.).

Above data provide a biologic basis for the use of IDO1 inhibitors in the treatment of viral and parasitic infections.

L-Tryptophan and metabolites formed along the kynurenine pathway play diverse role in the regulation of functions of the central nervous system (Vécsei, L., et al., Nat. Rev. Drug Discov. 12: 64; 2013). L-tryptophan is a precursor of serotonin (5-hydroxy tryptamine). Pro-inflammatory cytokine therapy with alpha-interferon (IFNα), as applied in hepatitis C and cancer, is associated with neuropsychiatric side-effects (Bonaccorso, S., et al., J. Affect. Disord. 72: 237; 2002). The development of depressive symptoms is, amongst others, related to decreased levels of peripheral serotonin (Maes, M., et al., Psychiatry Res. 49: 151; 1993). IFNα therapy in patients with hepatitis C causes decreased L-tryptophan levels and increased levels of the L-tryptophan metabolite kynurenine, indicating increased IDO1 activity (Bonaccorso, S., et al., J. Clin. Psychopharmacol. 22: 86; 2002). Administration of IFNα and other pro-inflammatory cytokines, such as interleukin-1β (IL-1β), IL-6 and tumor necrosis factor α (TNFα), to mice and rats induced a behavioral pattern characterized by increased sleep and decreased locomotor activity, referred to as 'sickness syndrome', which resembles the vegetative symptoms of depression in humans (Bianchi, M., et al., Neurosci. Lett. 148: 76; 1992; Bluthe, R. M., et al., Psychoneuroendocrinology 19: 197; 1994).

Apart from the effect of L-tryptophan on serotonin, metabolites formed in the kynurenine pathway have neurotoxic activity. Increased production of the metabolites 3-hydroxy-kynurenine and quinolinic acid have been found in the brains of people with Huntington's disease (Reynolds, G. P., et al., J. Neurochem. 50: 1959; 1988; Reynolds, G. P., and Pearson, S. J., Lancet 2: 979; 1989), Parkinson's disease (Ogawa, T., et al., Neurology 42: 1702; 1992) and human immunodeficiency virus (HIV) associated neurocognitive disorder (AIDS dementia complex) (Heyes, M. P., et al., FASEB J., 12: 881; 1998). Increased production of metabolites has also been implicated in neuronal damage in cognitive decline of aging (Moroni, F., et al., Neurosci. Lett. 47: 51; 1984), infections of the central nervous system (Heyes, M. P., et al., J. Neurol. Sci. 133: 112; 1995), malaria (Sanni, L. A., et al., Am. J. Pathol. 152: 611; 1998), ischemia (Saito, K., et al., J. Neurochem. 60: 180; 1993), hypoxia at birth (Kazda, H., et al., Pediatr. Res. 44: 368; 1998), traumatic brain injury (Sinze, E. H., et al., J. Cereb. Blood Flow Metab. 18: 610; 1998), epilepsy (Heyes, M. P., et al., Epilepsia 31: 172; 1990), and the development of psychiatric diseases, such as anxiety, depression and schizophrenia (Orlikov, A. B., et al., Biol. Psychiatry 36: 97; 1994; Issa, F., et al., Psychiatry Res. 52: 251; 1994).

Above data provide the biological basis for the application of IDO1 inhibitors in the treatment of neuropsychiatric and neurodegenerative disease, as well as cerebrovascular disease.

Increased expression of IDO1 has been observed in Crohn's disease in human patients (Lee, A., et al., PLoS ONE 9: e115848; 2014), while inactivation of the IDO1 gene in mice reduced the severity of colitis symptoms (Shon, W. J., et al., Sci. Rep. 5: 17305; 2015). This suggests that IDO1 inhibitors may be applied in the treatment of immune-related diseases and disorders, such as inflammatory bowel disease, colitis or Crohn's disease.

Diet-induced obesity can activate the production of cytokines, such as IFNγ, resulting in increased IDO1 in the brain and neuropsychiatric alterations (André, C. et al., Brain Behav. Immun. 41: 10; 2014). Furthermore, increased levels of IDO1 and kynurenine have been observed in diabetic patients (Favennec, M., et al., Obesity (Silver Spring) 23: 2066; 2015). This suggests that IDO1 inhibitors may be applied in the treatment of metabolic diseases, such as obesity and diabetes.

Thus inhibiting IDO1 activity, thereby increasing L-tryptophan concentrations and decreasing L-tryptophan metabolite concentration is a promising way of treating diseases, disorders and other pathological conditions arising from an increased L-tryptophan degradation.

Small molecule inhibitors of IDO1 are currently being developed to treat or prevent pathological conditions that are dependent or induced by increased degradation of L-tryptophan or by increased formation of metabolites of L-tryptophan, such as the diseases and disorders described above.

The use of small molecule inhibitors of IDO1 in therapy has been described. WO99/29310 describes methods for altering T cell-mediated immunity by altering local extracellular concentrations of L-tryptophan by inhibition or activation of L-tryptophan degradation. In particular, the use of IDO1 inhibitors to achieve inhibition of L-tryptophan degradation is described, disclosing the IDO1 inhibitor 1-methyl-tryptophan (1-MT). 1-MT was first described as an inhibitor of IDO1 in Cady, S. G., and Sono, M., Arch. Biochem. Biophys. 291: 326; 1991. 1-MT is a low-potency inhibitor of IDO1 with an inhibitory constant ($K_i$) of 7 µM.

WO2008/058178 A1 describes N-hydroxyamidines as inhibitors of IDO1. One of these compounds, compound 51, showed reduction of tumor growth in a mouse model for melanoma (Yue, E. W., et al., J. Med. Chem. 52: 7364; 2009) and in a mouse model for colon cancer (Yue, E. W., et al. ACS Med. Chem. Lett. 8: 486; 2017). A derivative of compound 51, epacadostat, showed further reduction of tumor growth in the colon cancer model (Yue, E. W. et al., ACS Med. Chem. Lett.). Epacadostat was generally well tolerated, with minimal immune-related adverse effects in a randomized, open-label, phase 2 clinical study in ovarian cancer patients (Kristeleit, R., et al., Gynecologic Oncology, in press; 2017; http://dx.doi.org/10.1016/j.ygyno.2017.07.005). In a phase 1 dose-escalation study in cancer patients with advanced solid malignancies, epacadostat induced significant dose-dependent reductions in plasma kynurenine levels and in the plasma/kynurenine ratio at all doses and in all patients (Beatty, R. W., et al. Clin. Cancer Res. 23: 3269; 2017). Studies investigating epacadostat in combination with other immunomodulatory agents are ongoing, such as combination with checkpoint inhibitors (http://clinicaltrials.gov; clinical studies NCT02178722, NCT02327078, NCT02318277, and NCT02298153), vaccines (NCT02166905 and NCT01961115) and cellular therapy (NCT02118285).

WO2015/188085 discloses N'-hydroxyacetimidamides that modulate the IDO1 enzyme. WO2011/056652 A1 describes imidazole derivatives as IDO1 inhibitors. WO2015/173764 A1 and WO2015/150097 A1 describe indole derivatives as inhibitors of IDO1.

Several compounds described as IDO1 inhibitors have been found to also inhibit the activity of tryptophan 2,3-dioxygenase (TDO) in biochemical assays (Seegers, N., et al., J. Biomol. Screen. 19: 1266; 2014), such as for example compound 5I from Yue, E. W., et al., and compound S7111, a fused imidazole (Selleck Chemicals, Munich, Germany; cat. no. S7111).

TDO is a structurally unrelated oxidoreductase that catalyzes the same reaction as IDO1 in the kynurenine pathway. TDO has a lower affinity ($K_{M,Trp}$) for L-tryptophan (190 µM) than IDO1 (6 µM) (Lu, C., et al. J. Am. Chem. Soc. 131: 12866; Klockow, J. L. et al., Organic Lett. 15: 235; 2013). TDO is mainly expressed in the liver where it regulates systemic L-tryptophan levels and L-tryptophan homeostasis (Schutz, G. et al., J. Biol. Chem. 247: 5237; 1995). Inhibition of TDO by an IDO1 inhibitor can however cause an unwanted alteration of these systemic L-tryptophan levels and L-tryptophan homeostasis. L-tryptophan is required for the de novo synthesis of reduced nucleotide amine dinucleotide (NADH), an essential co-enzyme in redox reactions and present in all living cells. Cross-reactivity of IDO1 inhibitors against TDO can be determined in enzyme assays.

Imidazole, and in particular 4-phenylimidazole, is a known binder of heme. Both IDO1 and TDO contain a heme cofactor. Also cytochrome P450 enzymes (CYPs), which are enzymes involved in the metabolism of drugs in the liver and other organs, contain a heme cofactor. Inhibition of CYP activity can cause adverse drug interactions, since by inhibition of CYP, one drug may affect the metabolism and clearance of a second drug. Consequently, the second drug may accumulate to toxic levels within the body, and adjustments of dosage levels may be necessary. Cross-reactivity of IDO1 inhibitors against CYPs can be determined in enzyme assays.

In view of the role of IDO1 in (the onset of) a variety of human diseases, disorders and other pathological conditions, there is a clear need for IDO1 inhibitors which do not have the limitations of current IDO1 inhibitors.

It is an object of the invention to provide novel IDO1 inhibitors. It is another object of the invention to provide novel IDO1 inhibitors which are selective for IDO1 and do not cross-react with TDO and/or CYP. It is yet a further objective of the present invention to provide novel, selective IDO1 inhibitors which have good potency.

The present invention provides for such IDO1 inhibitors. More specifically, the present invention provides for 3-hydroxyimidazolidin-4-one derivatives according to Formula I and pharmaceutically acceptable salts thereof. In particular, the present invention provides for 3-hydroxyimidazolidin-4-one derivatives which have been found to be potent inhibitors of IDO1. The present invention provides for 3-hydroxyimidazolidin-4-one derivatives which selectively inhibit IDO1 activity, their use for treatment or prevention of human disease, disorders or conditions associated with an increased activity of IDO1, as a sole agent or in combination with other active ingredients, as well as pharmaceutical compositions comprising such compounds and pharmaceutical carriers.

The present invention is to provide 3-hydroxyimidazolidin-4-one derivatives and pharmaceutically acceptable salts thereof, to pharmaceutical compositions comprising these compounds and their use in therapy. In particular, the present invention relates to the use of 3-hydroxyimidazolidin-4-one derivatives in the treatment and/or prevention of a diverse array of diseases, conditions and disorders associated with an increased activity of IDO1, including cancer, infections, central nervous system disease or disorder, and immune-related disorders.

More specifically, the present invention provides 3-hydroxyimidazolidin-4-one derivatives according to Formula I Formula I or pharmaceutically acceptable salts thereof, wherein,
$R^1$ is selected from the group consisting of of:

$R^{11}$ is H, halogen, (1-2C)alkyl or (1-2C)alkoxy, all alkyl and alkoxy groups optionally being substituted with one or more halogen;
$R^{12}$ is halogen, (1-2C)alkyl, (2-3C)alkynyl, (1-2C)alkylthio, (3-8C)cycloalkyl, cyano or nitro, all alkyl and cycloalkyl groups optionally being substituted with one or more halogen;
$R^{13}$ is H, halogen, (1-2C)alkyl, (1-2C)alkoxy, deuterium or $C^2H_3$ (trideuteriomethyl) all alkyl and alkoxy groups optionally being substituted with one or more halogen;
$R^{14}$ is H, halogen, (1-2C)alkyl or (1-2C)alkoxy, all alkyl and alkoxy groups optionally being substituted with one or more halogen;
$R^2$ is selected from the group consisting of:
 a) hydrogen,
 b) (1-6C)alkyl,
wherein (1-6C)alkyl optionally can be substituted,
$R^3$ is selected from the group consisting of:
 a) (6-10C)aryl,
 b) (1-9C)heteroaryl,
 c) (3-8C)cycloalkyl,
 d) (2-7C)heterocycloalkyl,
 e) (1-6C)alkyl,
wherein all groups optionally can be substituted,
$R^4$ is selected from the group consisting of:
 a) hydrogen,
 b) (1-6C)alkyl,
wherein (1-6C)alkyl optionally can be substituted,
$R^5$ is selected from the group consisting of:
 a) hydrogen,
 b) (1-6C)alkyl,
wherein (1-6C)alkyl optionally can be substituted,
A is selected from CH($R^a$) or C(O),
$R^a$ is selected from the group consisting of:
 a) hydrogen,
 b) (1-6C)alkyl,
wherein (1-6C)alkyl optionally can be substituted with fluorine or hydroxyl.

In an interesting embodiment, compounds according to Formula I which have been demonstrated to be IDO1 inhibitors with selectivity over TDO and/or CYP wherein $R^1$ is The terms as used herein refer to the following:
Halogen means fluorine, chlorine, bromine or iodine, chlorine, bromine or iodine being preferred halogens, bromine or iodine being more preferred.
(1-2C)Alkyl means an alkyl group having 1 to 2 carbon atoms, being methyl or ethyl, methyl being preferred. A methyl group may be indicated as Me or $CH_3$.
(1-3C)Alkyl means a branched or unbranched alkyl group having 1-3 carbon atoms, being methyl, ethyl, propyl or isopropyl.
(1-4C)Alkyl means a branched or unbranched alkyl group having 1-4 carbon atoms, being methyl, ethyl, propyl, isopropyl, butyl, isobutyl, sec-butyl or tert-butyl, (1-3C) alkyl groups being preferred.
(1-5C)Alkyl means a branched or unbranched alkyl group having 1-5 carbon atoms, for example methyl, ethyl, propyl, isopropyl, butyl, isobutyl, sec-butyl, tert-butyl, pentyl and isopentyl, (1-4C)alkyl groups being preferred.

(1-6C)Alkyl means a branched or unbranched alkyl group having 1-6 carbon atoms, for example methyl, ethyl, propyl, isopropyl, butyl, tert-butyl, n-pentyl and n-hexyl. (1-5C)alkyl groups are preferred, (1-4C)alkyl being more preferred.

(1-2C)Alkoxy means an alkoxy group having 1-2 carbon atoms, the alkyl moiety having the same meaning as previously defined. Methoxy groups are being preferred.

(1-3C)Alkoxy means an alkoxy group having 1-3 carbon atoms, the alkyl moiety having the same meaning as previously defined, (1-2C)alkoxy being preferred.

(2-3C)Alkenyl means a branched or unbranched alkenyl group having 2-3 carbon atoms, such as ethenyl or 2-propenyl.

(2-3C)Alkynyl means ethynyl or 2-propynyl.

(2-6C)Alkynyl means a branched or unbranched alkynyl group having 2-6 carbon atoms, for example ethynyl, propynyl, butynyl, 3-methylbut-1-yne and 3,3-dimethylbut-1-yne. (2-3C)alkynyl groups are preferred.

(3-8C)Cycloalkyl means a cycloalkyl group having 3-8 carbon atoms, being cyclopropyl, cyclobutyl, cyclopentyl, cyclohexyl, cycloheptyl or cyclooctyl. Preferred (3-8C) cycloalkyl groups are cyclohexyl, cyclopentyl or cyclobutyl, more preferred (3-8C)cycloalkyl groups are cyclopropyl and cyclohexyl.

(2-7C)Heterocycloalkyl means a heterocycloalkyl group having 2-7 carbon atoms, preferably 2-5 carbon atoms, and one or two heteroatoms selected from N, O and/or S. Preferred heteroatoms are N or O. Preferred (2-7C)heterocycloalkyl groups are azetidinyl, pyrrolidinyl, piperidinyl, piperazinyl, homopiperidinyl, morpholinyl or thiomorpholinyl, more preferred (2-7C)heterocycloalkyl groups are pyrrolidinyl and piperidyl The heterocycloalkyl group may be attached via a heteroatom if feasible.

(6-10C)Aryl means an aromatic hydrocarbon group having 6-10 carbon atoms, such as phenyl, naphthyl, tetrahydronaphthyl or indenyl. The preferred (6-10C)aryl group is phenyl.

(1-5C)Heteroaryl means a substituted or unsubstituted aromatic group having 5-6 ring atoms of which 1-5 carbon atoms and 1-4 heteroatoms selected from N, O and/or S. The (1-5C)heteroaryl may optionally be substituted. Examples of typical (1-5C) heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; Preferred (1-5C) heteroaryl groups are thienyl, isoxazolyl, pyrazolyl, pyridyl, pyrimidyl, pyrazinyl, more preferred (1-5C)heteroaryls are pyridinyl, pyrazolyl and thienyl.

(1-9C)Heteroaryl means a substituted or unsubstituted aromatic group having 8-10 atoms of which 1-9 carbon atoms and 1-5 heteroatoms selected from N, O and/or S. The (1-9C)heteroaryl may optionally be substituted. Examples of typical (1-9C) heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, isobenzofuranyl, chromenyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinolinyl, cinnolinyl, pteridinyl, isothiazolyl, and the like. (1-5C)Heteroaryl groups are being preferred.

(3-6C)Cycloalkylamino means an amino group, monosubstituted with an cycloalkyl group containing 3-6 carbon atoms having the same meaning as previously defined.

(1-6C)Alkylamino means an amino group, monosubstituted with an alkyl group containing 1-6 carbon atoms having the same meaning as previously defined.

(2-7C)Heterocycloalkylamino means an amino group, monosubstituted with a (2-7)heterocycloalkyl group containing 2-7 carbon atoms having the same meaning as previously defined.

(6-10C)Arylamino means an amino group, monosubstituted with a (6-10C)aryl group having the same meaning as previously described.

(1-9C)Heteroarylamino means an amino group, monosubstituted with a (1-9C)heteroaryl group having the same meaning as previously described.

(1-3C)alkoxy(1-6C)alkyl means a (1-6C)alkyl group, substituted with a (1-3C)alkoxy group having the same meaning as previously described.

(2-7C)Heterocycloalkyl(1-6C)alkyl means a (1-6C)alkyl group, substituted with a (2-7C)heterocycloalkyl group having the same meaning as previously described.

(3-8C)Cycloalkyl(1-6C)alkyl means a (1-6C)alkyl group, substituted with a (3-8C)cycloalkyl group having the same meaning as previously described.

(1-3C)alkoxy(1-6C)alkylamino means an amino group, monosubstituted with a (1-3C)alkoxy(1-6C)alkyl group having the same meaning as previously described.

(1-3C)alkoxy(1-6C)alkylaminocarbonyl means a carbonyl group substituted with a (1-3C)alkoxy(1-6C)alkylamino group having the same meaning as previously described.

(1-6C)Alkylcarbonyl means a carbonyl group, substituted with a (1-6C)alkyl group having the same meaning as previously described.

(1-6C)Alkylcarbonylamino means an amino group, monosubstituted with a (1-6C)alkylcarbonyl group having the same meaning as previously described.

(1-6C)Alkylsulfonyl means a sulfonyl group, substituted with a (1-6C)alkyl group having the same meaning as previously described.

(1-6C)Alkylsulfonylamino means an amino group, monosubstituted with a (1-6C)alkylsulfonyl group having the same meaning as previously described.

(6-10C)Aryloxy means a (6-10C)aryl group, having the same meaning as previously described, attached via a ring carbon to an exocyclic oxygen.

(1-6C)Alkylsulfonylamino(1-6C)alkyl means a (1-6C)alkyl group, substituted with a (1-6C)alkylsulfonylamino group having the same meaning as previously described.

Aminosulfonylamino(1-6C)alkyl means a (1-6C)alkyl group, substituted with an aminosulfonylamino group.

(1-6C)Alkylcarbonylamino(2-6C)alkynyl means a (2-6C) alkynyl group, substituted with a (1-6C)alkylcarbonylamino group having the same meaning as previously described.

Amino(2-6C)alkynyl means a (2-6C)alkynyl group, substituted with an amine.

Aminosulfonylamino(2-6C)alkynyl means a (2-6C)alkynyl group, substituted with an aminosulfonylamino group.

(3-8C)Cycloalkyl(2-3C)alkynyl means a (2-3C)alkynyl group, substituted with a (3-8C)cycloalkyl group having the same meaning as previously described.

(1-6C)Alkylsulfonylamino(2-6C)alkynyl means a (2-6C) alkynyl group, substituted with a (1-6C)alkylsulfonylamino group having the same meaning as previously described.

(6-10C)Aryl(1-6C)alkyl means a (1-6C)alkyl group, substituted with a (6-10C)aryl group having the same meaning as previously described.

(1-3C)Alkylsulfonyl means a sulfonyl group, substituted with a (1-3C)alkyl group having the same meaning as previously described.

(1-3C)Alkylsulfonyl(6-10C)aryl means a (6-10C)aryl group, substituted with a (1-3C)alkylsulfonyl group having the same meaning as previously described.

Di[(1-6C)alkyl]amino means an amino group, disubstituted with alkyl group(s) each independently containing 1-6 carbon atoms and having the same meaning as previously defined. Preferred di[(1-6C)alkyl]amino group is dimethylamino.

(1-4C)alkoxy[(2-4C)alkoxy]$_m$(1-6C)alkyl means a (1-6C) alkyl group having the same meaning as previously defined, substituted with one or more (2-4C)alkoxy groups, i.e. m is an integer greater than or equal to 0, the alkoxy group being linearly connected one to another. The last (2-4C)alkoxy group being substituted with an (1-4C) alkoxy group. In the (1-4C)alkoxy[(2-4C)alkoxy]$_m$(1-6C) alkyl group, the preferred (1-6C)alkyl is ethyl, preferably m is 0,1,2,3 or 4, m is 0,1 or 2 being more preferred. (1-4C)alkoxy[(2-4C)alkoxy]$_m$(1-6C)alkyl includes an (1-6C)alkyl group substituted with polyethylene glycol.

In the above definitions with multifunctional groups, the attachment point is at the last group.

When, in the definition of a substituent, is indicated that "all of the alkyl groups" of said substituent are optionally substituted, this also includes the alkyl moiety of an alkoxy group.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds.

"Stable compound" or "stable structure" is defined as a compound or structure that is sufficiently robust to survive isolation to a useful degree of purity from a reaction mixture, and formulation into an efficacious therapeutic agent.

The term "optionally substituted" means optional substitution with the specified groups, radicals or moieties.

The compounds according to formula I of the present invention were found to inhibit IDO1 activity, which make them excellent candidates for use in the treatment or prevention of diseases, disorders and other pathological conditions associated with an increased L-tryptophan degradation.

In one embodiment, the invention relates to a compound according to Formula I, wherein $R^2$ is hydrogen.

In another embodiment, the invention relates to a compound according to Formula I, wherein A is C(O) or CH($R^a$). More preferably, A is C(O), CH$_2$ or CH(CH$_3$), in particular C(O) or CH(CH$_3$).

In yet another embodiment, the invention relates to a compound according to Formula I, wherein $R^4$ and $R^5$ are hydrogen.

In again another embodiment, the invention relates to compounds according to Formula I, wherein $R^1$ is

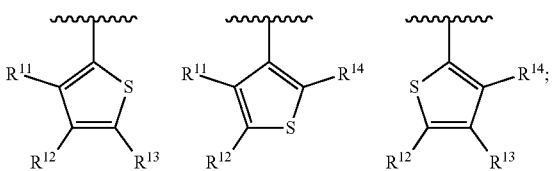

$R^{11}$ is H, halogen, (1-2C)alkyl or (1-2C)alkoxy, all alkyl and alkoxy groups optionally being substituted with one or more halogen; $R^{12}$ is halogen, (1-2C)alkyl, (2-3C)alkynyl, (1-2C)alkylthio, (3-8C)cycloalkyl, cyano or nitro, all alkyl and cycloalkyl groups optionally being substituted with one or more halogen; $R^{13}$ is H, halogen, (1-2C)alkyl, (1-2C) alkoxy, deuterium or C$^2$H$_3$ (trideuteriomethyl), all alkyl and alkoxy groups optionally being substituted with one or more halogen; $R^{14}$ is H, halogen, (1-2C)alkyl or (1-2C)alkoxy, all alkyl and alkoxy groups optionally being substituted with one or more halogen.

In yet another embodiment the invention relates to a compound according to Formula I wherein $R^3$ is selected from the group consisting of: (6-10C)aryl, (1-9C)heteroaryl, (3-8C)cycloalkyl, (2-7C)heterocycloalkyl and (1-6C)alkyl, preferably (6-10C)aryl, (1-9C)heteroaryl and (3-8C)cycloalkyl, more preferably (6-10C)aryl, wherein all groups optionally can be substituted. Particularly preferred are compounds according to formula I wherein $R^3$ is

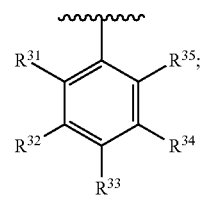

$R^{31}$ and $R^{35}$ are independently selected from the group consisting of: hydrogen, halogen, cyano, (1-6C)alkyl, (2-3C)alkenyl, (2-3C)alkynyl and (1-2C)alkoxy, all alkyl and alkoxy groups optionally being substituted with one or more halogen; $R^{32}$ and $R^{34}$ are independently selected from the group consisting of: hydrogen, halogen, nitro, B(OH)$_2$, cyano, (1-6C)alkyl, (2-6C)alkenyl, (2-6C)alkynyl, (1-2C) alkoxy, (3-8C)cycloalkyl, (2-7C)heterocycloalkyl, (6-10C) aryl or (1-9C)heteroaryl, aminosulfonylamino(2-6C)alkynyl, (1-6C)alkylsylfonylamino(2-6C)alkynyl, (1-6C) carbonylamino(1-6C)alkynyl, each alkyl, alkenyl, alkynyl, alkoxy, cycloalkyl, heterocycloalkyl, aryl or heteroaryl optionally being substituted with one or more halogen, (1-3C)alkyl, (1-3C)alkoxy or cyano, OR$^{321}$, N(R$^{322}$,R$^{323}$), C(O)R$^{324}$, CH(R$^b$)N(R$^{322}$,R$^{323}$); R$^{321}$ is selected from the group consisting of: hydrogen, (1-6C)alkyl, (1-4C)alkoxyl [(2-4C)alkoxy]$_m$(1-6C)alkyl, (3-8C)cycloalkyl, (2-7C)heterocycloalkyl, (6-10C)aryl, (1-9C)heteroaryl), (2-7C)heterocycloalkyl(1-6C)alkyl, (3-8C)cycloalkyl(1-6C)alkyl, all alkyl, alkoxy, cycloalkyl, heterocycloalkyl groups optionally substituted with one or more halogen, one or more (1-3C)alkyl; m is 0-4; R$^{322}$ and R$^{323}$ are independently selected from the group consisting of: hydrogen, (1-6C) alkyl, (1-6C)alkylcarbonyl, (1-6C)alkylsulfonyl, aminosulfonyl, all alkyl groups optionally substituted with one or more halogen; R$^{324}$ is selected from the group consisting of: (1-6C)alkyl, (1-6C)alkylamino, (1-6C)alkoxy(1-6C)alkylamino, (6-10C)arylamino, (1-9C)heteroarylamino, (2-7C) heterocycloalkylamino; R$^b$ is selected from the group consisting of: hydrogen or (1-6C)alkyl; $R^{33}$ is selected from the group consisting of: hydrogen, halogen, cyano, (1-6C)alkyl, (2-3C)alkenyl, (2-6C)alkynyl, (1-3C)alkoxy, (6-10C)aryl, (1-5C)heteroaryl, (2-7C)heterocycloalkyl, (3-8C)cycloalkyl, (6-10C)aryloxy, (1-6C)alkylsulfonylamino(1-6C)alkyl, aminosulfonylamino(1-6C)alkyl, (3-8C)cycloalkyl(1-6C)alkyl, (1-6C)alkylcarbonylamino(2-6C)alkynyl, amino(2-6C)alkynyl, aminosulfonylamino(2-6C)alkynyl, (3-8C)cycloalkyl(2-3C)alkynyl, (1-6C)alkylsulfonylamino(2-6C)alkynyl, (1-3C)alkyl(2-3C)alkenyl, (6-10C)aryl(1-6C)alkyl, (1-3C)alkylsulfonyl(6-10C)aryl, di[(1-6C)alkyl]amino, all alkyl and alkoxy groups optionally being substituted with one or more halogen, all (1-5C)heteroaryl groups optionally being substituted with one or more halogen, one or more (1-6C)alkyl.

In a preferred embodiment, the invention provides for compounds according to Formula I which have been demonstrated to be IDO1 inhibitors with excellent selectivity over TDO and/or CYP, wherein $R^1$ is

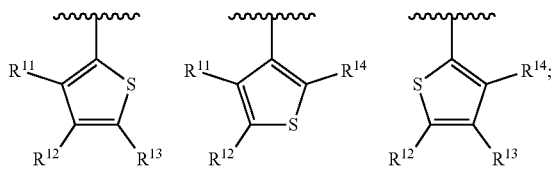

$R^{11}$, $R^{14}$ is H, $R^{12}$ is chlorine, bromine, iodine, nitro, (1-2C)alkyl, or (2-3C)alkynyl, all alkyl groups optionally being substituted with one or more halogen, $R^{13}$ is H, deuterium, $C^2H_3$ (trideuteriomethyl) or halogen. Particularly preferred selective IDO1 inhibitors are those compounds according to Formula I wherein A is C(O) or CH($R^a$); $R^1$ is

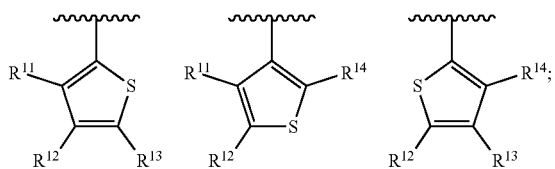

$R^{11}$, $R^{14}$ is H, $R^{12}$ is chlorine, bromine, iodine, nitro, (1-2C)alkyl, or (2-3C)alkynyl, all alkyl groups optionally being substituted with one or more halogen, $R^{13}$ is H, deuterium, $C^2H_3$ (trideuteriomethyl) or halogen; $R^2$ is hydrogen; $R^4$ and $R^5$ are hydrogen.

In a more preferred embodiment, the invention provides for compounds according to formula I which are selective IDO1 inhibitors found to have excellent potency, wherein furthermore $R^3$ is

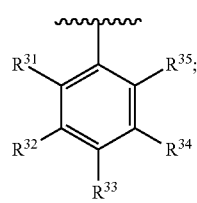

$R^{31}$ and $R^{35}$ are independently selected from the group consisting of: hydrogen, fluoro and chloro; $R^{32}$ and $R^{34}$ are independently selected from the group consisting of: hydrogen, halogen, nitro, B(OH)$_2$, cyano, (1-6C)alkyl, (2-6C)alkenyl, (2-6C)alkynyl, (1-2C)alkoxy, (3-8C)cycloalkyl, (2-7C)heterocycloalkyl, (6-10C)aryl or (1-9C)heteroaryl, aminosulfonylamino(2-6C)alkynyl, (1-6C)alkylsylfonylamino(2-6C)alkynyl, (1-6C)carbonylamino(1-6C)alkynyl, each alkyl, alkenyl, alkynyl, alkoxy, cycloalkyl, heterocycloalkyl, aryl or heteroaryl optionally being substituted with one or more halogen, (1-3C)alkyl, (1-3C)alkoxy or cyano, OR$^{321}$, N(R$^{322}$,R$^{323}$), C(O)R$^{324}$, CH(R$^b$)N(R$^{322}$, R$^{323}$); R$^{321}$ is selected from the group consisting of: hydrogen, (1-6C)alkyl, (1-4C)alkoxyl[(2-4C)alkoxy]$_m$(1-6C)alkyl, (3-8C)cycloalkyl, (2-7C)heterocycloalkyl, (6-10C)aryl, (1-9C)heteroaryl), (2-7C)heterocycloalkyl(1-6C)alkyl, (3-8C)cycloalkyl(1-6C)alkyl, all alkyl, alkoxy, cycloalkyl, heterocycloalkyl groups optionally substituted with one or more halogen, one or more (1-3C)alkyl; m is 0-4; R$^{322}$ and R$^{323}$ are independently selected from the group consisting of: hydrogen, (1-6C)alkyl, (1-6C)alkylcarbonyl, (1-6C)alkylsulfonyl, aminosulfonyl, all alkyl groups optionally substituted with one or more halogen; R$^{324}$ is selected from the group consisting of: (1-6C)alkyl, (1-6C)alkylamino, (1-6C)alkoxy(1-6C)alkylamino, (6-10C)arylamino, (1-9C)heteroarylamino, (2-7C)heterocycloalkylamino; R$^b$ is selected from the group consisting of: hydrogen or (1-6C)alkyl; R$^{33}$ is selected from the group consisting of: hydrogen, halogen, (1-6C)alkyl, (2-3C)alkenyl, (2-6C)alkynyl, (1-3C)alkoxy, (6-10C)aryl, (1-5C)heteroaryl, (3-8C)cycloalkyl, (1-6C)alkylsulfonylamino(1-6C)alkyl, aminosulfonylamino(1-6C)alkyl, (3-8C)cycloalkyl(1-6C)alkyl, amino(2-6C)alkynyl, aminosulfonylamino(2-6C)alkynyl, (3-8C)cycloalkyl(2-3C)alkynyl, (1-6C)alkylsulfonylamino(2-6C)alkynyl, (1-3C)alkoxy(1-6C)alkylaminocarbonyl, di[(1-6C)alkyl]amino, all alkyl and alkoxy groups optionally being substituted with one or more halogen, all (1-5C)heteroaryl groups optionally being substituted with one or more halogen, one or more (1-6C)alkyl. Even more selective IDO1 inhibitors with excellent potency have been found to be compounds according to Formula I, wherein $R^1$ is

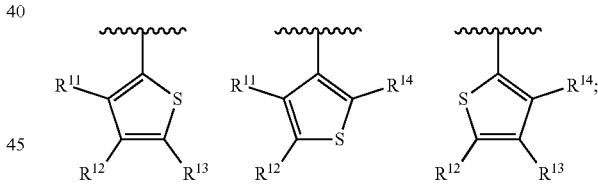

$R^{11}$, $R^{14}$ is H, $R^{12}$ is chlorine, bromine, iodine, nitro, (1-2C)alkyl, or (2-3C)alkynyl, all alkyl groups optionally being substituted with one or more halogen, $R^{13}$ is H, deuterium, $C^2H_3$ (trideuteriomethyl) or halogen; $R^2$ is hydrogen; $R^4$ and $R^5$ are hydrogen; and $R^3$ is

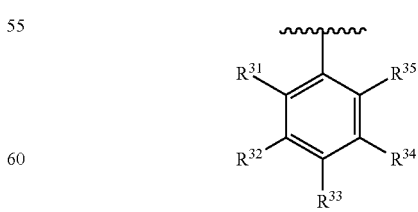

wherein $R^{31}$ and $R^{35}$ are independently selected from the group consisting of: hydrogen, fluoro and chloro; $R^{32}$ and $R^{34}$ are independently selected from the group consisting of: hydrogen, halogen, nitro, B(OH)$_2$, cyano, (1-6C)alkyl, (2-6C)alkenyl, (2-6C)alkynyl, (1-2C)alkoxy, (3-8C)cycloalkyl, (2-7C)heterocycloalkyl, (6-10C)aryl or (1-9C)heteroaryl, aminosulfonylamino(2-6C)alkynyl, (1-6C)alkylsylfonylamino(2-6C)alkynyl, (1-6C)carbonylamino(1-6C)alkynyl, each alkyl, alkenyl, alkynyl, alkoxy, cycloalkyl, heterocycloalkyl, aryl or heteroaryl optionally being substituted with one or more halogen, (1-3C)alkyl, (1-3C)alkoxy or cyano, OR$^{321}$, N(R$^{322}$,R$^{323}$), C(O)R$^{324}$, CH(R$^b$)N(R$^{322}$, R$^{323}$); R$^{321}$ is selected from the group consisting of: hydrogen, (1-6C)alkyl, (1-4C)alkoxyl[(2-4C)alkoxy]$_m$(1-6C)alkyl, (3-8C)cycloalkyl, (2-7C)heterocycloalkyl, (6-10C)aryl, (1-9C)heteroaryl), (2-7C)heterocycloalkyl(1-6C)alkyl, (3-8C)cycloalkyl(1-6C)alkyl, all alkyl, alkoxy, cycloalkyl, heterocycloalkyl groups optionally substituted with one or more halogen, one or more (1-3C)alkyl; m is 0-4; R$^{322}$ and R$^{323}$ are independently selected from the group consisting of: hydrogen, (1-6C)alkyl, (1-6C)alkylcarbonyl, (1-6C)alkylsulfonyl, aminosulfonyl, all alkyl groups optionally substituted with one or more halogen; R$^{324}$ is selected from the group consisting of: (1-6C)alkyl, (1-6C)alkylamino, (1-6C)alkoxy(1-6C)alkylamino, (6-10C)arylamino, (1-9C)heteroarylamino, (2-7C)heterocycloalkylamino; R$^b$ is selected from the group consisting of: hydrogen or (1-6C)alkyl; R$^{33}$ is selected from the group consisting of: hydrogen, halogen, (1-6C)alkyl, (2-3C)alkenyl, (2-6C)alkynyl, (1-3C)alkoxy, (6-10C)aryl, (1-5C)heteroaryl, (3-8C)cycloalkyl, (1-6C)alkylsulfonylamino(1-6C)alkyl, aminosulfonylamino(1-6C)alkyl, (3-8C)cycloalkyl(1-6C)alkyl, amino(2-6C)alkynyl, aminosulfonylamino(2-6C)alkynyl, (3-8C)cycloalkyl(2-3C)alkynyl, (1-6C)alkylsulfonylamino(2-6C)alkynyl, (1-3C)alkoxy(1-6C)alkylaminocarbonyl, di[(1-6C)alkyl]amino, all alkyl and alkoxy groups optionally being substituted with one or more halogen, all (1-5C)heteroaryl groups optionally being substituted with one or more halogen, one or more (1-6C)alkyl.

In a particularly interesting embodiment, the invention provides for compounds according to Formula I which have been demonstrated to be very potent IDO1 inhibitors with excellent selectivity over TDO and/or CYP, wherein preferably A is C(O) or CH(CH$_3$); R$^1$ is

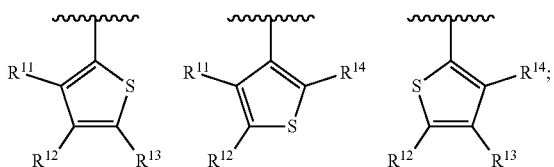

R$^{11}$, R$^{14}$ is H, R$^{12}$ is chlorine, bromine, iodine, nitro, (1-2C)alkyl, or (2-3C)alkynyl, all alkyl groups optionally being substituted with one or more halogen, R$^{13}$ is H, deuterium, C$^2$H$_3$ (trideuteriomethyl) or halogen; R$^2$ is hydrogen; R$^4$ and R$^5$ are hydrogen; and R$^3$ is

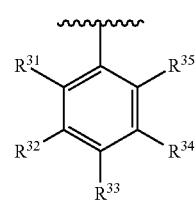

wherein R$^{31}$ and R$^{35}$ are independently selected from the group consisting of: hydrogen, fluoro and chloro; R$^{32}$ and R$^{34}$ are independently selected from the group consisting of: hydrogen, halogen, nitro, B(OH)$_2$, cyano, (1-6C)alkyl, (2-6C)alkenyl, (2-6C)alkynyl, (1-2C)alkoxy, (3-8C)cycloalkyl, (2-7C)heterocycloalkyl, (6-10C)aryl or (1-9C)heteroaryl, aminosulfonylamino(2-6C)alkynyl, (1-6C)alkylsylfonylamino(2-6C)alkynyl, (1-6C)carbonylamino(1-6C)alkynyl, each alkyl, alkenyl, alkynyl, alkoxy, cycloalkyl, heterocycloalkyl, aryl or heteroaryl optionally being substituted with one or more halogen, (1-3C)alkyl, (1-3C)alkoxy or cyano, OR$^{321}$, N(R$^{322}$,R$^{323}$), C(O)R$^{324}$, CH(R$^b$)N(R$^{322}$, R$^{323}$); R$^{321}$ is selected from the group consisting of: hydrogen, (1-6C)alkyl, (1-4C)alkoxyl[(2-4C)alkoxy]$_m$(1-6C)alkyl, (3-8C)cycloalkyl, (2-7C)heterocycloalkyl, (6-10C)aryl, (1-9C)heteroaryl), (2-7C)heterocycloalkyl(1-6C)alkyl, (3-8C)cycloalkyl(1-6C)alkyl, all alkyl, alkoxy, cycloalkyl, heterocycloalkyl groups optionally substituted with one or more halogen, one or more (1-3C)alkyl; m is 0-4; R$^{322}$ and R$^{323}$ are independently selected from the group consisting of: hydrogen, (1-6C)alkyl, (1-6C)alkylcarbonyl, (1-6C)alkylsulfonyl, aminosulfonyl, all alkyl groups optionally substituted with one or more halogen; R$^{324}$ is selected from the group consisting of: (1-6C)alkyl, (1-6C)alkylamino, (1-6C)alkoxy(1-6C)alkylamino, (6-10C)arylamino, (1-9C)heteroarylamino, (2-7C)heterocycloalkylamino; R$^b$ is selected from the group consisting of: hydrogen or (1-6C)alkyl; R$^{33}$ is selected from the group consisting of: hydrogen, halogen, (1-6C)alkyl, (2-3C)alkenyl, (2-6C)alkynyl, (1-3C)alkoxy, (6-10C)aryl, (1-5C)heteroaryl, (3-8C)cycloalkyl, (1-6C)alkylsulfonylamino(1-6C)alkyl, aminosulfonylamino(1-6C)alkyl, (3-8C)cycloalkyl(1-6C)alkyl, amino(2-6C)alkynyl, aminosulfonylamino(2-6C)alkynyl, (3-8C)cycloalkyl(2-3C)alkynyl, (1-6C)alkylsulfonylamino(2-6C)alkynyl, (1-3C)alkoxy(1-6C)alkylaminocarbonyl, di[(1-6C)alkyl]amino, all alkyl and alkoxy groups optionally being substituted with one or more halogen, all (1-5C)heteroaryl groups optionally being substituted with one or more halogen, one or more (1-6C)alkyl.

The invention also provides for those compounds wherein all specific definitions of R$^1$-R$^5$, A, R$^a$, R$^b$, m, R$^{11-14}$, R$^{31-35}$, R$^{321}$, R$^{322}$, R$^{323}$ and R$^{324}$ and all substituent groups in the various aspects of the inventions defined here above occur in any combination within the definition of the compound of Formula I. Suitable compounds according to the invention are the compounds according to Formula I of examples 1 to 136. The compounds according to Formula I have an inhibitory potency on IDO1 with an IC$_{50}$ of 25 μM or lower, in particular 20 μM or less, more particular 10 μM or less. More preferably, the compounds according to Formula I have an inhibitory potency on IDO1 with an IC$_{50}$ of 5 μM or less, such as e.g. the compounds of examples 3, 10, 11, 12, 13, 14, 16, 18, 22, 23, 29, 30, 31, 35, 45a, 46a, 49a, 53, 54, 56, 64, 67, 68, 71, 92, 95, 97, 100, 108, 109 and 126. Particularly preferred are compounds according to Formula I which have an inhibitory potency on IDO1 with an IC$_{50}$ of 1 μM or less, such as e.g. the compounds of examples 1, 2, 4, 7, 8, 9, 20, 21, 28, 33, 36, 37, 38, 39, 40, 41, 42, 43, 44, 45b, 46b, 47a, 47b, 48a, 48b, 49b, 50, 51, 52, 55, 63, 65, 66, 69, 73, 74, 75, 76-91, 93, 94, 96, 98, 99, 101-107, 111-117, 118b, 119b, 120b, 121b, 122, 123, 124, 125, 127, 128 and 129-136.

The term IC$_{50}$ means the concentration of the test compound that is required for 50% inhibition of its maximum effect in vitro.

Inhibition of IDO1 activity can be measured by determining the enzymatic conversion of L-tryptophan into N-formylkynurenine (NFK) in a reaction mixture containing IDO1 and test compound. The formation of NFK can be detected directly by, for instance, high-performance liquid chromatography (HPLC) methods, or by intrinsic fluorescence. The formation of NFK can also be measured by using a chemical probe that reacts with NFK to form a fluorescent product (Seegers, N. et al., J. Biomol. Screen. 19: 1266; 2014). Alternatively, the NFK formed in the reaction can be determined after a chemical reaction, i.e., NFK can be hydrolyzed to kynurenine, which can be measured by absorbance, fluorescence or HPLC methods (Matin, A., et al., Anal. Biochem. 349: 96; 2006).

The biological activity of IDO1 inhibitors can be measured by applying above detection methods to cells that are treated with test compound. The expression of IDO1 can be induced in many different cell lines by stimulation with IFNγ (Takikawa, O., et al., J. Biol. Chem. 263: 2041; 1988; Seegers, et al.), or IDO1 can be expressed in cells that lack endogenous IDO1 by transfection of an expression vector containing IDO1 cDNA.

The compounds of Formula I can form salts which are also within the scope of this invention. The term "salt(s)", as employed herein, denotes acidic salts formed with inorganic and/or organic acids, as well as basic salts formed with inorganic and/or organic bases. In addition, when a compound of Formula I may contain both a basic moiety, such as, but not limited to a pyridine or imidazole, and an acidic moiety, zwitterions ("inner salts") may be formed and are included within the term "salt(s)" as used herein. Pharmaceutically acceptable (i.e., non-toxic, physiologically acceptable) salts are preferred. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartrates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, J.of Pharm. Sci. (1977) 66(1) 1-19; P. Gould, Int. J. Pharm. (1986) 33 201-21 7; Anderson et al, The Practice of Medicinal Chemistry (1996), Academic Press, New York; and in The Orange Book (Food & Drug Administration, Washington, D.C. on their website).

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, tert-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The compounds of Formula I may have the ability to crystallize in more than one form, a characteristic known as polymorphism, and it is understood that such polymorphic forms ("polymorphs") are within the scope of Formula I. Reference to a compound of Formula I herein is understood to include reference to all polymorphic forms thereof. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of Formula I contain asymmetric or chiral centers, and, therefore, exist in different stereoisomeric forms (See e.g. examples 45-49 and 118-121). It is intended that all stereoisomeric forms of the compounds of Formula I as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention. Reference to a compound of Formula I herein is understood to include reference to all stereoisomeric forms thereof or mixtures of these isomeric forms.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula I may be atropisomers (e.g. substituted biaryls) and are considered as part of this invention. Enantiomers can also be separated by use of a chiral HPLC column.

It is also possible that the compounds of Formula I may exist in different tautomeric forms, and all such forms are embraced within the scope of the invention. Also, for example, all keto-enol and imine-enamine forms of the compounds are included in the invention. Reference to a compound of Formula I herein is understood to include reference to all tautomeric forms thereof.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the compounds according to the invention.

The compounds having Formula I or the pharmaceutically accepted salts may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H) (See e.g. Example 111 and 114). Protium is the predominant hydrogen isotope found in nature.

Substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herein below, by substituting an appropriate isotopically labeled reagent for a non-isotopically labeled reagent.

In a second aspect of the invention, the compounds according to Formula I or a pharmaceutically acceptable salt thereof can be used as a medicament in therapy. More in particular, the compounds according to Formula I or a pharmaceutically acceptable salt thereof can be used for the treatment of diseases or conditions caused by, or associated with increased activity of IDO1, in particular diseases or disorders caused by, or associated with increased tryptophan metabolism.

In particular, the compounds of Formula I or their salts, and pharmaceutical compositions thereof can be used to treat cancer.

In another embodiment, the compounds of the present invention, their salts and pharmaceutical compositions thereof can be used to increase the efficacy of one or more other anti-cancer agents, e.g., chemotherapeutic agents, vaccines, antibodies, or cell therapies.

In yet another embodiment, the compounds of the present invention, their salts and pharmaceutical compositions thereof can be used to treat infections with viruses or microorganisms.

In again another aspect, the compounds of the present invention, their salts and pharmaceutical compositions thereof can be used to treat or prevent the negative effects of cytokines on the central nervous system, which are related to increased activity of IDO1, in particular in which tryptophan metabolism plays a role, such as neuropsychiatric disease.

In yet again another embodiment, the compounds of the present invention, their salts and pharmaceutical compositions thereof can be used to treat or prevent the negative effects of cytokine therapy or other immune-based therapies on the central nervous system.

In a further embodiment, the compounds of the present invention, their salts and pharmaceutical compositions thereof can be used to treat or prevent the negative effects cytokines on IDO1 activity in metabolic disorders, such as diabetes or obesity.

In yet a further embodiment, the compounds of the present invention, their salts and pharmaceutical compositions thereof can be used to treat or prevent neurodegenerative disease, such as Parkinson's or Huntington's disease.

In another embodiment of the invention, the compounds of the present invention their salts and pharmaceutical compositions thereof can be used to treat immune-related disease and disorders.

A further aspect of the invention resides in the use of a compound of Formula 1, pharmaceutically acceptable salts and pharmaceutical compositions thereof in the treatment of diseases, disorders and pathological conditions caused by or associated with overexpression or over-activity of the IDO1 protein, in particular diseases, disorders and conditions wherein an increased tryptophan degradation plays a prominent role.

Included herein are methods of treatment and/or pharmaceutical compositions in which at least one compound of Formula I or a pharmaceutically acceptable salt thereof is administered as a single agent or in combination with at least one other active agent. The other active agent can be a chemotherapeutic agent, an antibody, or an active polypeptide. Thus, in one embodiment, the invention concerns a compound of Formula I or salt thereof in combination with one or more other drug(s).

In a third aspect, the invention further provides a pharmaceutical composition, which comprises a compound of Formula I and salts thereof, and one or more pharmaceutically acceptable carriers, diluents, or excipients. The carrier(s), diluent(s) or excipient(s) must be acceptable in the sense of being compatible with the other ingredients of the formulation and not deleterious to the recipient thereof.

Mixed with such pharmaceutically acceptable auxiliaries, e.g. as described in the standard reference, Gennaro, A. R. et al., Remington: The Science and Practice of Pharmacy (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

Pharmaceutical compositions of the present invention may be presented in unit dose forms containing a predetermined amount of active ingredient per unit dose. Such a unit may contain, for example, 5 µg to 1 g, preferably 1 mg to 700 mg, more preferably 5 mg to 100 mg of a compound of the Formula I, depending on the condition being treated, the route of administration and the age, weight and condition of the patient. Such unit doses may therefore be administered more than once a day. Preferred unit dosage compositions are those containing a daily dose or sub-dose (for administration more than once a day), as here in above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, sublingual, subcutaneous, local or parenteral (including intravenous and intramuscular) route, and the like, all in unit dosage forms for administration. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

The compound of the present invention can also be administered as a protein-drug conjugate. The compound can be covalently bound, optionally with a linker molecule to a peptide or protein, such as a binding protein for example an antibody. Using this approach, the conjugate can be delivered to the target tissue. Methods to prepare such conjugates are well known to those skilled in the art.

The compound of the present invention can also be administered as a (bio)polymeric nanoparticulate-drug system (Park, W. et al., Nanomed. Nanobiotechnol. 7: 494-508; 2015). The compound can be covalently bound, optionally with a linker molecule to the nanoparticulate system for example, but not limited to, a polymeric micelle. Using this approach, the nanoparticulate can be delivered to the target tissue. Methods to prepare such nanoparticulates are well known to those skilled in the art.

It will be appreciated that when the compound of the present invention is administered in combination with other therapeutic agents normally administered by the inhaled, intravenous, oral or intranasal route, that the resultant pharmaceutical composition may be administered by the same routes.

A therapeutically effective amount of a compound of the present invention will depend upon a number of factors including, for example, the age and weight of the animal, the precise condition requiring treatment and its severity, the particular compound having Formula I, the nature of the formulation, and the route of administration, and will ultimately be at the discretion of the attendant physician or veterinarian. However, an effective amount of a compound of Formula I for the treatment of diseases or conditions associated with inappropriate IDO1 protein, will generally be in the range of 5 μg to 100 mg/kg body weight of recipient (mammal) per day and more usually in the range of 5 μg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula I per se.

In general parenteral administration requires lower dosages than other methods of administration which are more dependent upon absorption. However, a dosage for humans preferably contains 0.0001-25 mg of a compound of Formula I or pharmaceutically acceptable salts thereof per kg body weight. The desired dose may be presented as one dose or as multiple sub-doses administered at appropriate intervals throughout the day, or, in case of female recipients, as doses to be administered at appropriate daily intervals throughout the menstrual cycle. The dosage, as well as the regimen of administration, may differ between a female and a male recipient.

The present invention also relates to a pharmaceutical composition comprising a compound of Formula I or pharmaceutically acceptable salt thereof in a mixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition comprising at least one compound of Formula I or pharmaceutically acceptable salts thereof in combination with at least one other therapeutically active agent.

For the treatment of cancer a compound of Formula I may be combined with one or more anticancer agents. Examples of such agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved.

The 3-hydroxyimidazolidin-4-one derivatives of the present invention can be prepared by methods well known in the art of organic chemistry. See, for example, J. March, '*Advanced Organic Chemistry*' 4th Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' 3rd Edition, John Wiley and Sons, 1999. The protective groups are optionally removed at a convenient subsequent stage using methods well known in the art.

The products of the reactions are optionally isolated and purified, if desired, using conventional techniques, including but not limited to, filtration, distillation, crystallization, chromatography and the like. Such materials are optionally characterized using conventional means, including physical constants and spectral data.

3-Hydroxyimidazolidin-4-one compounds of Formula I, wherein $R^1$ to $R^5$ and A have the previously defined meanings, can be prepared by the general synthetic route shown in scheme I.

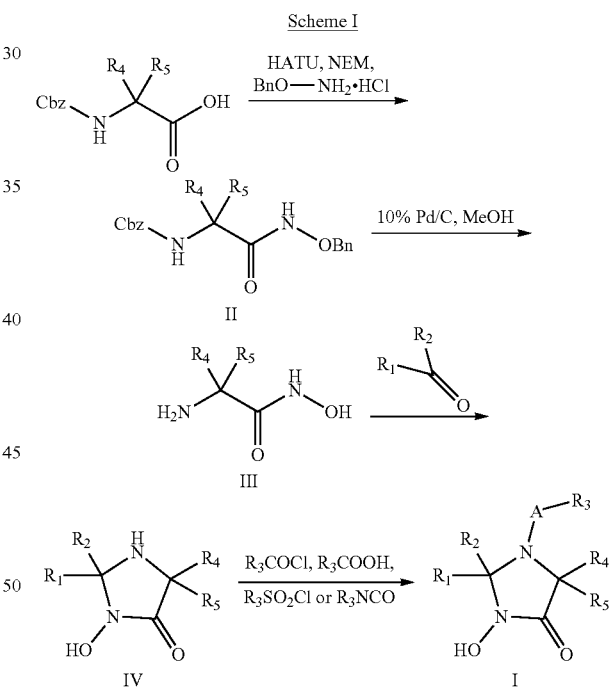

Substituted benzyl N-[2-(benzyloxyamino)-2-oxo-ethyl] carbamate (II) can be prepared from commercial available Cbz-protected amino acids and O-benzylhydroxylamine using an appropriate coupling reagent like HATU or EDCl-hydrochloride in a solvent such as DMF, dichloromethane or THF at appropriate temperature. Derivatives III can subsequently be prepared from derivatives II under catalytic hydrogenation conditions in the presence of a suitable palladium catalyst and solvent. Cyclisation towards derivatives IV can be accomplished by condensation reactions of derivatives III with aldehydes or ketones under heating conditions. Finally conversion of derivatives IV to compounds with formula I can be accomplished using methods well known in the art. The reagents R₃—COCl, R₃COOH, R₃SO₂Cl or R₃NCO are either commercially available or they can be readily prepared using methods known to skilled organic chemists.

Alternatively 3-hydroxyimidazolidin-4-one compounds of Formula I, wherein $R^1$ to $R^5$ and A have the previously defined meanings, can be prepared by the general synthetic route shown in scheme II.

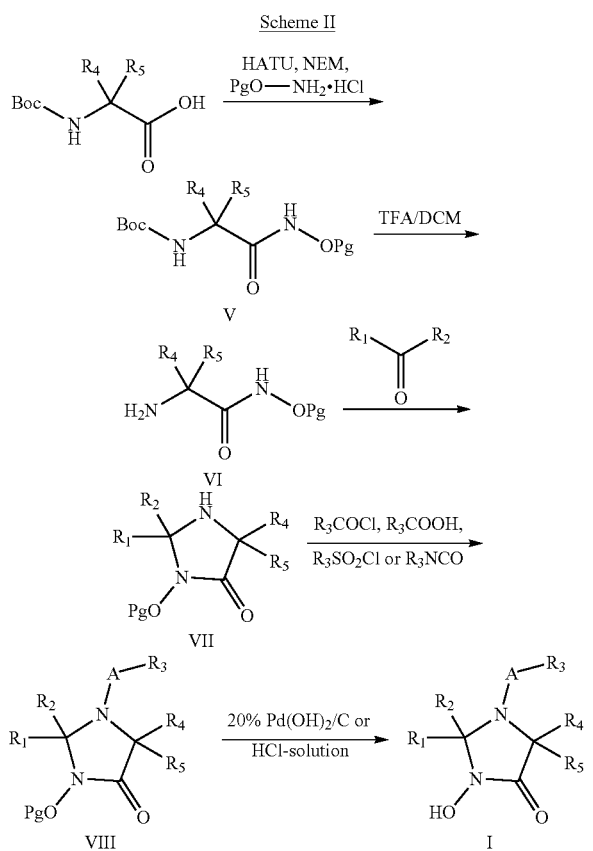

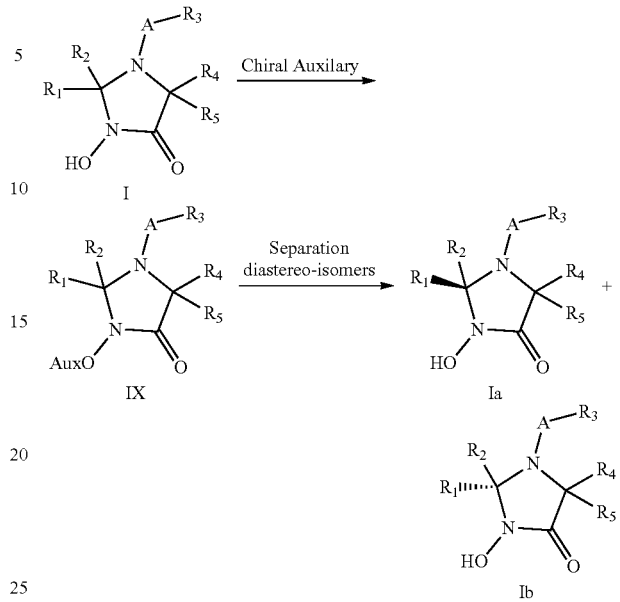

Commercially available Boc-protected amino acids can be converted into the corresponding O-benzyl protected hydroxamic acid derivatives V with an appropriate couplings reagent such as HATU or EDCl.hydrochloride and O-benzyl protected hydroxyl amine in a suitable solvent like DCM or DMF at appropriate temperature. Cleaving the protective group of derivatives V using TFA in dichloromethane give the unprotected amines VI which provided derivatives VII, after condensation with aldehydes or ketones in appropriate solvents such as DCM, acetonitrile or ethanol under heating conditions. Conversion of derivatives VII to compounds VIII can be accomplished using methods well known in the art. The reagents R₃—COCl, R₃COOH, R₃SO₂Cl or R₃NCO are either commercially available or they can be readily prepared using methods known to skilled organic chemists. Compounds of formula I can subsequently be prepared under catalytic hydrogenation conditions in the presence of a suitable palladium catalyst and solvent.

Separation of the enantiomeric 3-hydroxyimidazolidin-4-one compounds of Formula I, wherein $R^1$ to $R^5$ and A have the previously defined meanings, can be performed using chiral HPLC or prepared by the general synthetic route using chiral auxiliaries as shown in scheme III.

Chiral auxiliaries were reacted with compounds with formula I, to obtain derivatives IX by methods known to skilled organic chemists. Chiral acid chlorides such as Mosher's acid chloride or chiral alcohols could be introduced and the thus obtained mixtures of diastereoisomers IX could be separated using chromatographic techniques such as chiral HPLC. After cleavage of the auxiliaries with suitable deprotection agents compounds of formula 1a and 1b could be isolated.

Alternatively 3-hydroxyimidazolidin-4-one compounds of Formula I, wherein $R^1$ to $R^5$ and A have the previously defined meanings, can be prepared by the general synthetic route shown in scheme II.

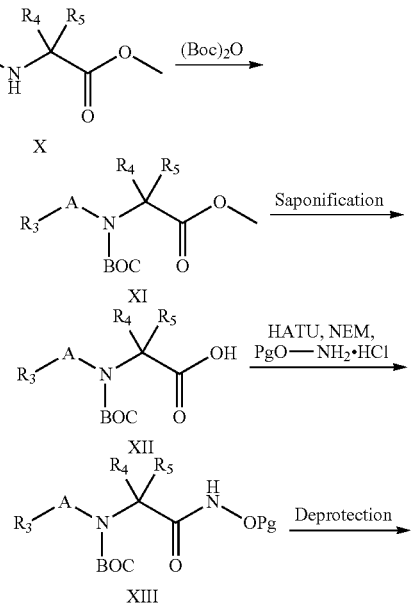

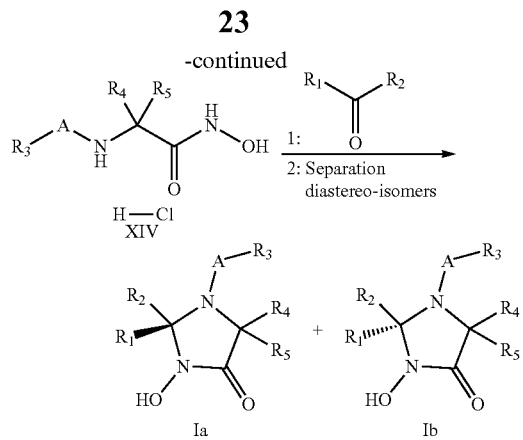

Commercially available amino acid methylesters were converted either via alkylation or reductive amination into starting material X. After protection of the amine-function of derivatives X using di-tert-butyldicarbonate to obtain derivatives XI, saponification with sodiumhydroxide- or lithiumhydroxide-solution could be performed to obtain Boc-protected amino-acid derivatives XII. These can be converted into the corresponding OTHP-protected hydroxamic acid derivatives XIII with an appropriate couplings reagent such as HATU or EDCI.hydrochloride and O-(tetrahydropyran-2-yl)hydroxylamine in a suitable solvent like DCM or DMF at appropriate temperature. Cleaving the protective group of derivatives V using 4M HCl/dioxane provided the hydrochloride salts of the unprotected amines XIV. After condensation with aldehydes or ketones in appropriate solvents such as DCM, acetonitrile or ethanol under heating conditions diastereoisomeric mixtures of derivatives I were obtained. The thus obtained mixtures of diastereoisomers Ia and Ib could be separated using chromatographic techniques such as HPLC.

The invention is illustrated by the following examples.

EXAMPLES

The following examples are illustrative embodiments of the invention, not limiting the scope of the invention in any way. Reagents are either commercially available or are prepared according to procedures known in the literature.

| Method LCMS (A) | |
|---|---|
| Method name | NTRC_C18_Short.M |
| Column | Waters XTerra C18-MS, 50 × 4.6 mm ID, 2.5 μm |
| Flow | 0.5 ml/min. |
| Temperature | 40° C. |
| Detector DAD | 210, 254, 280 nm |
| Detector MSD | API-ES |

| MSD signal | 1 | 2 |
|---|---|---|
| Mode | Scan | Scan |
| Polarity | Positive | Negative |
| Mass Range | 100-1000 m/z | 100-1000 m/z |
| Fragmentor | 70 | 70 |
| Cycle Time | 50% | 50% |

| | | |
|---|---|---|
| Sample preparation | N/A | |
| Concentration | 1 mg/ml in MeOH or ACN | |
| Injection volume | 1.0 μl | |

| Method LCMS (A) | | |
|---|---|---|
| | Eluent | |
| | A | B |
| Time [min] | % 0.1% Formic Acid | % 0.05% Formic Acid in Acetonitrile |
| 0 | 90 | 10 |
| 0.3 | 90 | 10 |
| 7.0 | 10 | 90 |
| 7.1 | 90 | 10 |
| 10.0 | 90 | 10 |
| Post time | 0.2 min | Stop time 10 min |

| Method LCMS (B) | |
|---|---|
| Method LCMS (B) Method name | NTRC_C18.M |
| Column | Waters XTerra C18-MS, 50 × 4.6 mm ID, 2.5 μm |
| Flow | 0.5 ml/min. |
| Temperature | 40° C. |
| Detector DAD | 210, 254, 280 nm |
| Detector MSD | API-ES |

| MSD signal | 1 | 2 |
|---|---|---|
| Mode | Scan | Scan |
| Polarity | Positive | Negative |
| Mass Range | 100-1000 m/z | 100-1000 m/z |
| Fragmentor | 70 | 70 |
| Cycle Time | 50% | 50% |

| | | |
|---|---|---|
| Sample preparation | N/A | |
| Concentration | 1 mg/ml in MeOH or ACN | |
| Injection volume | 1.0 μl | |

| | Eluent | |
|---|---|---|
| | A | B |
| Time [min] | % 0.1% Formic Acid | % 0.05% Formic Acid in Acetonitrile |
| 0 | 90 | 10 |
| 1 | 90 | 10 |
| 22.0 | 10 | 90 |
| 22.1 | 90 | 10 |
| 30.0 | 90 | 10 |
| Post time | 0.2 min | Stop time 30 min |

| Method Preparative HPLC | | | | |
|---|---|---|---|---|
| LC System | Waters Prep System | | | |
| Column | Phenomenex Luna, C18(2) 100 A, 150 mm × 21.2 mm, 5 μm | | | |
| Column Temp | 20° C. | | | |
| Sample(s) | 10-50 mg | | | |
| Autosamp. Temp | 20° C. | | | |
| Injection volume | 500-950 μL | | | |
| Flow | 15 ml/min | | | |
| Eluent | A = MilliQ + MeCN (9/1) B = Acetonitrile | | | |
| Gradient | time (min) | % A | % B | % C |
| | 0 | 97 | 0 | 3 |
| | 20 | 37 | 60 | 3 |
| | 25 | 37 | 60 | 3 |

| Method Preparative HPLC | | | | |
|---|---|---|---|---|
| | 25.1 | 97 | 0 | 3 |
| | 30 | 97 | 0 | 3 |
| UV detection | Photo Diode Array | | | |

The following abbreviations are used throughout the application with respect to chemical terminology:
HATU 0-(7-Azabenzotriazol-1-yl)-1,1,3,3-tetramethyluroniumhexafluorophosphate
DCM Dichloromethane
EDCl.HCl N-(3-Dimethylaminopropyl)-N'-ethylcarbodiimide hydrochloride
NEM 4-Ethylmorpholine
DiPEA N, N-Diisopropylethylamine
HPLC High Performance Liquid Chromatography
LCMS Liquid Chromatography with Mass Spectrometry detection
HCl Hydrogen chloride
NaHCO$_3$ Sodium bicarbonate
Boc tert-Butyloxycarbonyl
Cbz Benzyloxycarbonyl
Gly Glycine
DMSO Dimethyl sulfoxide
DMEM Dulbecco's Modified Eagle's Medium
TFA Trifluoroacetic acid
EtOAc Ethyl acetate
LiOH Lithium hydroxide
Na$_2$SO$_4$ Sodium sulfate
PdCl$_2$(dppf) [1,1'-Bis(diphenylphosphino)ferrocene]dichloropalladium(II)
DMF N,N-Dimethylformamide
THF Tetrahydrofuran
MeOH Methanol
NaOH Sodium hydroxide
BF3.Et2O Boron trifluoride ethyl etherate
LDA Lithium diisopropylamide
Pd(PPh$_3$)$_4$ Tetrakis(triphenylphosphine)palladium(0)

The names of the final products in the examples are generated using Accelrys Draw (version 4.1).

Intermediate 1

2-Aminoethanehydroxamic acid (a) Benzyl N-[2-(benzyloxyamino)-2-oxo-ethyl]carbamate To a cold solution (0° C.) of Cbz-Gly-OH (2.75 g, 13.2 mmol) and O-benzylhydroxylamine hydrochloride (2.1 g, 13.2 mmol) in ethyl acetate/DMF=5/1 v/v % (132 mL) was added DiPEA (6.53 mL, 39.5 mmol) and EDCl.HCl (2.57 g, 13.4 mmol), after which the reaction mixture was allowed to warm to room temperature and stirred for 3 days. After TLC indicated a complete conversion of starting material the mixture was added dropwise to a stirred solution of water/brine=1/1 v/v % (250 mL). After separation of the organic and the water layers, the water layer was extracted with ethyl acetate (2×150 mL). The combined organic layers were subsequently washed with a solution of 1N HCl (100 mL), water (100 mL), 5% sodium bicarbonate (100 mL), water and brine. The organic layer was subsequently dried over sodium sulfate and concentrated in vacuo to give 2.93 g of N-[2-(benzyloxyamino)-2-oxo-ethyl]carbamate (yield: 71%).

(b) 2-Aminoethanehydroxamic acid

10% Palladium on charcoal (700 mg) was added to a suspension of benzyl N-[2-(benzyloxyamino)-2-oxo-ethyl] carbamate (7 g, 22.3 mmol) in methanol/ethyl acetate=3/1 v/v% (400 mL). The mixture was hydrogenated at atmospheric pressure at room temperature for 2 h. The palladium catalyst was removed by filtration and the solvent was removed by evaporation at reduced pressure. The residue was dissolved in water and lyophilized yielding 2-aminoethanehydroxamic acid (4.3 g, 77%) as a white powder.

Intermediate 2

2-(4-Bromo-2-thienyl)-3-hydroxy-imidazolidin-4-one

2-Aminoethanehydroxamic acid (Intermediate 1, 95.4 mg, 1.06 mmol) and 4-bromothiophene-2-carbaldehyde (212 mg, 1.11 mmol) were suspended in absolute ethanol (1.9 mL). The mixture was heated to reflux for 1 h to give a yellow solution. The reaction mixture was cooled to room temperature and stirred overnight. The solids formed were filtered, washed with ethanol and dried under vacuum to give 34 mg of the title compound (yield: 12%). The filtrate was subsequently concentrated in vacuo. The residue was dissolved in dichloromethane and the precipitate formed was collected by filtration to give a second crop of 154 mg of 2-(4-bromo-2-thienyl)-3-hydroxy-imidazolidin-4-one as a light yellow solid (yield: 55%).

Intermediate 3

2-(4-Ethynyl-2-thienyl)-3-hydroxy-imidazolidin-4-one

This compound was prepared in an analogous manner as described for Intermediate 2, starting from 2-aminoethanehydroxamic acid (Intermediate 1) and 4-ethynylthiophene-2-carbaldehyde (prepared according to Nishi et al, WO2006/115188A1) to afford the title compound (74 mg, 89%).

Intermediate 4

3-Hydroxy-2-(4-iodo-2-thienyl)imidazolidin-4-one

This compound was prepared in an analogous manner as described for Intermediate 2, starting from 2-aminoethanehydroxamic acid (Intermediate 1) and 4-iodothiophene-2-carbaldehyde (prepared according to Basarab et al, WO2005/111001A1) to afford the title compound (334 mg, 53%).

Intermediate 5

4-Ethynyl-2,6-difluoro-benzoic acid (a) Methyl 4-bromo-2,6-difluoro-benzoate

Thionylchloride (6.12 mL, 84.4 mmol) was added dropwise to dry methanol (100 mL) at −20° C. 4-Bromo-2,6-difluorobenzoic acid (10 g, 42.2 mmol)) was added and the reaction mixture was heated under reflux o/n. The mixture was concentrated in vacuo and traces of hydrochloric acid were co-evaporated with methanol (3 times). The residue crystallized upon standing giving 11.8 g of the title compound.

(b) Methyl 2,6-difluoro-4-(2-trimethylsilylethynyl)benzoate

4-Bromo-2,6-difluoro-benzoic acid methyl ester (250 mg, 1 mmol) was dissolved in triethylamine (5 mL) and to this solution dichloropalladium(bis)triphenylphosphine (36 mg, 0.05 mmol) was added followed by copper iodide (10 mg, 0.05 mmol) and trimethylsilylacetylene (170 μL, 1.2 mmol). The reaction mixture was heated for 1 hour at 100° C. under microwave radiation. The mixture was cooled to room temperature and filtered through Decalite™ and concentrated under reduced pressure. The crude residue was purified by column chromatography (heptane to ethyl acetate=9/1 v/v %) to afford 293.6 mg of the title compound (quantitative yield).

(c) 4-Ethynyl-2,6-difluoro-benzoic acid (Intermediate 5)

Methyl 2,6-difluoro-4-(2-trimethylsilylethynyl)benzoate (293.6 mg, 1.09 mmol) was dissolved in methanol (5 mL) and 5 mL of a 2M LiOH-solution in water. The mixture was refluxed overnight, after which methanol was removed by evaporation in vacuo and the resulting solution was extracted with EtOAc, acidified, and again extracted with EtOAc. The organic layers were washed with brine, dried (Na$_2$SO$_4$), filtered and concentrated under vacuum to give the title compound (154.7 mg, 77.9%).

Intermediate 6

4-(2-Cyclopropylethynyl)-2,6-difluoro-benzoic acid (a) Methyl 4-(2-cyclopropylethynyl)-2,6-difluoro-benzoate 4-Bromo-2,6-difluoro-benzoic acid methyl ester (Intermediate 5a, 250 mg, 1 mmol) was dissolved in triethylamine (5 mL) and dichloropalladium(bis)triphenylphosphine (36 mg, 0.05 mmol) was added followed by copper iodide (10 mg, 0.05 mmol) and cyclopropylacetylene (85 μL, 1.2 mmol). The reaction mixture was heated for 1 hour at 100° C. under microwave radiation. The mixture was cooled to room temperature and filtered through Decalite™ and concentrated under reduced pressure. The crude residue was purified by column chromatography (heptane to ethyl acetate=9/1 v/v %) to afford 214 mg of the title compound (yield: 90.6%).

(b) 4-(2-Cyclopropylethynyl)-2,6-difluoro-benzoic acid (Intermediate 6)

Methyl 4-(2-cyclopropylethynyl)-2,6-difluoro-benzoate (214 mg, 0.91 mmol) was dissolved in methanol (5 mL) and 5 mL of a 2M LiOH-solution in water and the mixture was refluxed overnight. Methanol was removed by concentration in vacuo and the resulting solution was extracted with EtOAc, acidified, and again extracted with EtOAc. The organic layers were washed with brine, dried (Na$_2$SO$_4$), filtered and concentrated under vacuum to give the title compound (193.5 mg, 96.0%).

Intermediate 7

2,6-Difluoro-4-(3-methylbut-1-ynyl)benzoic acid (a) Methyl 2,6-difluoro-4-(3-methylbut-1-ynyl)benzoate 4-Bromo-2,6-difluoro-benzoic acid methyl ester (Intermediate 5a, 502 mg, 2 mmol) was dissolved in triethylamine (10 mL) and dichloropalladium(bis)triphenylphosphine (70.2 mg, 0.1 mmol) was added followed by copper iodide (19 mg, 0.1 mmol) and 3-methyl-1-butyne (307 μL, 1.5 mmol). The reaction mixture was heated for 1 hour at 100° C. under microwave radiation. The mixture was cooled to room temperature and filtered through Celite® and concentrated in vacuo. The crude residue was purified by column chromatography (heptane to ethyl acetate=100/0 to 9/1 v/v %) to afford 440 mg of the title compound (yield: 92.4%).

(b) 2,6-Difluoro-4-(3-methylbut-1-ynyl)benzoic acid (Intermediate 7)

Methyl 2,6-difluoro-4-(3-methylbut-1-ynyl)benzoate (440 mg, 1.85 mmol) was dissolved in 5 mL of methanol and 5 mL of a 2M LiOH-solution in water. The mixture was stirred at room temperature for 2h, after which the reaction mixture was acidified, and extracted with dichloromethane. The organic layer was washed with brine, dried (Na$_2$SO$_4$), filtered over a PE-filter and concentrated in vacuo to give the title compound (367.8 mg, 88.7%).

Intermediate 8

4-(2-Cyclohexylethynyl)-2,6-difluoro-benzoic acid (a) Methyl 4-(2-cyclohexylethynyl)-2,6-difluoro-benzoate Methyl 4-bromo-2,6-difluoro-benzoate (Intermediate 5a, 502 mg, 2 mmol) was dissolved in N,N-dimethylformamide (5 mL) and triethylamine (1.59 mL, 10 mmol). The solution was purged with nitrogen for 5 min and copper(I)iodide (19 mg, 0.1 mmol) and bis(triphenylphosphine)palladium(II) chloride (70.2 mg, 0.1 mmol) were added. The mixture was stirred for 5 min after which cyclohexylacetylene (1.29 mL, 10 mmol) was added and the reaction mixture was stirred at 80° C. for 2 h. The reaction mixture was added to a stirred mixture of water/brine/ethyl acetate=1/1/1 v/v % (45 mL). The organic layer was separated, washed with water, brine, dried over sodium sulfate, filtered and concentrated under reduced pressure. The crude residue was purified by column chromatography (heptane/ethyl acetate=95/5 v/v %) to afford 360 mg of the title compound (yield: 64.7%).

(b) 4-(2-Cyclohexylethynyl)-2,6-difluoro-benzoic acid (Intermediate 8)

Methyl 4-(2-cyclohexylethynyl)-2,6-difluoro-benzoate (360 mg, 1.29 mmol) was dissolved in methanol (5 mL) and 5 mL of a 2M LiOH-solution in water. The reaction mixture was stirred at room temperature for 2 h, after which the reaction mixture was acidified and extracted with dichloromethane The organic layer was separated and washed with brine, dried (Na$_2$SO$_4$), filtered over a PE-filter and concentrated under reduced pressure to give the title compound (311.1 mg, 91.2%).

Intermediate 9

2,6-Difluoro-4-[3-(methanesulfonamido)prop-1-ynyl]benzoic acid (a) N-prop-2-ynylmethanesulfonamide To a cold (4° C.) solution of propargylamine (0.86 g, 15.6 mmol) and triethylamine (2.39 mL, 17.2 mmol) in dichloromethane (10 mL) was added dropwise a solution of methanesulfonyl chloride (1.52 mL, 15.6 mmol) in dichloromethane (5 mL). The reaction mixture was allowed to warm to room temperature, stirred for 1 h and concentrated in vacuo. The crude residue was purified by column chromatography (heptane to ethyl acetate=8/2 to 1/1 v/v %) to afford 465 mg of the title compound (yield: 22.4%).

(b) 2,6-Difluoro-4-[3-(methanesulfonamido)prop-1-ynyl]benzoic acid (Intermediate 9)

This compound was prepared in an analogous manner as described for Intermediate 8, starting from methyl 4-bromo-2,6-difluoro-benzoate (Intermediate 5a) and N-prop-2-ynyl-methanesulfonamide to afford the title compound (187.7 mg, 57.9%).

Intermediate 10

4-[3-(tert-Butoxycarbonylamino)prop-1-ynyl]-2,6-difluoro-benzoic acid

This compound was prepared in an analogous manner as described for Intermediate 8, starting from methyl 4-bromo-2,6-difluoro-benzoate (Intermediate 5a) and tert-butyl N-prop-2-ynylcarbamate to afford the title compound (185.3 mg, 97.6%).

Intermediate 11

4-[3-(tert-Butoxycarbonylsulfamoylamino)prop-1-ynyl]-2,6-difluoro-benzoic acid (a) tert-Butyl N-(prop-2-ynylsulfamoyl)carbamate To a cold (4° C.) solution of chlorosulfonyl isocyanate (1.63 mL, 18.7 mmol) in dichloromethane (10 mL) was added dropwise a solution of tert-butanol 2.24 mL, 23.4 mmol) in dichloromethane (5 mL). The reaction mixture was stirred for 15 min at 5° C. Triethylamine (4.78 mL, 34.4 mmol) and propargylamine (1 mL, 15.6 mmol) were added subsequently to the reaction mixture and the mixture was allowed to warm to room temperature and stirred for 1 h and subsequently concentrated in vacuo. The crude residue was purified by column chromatography (heptane to ethyl acetate=8/2 to 1/1 v/v %) to afford 2.79 g of the title compound (yield: 76.3%).

(b) 4-[3-(tert-Butoxycarbonylsulfamoylamino)prop-1-ynyl]-2,6-difluoro-benzoic acid (Intermediate 11)

This compound was prepared in an analogous manner as described for Intermediate 8, starting from methyl 4-bromo-2,6-difluoro-benzoate (Intermediate 5a) and tert-butyl N-(prop-2-ynylsulfamoyl)carbamate to afford the title compound (219.6 mg, 59.8%).

Intermediate 12

4-[3-(tert-Butoxycarbonylamino)-3-methyl-but-1-ynyl]-2,6-difluoro-benzoic acid (a) tert-Butyl N-(1,1-dimethylprop-2-ynyl)carbamate A mixture of 2-methyl-3-butyn-2-amine (1 mL) and di-tert-butyl dicarbonate (2.07 g) without solvent was warmed up to 50° C. for 30 min. The resulting solution was diluted with n-hexane (5 mL) and the crystals formed were, subsequently, collected by filtration, washed with hexane and dried under vacuum to give 620 mg of the title compound (yield: 35.6%).

4-[3-(tert-Butoxycarbonylamino)-3-methyl-but-1-ynyl]-2,6-difluoro-benzoic acid (Intermediate 12)

This compound was prepared in an analogous manner as described for Intermediate 8, starting from methyl 4-bromo-2,6-difluoro-benzoate (Intermediate 5a) and tert-butyl N-(1,1-dimethylprop-2-ynyl)carbamate to afford the title compound (608.4 mg, 93.4%).

Intermediate 13

4-Cyclopropyl-2,6-difluoro-benzoic acid (a) Methyl 4-cyclopropyl-2,6-difluoro-benzoate Methyl 4-bromo-2,6-difluoro-benzoate (502 mg, 2 mmol), tricyclohexylphosphine (168 mg, 0.6 mmol), cesium carbonate (3.9 g, 12 mmol) and cyclopropylboronic acid methyliminodiacetic acid anhydride (552 mg, 2.8 mmol) were dissolved in toluene/water=5/1 v/v % (24 mL) and the solution was degassed with nitrogen for 5 minutes. Palladium(II)acetate (67.3 mg, 0.3 mmol) was added under nitrogen atmosphere and the reaction mixture was refluxed at 100° C. for 3 hours. The crude reaction mixture was filtered over Decalite™. The filtrate was diluted with ethyl acetate and washed with water, brine, dried over sodium sulfate, filtered and evaporated under reduced pressure. The crude residue was purified by column chromatography (heptane/ethyl acetate=95/5 v/v %) to afford the title compound (240 mg, yield: 56.6%).

(b) 4-Cyclopropyl-2,6-difluoro-benzoic acid (Intermediate 13)

Methyl 4-cyclopropyl-2,6-difluoro-benzoate (240 mg, 1.13 mmol) was dissolved in methanol (5 mL) and 2M LiOH-solution in water (5 mL) and the mixture was stirred at room temperature for 2 h, after which the reaction mixture was acidified, and extracted with dichloromethane. The organic layer was washed with brine, dried ($Na_2SO_4$), filtered over a PE-filter and concentrated under vacuum to give the title compound (200 mg, 89.3%).

Intermediate 14

2,6-Difluoro-4-vinyl-benzoic acid (a) Methyl 2,6-difluoro-4-vinyl-benzoate

Methyl 4-bromo-2,6-difluoro-benzoate (251 mg, 1.0 mmol) was dissolved in dioxane (5 mL) and potassium carbonate (207 mg, 1.5 mmol) was added. The solution was purged with nitrogen for 5 min and vinylboronic anhydride pyridine complex (240.7 mg, 1.0 mmol) and $PdCl_2(dppf)$.$CH_2Cl_2$ (40.8 mg, 0.05 mmol) were added. The reaction mixture was stirred for 2 h. at 100° C. The reaction mixture was added to a stirred mixture of 5% citric acid solution/brine/ethyl acetate=1/1/1 v/v % (150 mL). The organic layer was separated, washed with water, brine, dried over sodium sulfate, filtered and evaporated under reduced pressure The crude residue was purified by column chromatography (dichloromethane/methanol=98/2 v/v %) to afford two batches of the title compound (174 mg, yield: 87.7%).

(b) 2,6-Difluoro-4-vinyl-benzoic acid (Intermediate 14)

This compound was prepared in an analogous manner as described for Intermediate 13b, starting from methyl 2,6-difluoro-4-vinyl-benzoate to afford the title compound (140.4 mg, 86.7%).

Intermediate 15

2,6-Difluoro-4-methyl-benzoic acid

This compound was prepared in an analogous manner as described for Intermediate 14, starting from methyl 4-bromo-2,6-difluoro-benzoate (Intermediate 5a) and trimethylboroxine to afford the title compound (468 mg, 84.2%).

Intermediate 16

2,6-Difluoro-4-phenyl-benzoic acid

Methyl 4-bromo-2,6-difluoro-benzoate (300 mg, 1.2 mmol) was dissolved in dioxane/water=4/1 v/v % (10 mL) and sodium carbonate (382 mg, 3.6 mmol) was added. The solution was purged with nitrogen for 5 min and phenylboronic acid (161 mg, 1.3 mmol) and Pd(PPh$_3$)$_4$ (69 mg, 0.06 mmol) were added. The reaction mixture was stirred for 1 h at 100° C. under microwave radiation. The reaction mixture was cooled and a 2M NaOH-solution in water was added (4 mmol). The mixture was stirred for 1 h at 50° C. Ethyl acetate (10 mL) was added and the aqueous layer was separated. The organic layer was extracted twice with 2M NaOH-solution in water. The pH of the water layers was adjusted to pH<2 and the acidic water layer was extracted with ethyl acetate. The ethyl acetate layers were collected and washed with brine, dried over sodium sulfate, filtered and concentrated in vacuo. The crude product was triturated with heptane/ethyl acetate=7/3 v/v %. White solids formed were collected by filtration, washed with heptane and dried under vacuum to give 108 mg of the title compound (yield: 38%).

Intermediate 17

2,6-Difluoro-4-(1-methylpyrazol-4-yl)benzoic acid

This compound was prepared in an analogous manner as described for Intermediate 16, starting from methyl 4-bromo-2,6-difluoro-benzoate (Intermediate 5a) and 1-methyl-4-(4,4,5,5-tetramethyl-1,3,2-dioxaborolan-2-yl)-1H-pyrazole to afford 86 mg of the title compound (yield: 60%).

Intermediate 18

2,6-Difluoro-4-(2-thienyl)benzoic acid

This compound was prepared in an analogous manner as described for Intermediate 16, starting from methyl 4-bromo-2,6-difluoro-benzoate (Intermediate 5a) and 2-(4,4,5,5-tetramethyl-1,3,2-dioxaborolan-2-yl)thiophene to afford 74 mg of the title compound (yield: 51%).

Intermediate 19

2,6-Difluoro-4-(3-pyridyl)benzoic acid

This compound was prepared in an analogous manner as described for Intermediate 16, starting from methyl 4-bromo-2,6-difluoro-benzoate (Intermediate 5a) and pyridine-3-boronic acid 1,3-propanediol cyclic ester to afford 65 mg of the title compound (yield: 34%).

Intermediate 20

4-[2-[1-(tert-Butoxycarbonylamino)cyclopropyl]ethynyl]-2,6-difluoro-benzoic acid This compound was prepared in an analogous manner as described for Intermediate 8 and Intermediate 11a, starting from methyl 4-bromo-2,6-difluoro-benzoate (Intermediate 5a) and tert-butyl N-(1-ethenylcyclopropyl)carbamate to afford the title compound (800 mg, quantitative).

Intermediate 21

4-[2-[1-(tert-Butoxycarbonylsulfamoylamino)cyclopropyl]ethynyl]-2,6-difluoro-benzoic acid This compound was prepared in an analogous manner as described for Intermediate 8 and Intermediate 11a, starting from methyl 4-bromo-2,6-difluoro-benzoate (Intermediate 5a) and tert-butyl N-[(1-ethenylcyclopropyl)sulfamoyl]carbamate to afford 74 mg of the title compound (yield: 51%).

Intermediate 22

2,6-Difluoro-4-(methanesulfonamidomethyl)benzoic acid (a) tert-Butyl 4-bromo-2,6-difluoro-benzoate 4-Bromo-2,6-difluorobenzoic acid (1.5 g, 6.33 mmol) was suspended in dichloromethane (10 mL). A solution of tert-butyl 2,2,2-trichloroacetimidate (1.38 g, 6.33 mmol) in cyclohexane (30 mL) and BF$_3$.Et$_2$O (47.5 µL, 0.38 mmol) were added subsequently to the suspension. After stirring at room temperature for 16 h, the reaction was cooled on an ice bath and solid NaHCO$_3$ (0.5 g) was added in one portion. This mixture was stirred for 10 min and filtered over a silica plug. The filtrate was concentrated in vacuo and the residue was purified by column chromatography (heptane/ethyl acetate=7/3 v/v %) to provide the title compound as a colourless oil (1.43 g, 77.1%).

(b) tert-Butyl 4-cyano-2,6-difluoro-benzoate

To a solution of tert-butyl 4-bromo-2,6-difluoro-benzoate (1.4 g, 4.78 mmol) in DMF (10 mL) were added zinc cyanide (561 mg, 4.78 mmol), and Pd(PPh$_3$)$_4$ (552 mg, 0.48 mmol). The reaction mixture was refluxed at 80° C. under nitrogen atmosphere o/n. The reaction mixture was added to a stirred mixture of 5% NaHCO$_3$-solution/brine/ethyl acetate=1/1/1 v/v % (150 ml). The organic layer was separated, washed with water, brine, dried over sodium sulfate, filtered and evaporated under reduced pressure. The crude residue was purified by column chromatography (heptane/ethyl acetate=100/0 to 95/5 v/v %) to afford 810 mg of the title compound (yield: 70.8%).

(c) tert-Butyl 4-(aminomethyl)-2,6-difluoro-benzoate hydrochloride

10% Palladium on charcoal (20 mg) and 420 µL of a 2N hydrochloride solution were added to a solution of tert-butyl 4-cyano-2,6-difluoro-benzoate (200 mg, 0.84 mmol) in ethanol (20 mL). The mixture was hydrogenated at atmospheric pressure at room temperature for 3 h. The palladium catalyst was removed by filtration and the solvent was removed by evaporation at reduced pressure yielding tert-butyl 4-(aminomethyl)-2,6-difluoro-benzoate hydrochloride quantitatively.

(d) tert-Butyl 2,6-difluoro-4-(methanesulfonamidomethyl)benzoate

To a suspension of tert-butyl 4-(aminomethyl)-2,6-difluoro-benzoate hydrochloride (200 mg, 0.84 mmol) in DCM (10 mL) was added triethylamine (240 µL, 1.68 mmol) and methanesulfonyl chloride (65 µL, 0.84 mmol). The mixture was stirred at room temperature o/n. Mixture was concentrated under reduced pressure and the crude residue was purified by column chromatography (dichloromethane/methanol=98/2 to 96/4 v/v %) to afford 113.7 mg of the title compound (yield: 42.1%).

(e) 2,6-Difluoro-4-(methanesulfonamidomethyl)benzoic acid (Intermediate 22)

To a solution of 2,6-difluoro-4-(methanesulfonamidomethyl)benzoic acid (113.7 mg, 0.35 mmol) in dichloromethane (2 mL) was added trifluoroacetic acid (2 mL). The reaction mixture was stirred at room temperature for 4 h. The mixture was concentrated in vacuo and co-evaporated with dichloromethane (3×) to give the title compound in quantitative crude yield.

Intermediate 23

4-(2-Cyclohexylethyl)-2,6-difluoro-benzoic acid

10% Palladium on charcoal (20 mg) was added to a solution of 4-(2-cyclohexylethynyl)-2,6-difluoro-benzoic acid (Intermediate 8, 125 mg, 0.47 mmol) in methanol (10 mL). The mixture was hydrogenated at atmospheric pressure at room temperature for 5 h. The palladium catalyst was removed by filtration and the solvent was removed by evaporation at reduced pressure yielding 4-(2-cyclohexylethyl)-2,6-difluoro-benzoic acid quantitatively.

Intermediate 24

4-[3-(tert-Butoxycarbonylsulfamoylamino)propyl]-2,6-difluoro-benzoic acid

(a) Methyl 4-[3-(tert-butoxycarbonylsulfamoylamino)propyl]-2,6-difluoro-benzoate 10% Palladium on charcoal (30 mg) was added to a solution of methyl 4-[3-(tert-butoxycarbonylsulfamoylamino)prop-1-ynyl]-2,6-difluoro-benzoate (Intermediate 11b, 300 mg, 0.74 mmol) in methanol (10 mL). The mixture was hydrogenated at atmospheric pressure at room temperature for 5 h. The palladium catalyst was removed by filtration and the solvent was removed by evaporation at reduced pressure to give 273.1 mg of methyl 4-[3-(tert-butoxycarbonylsulfamoylamino)propyl]-2,6-difluoro-benzoate (yield: 90.4%).

(b) 4-[3-(tert-Butoxycarbonylsulfamoylamino)propyl]-2,6-difluoro-benzoic acid (Intermediate 24)

Methyl 4-[3-(tert-butoxycarbonylsulfamoylamino)propyl]-2,6-difluoro-benzoate (273.1 mg, 0.69 mmol) was dissolved in methanol (5 mL) and 2M LiOH-solution (3.3 ml) and the mixture was stirred at room temperature for 2 h. The basic layer acidified, and extracted with dichloromethane. The organic layer was washed with brine, dried ($Na_2SO_4$), filtered over a PE-filter and concentrated in vacuo to give the title compound (223.2 mg, 82.1%).

Intermediate 25

Mixture of 2,6-difluoro-4-[3-methylbut-1-enyl]benzoic acid and 2,6-difluoro-4-isopentyl-benzoic acid 25% Palladium on calciumcarbonate (5 mg) was added to a solution of 2,6-difluoro-4-(3-methylbut-1-ynyl)benzoic acid (Intermediate 7, 50 mg, 0.22 mmol) in ethyl acetate (10 mL). The mixture was hydrogenated at atmospheric pressure at room temperature for 40 min. The palladium catalyst was removed by filtration and the solvent was removed by evaporation at reduced pressure yielding a 7:3 mixture of 2,6-difluoro-4-(3-methylbut-1-enyl)benzoic acid and 2,6-difluoro-4-isopentyl-benzoic acid.

Intermediate 26

4-(1-tert-Butoxycarbonylpyrazol-4-yl)-2,6-difluorobenzoic acid

This compound was prepared in an analogous manner as described for Intermediate 11, starting from methyl 4-bromo-2,6-difluoro-benzoate (Intermediate 5a) and 1-Boc-pyrazole-4-boronic acid pinacol ester to afford 53 mg of the title compound (yield: 27%).

Intermediate 27

4-(Dimethylamino)-2,6-difluoro-benzoic acid

(a) Methyl 4-(dimethylamino)-2,6-difluoro-benzoate

To a solution of methyl 2,4,6-trifluorobenzoate (679 µL, 5 mmol) and N-methylmethanamine hydrochloride (489 mg, 6 mmol) in DMSO (10 mL) was added potassium carbonate (1.52 g, 11 mmol) and the reaction mixture was stirred at 55° C. o/n. Ethyl acetate was added to the mixture and the mixture was washed with water, brine, dried over sodium sulfate, filtered and the solvent was removed by evaporation at reduced pressure. The crude residue was purified by column chromatography (heptane/ethyl acetate=10/0 to 1/1 v/v %) to afford 395 mg of the title compound (yield: 37%).

(b) 4-(Dimethylamino)-2,6-difluoro-benzoic acid (Intermediate 27)

This compound was prepared in an analogous manner as described for Intermediate 24b, starting with methyl 4-(dimethylamino)-2,6-difluoro-benzoate to afford the title compound (292 mg, 80%).

Intermediate 28

2-(5-Bromo-3-thienyl)-3-hydroxy-imidazolidin-4-one

This compound was prepared in an analogous manner as described for Intermediate 2, starting from 2-aminoethanehydroxamic acid (Intermediate 1) and 5-bromothiophene-3-carbaldehyde to afford the title compound (360 mg, 63%).

Intermediate 29

2-(4-Bromo-5-deuterio-2-thienyl)-3-hydroxy-imidazolidin-4-one

(a) 2-(4-Bromo-5-deuterio-2-thienyl)-1,3-dioxolane

To a cold (−78° C.) solution of 2-(4-bromo-2-thienyl)-1,3-dioxolane (862 mg, 3.67 mmol) in THF (15 mL) was added drop-wise LDA (2M in THF/hexane, 4.07 mL, 8.14 mmol) keeping the temperature below −70° C. to give a yellow/orange solution. The reaction mixture was stirred 60 min at −78° C. and another 30 min at 0° C. The mixture was cooled to −78° C. and deuterium oxide (500 µL) was added. The mixture was diluted with water and extracted with ethyl acetate. The combined organic layers were washed with water, 5% $NaHCO_3$-solution, brine, dried ($Na_2SO_4$), filtered and concentrated under reduced pressure. The crude residue was purified by column chromatography (heptane to ethyl acetate=10/0 to 1/4 v/v %) to give 700 mg of the title compound (yield: 81%).

(b) 4-Bromo-5-deuterio-thiophene-2-carbaldehyde

To a solution of 2-(4-bromo-5-deuterio-2-thienyl)-1,3-dioxolane (700 mg, 2.97 mmol) in THF (15 mL) was added 1M HCl-solution (15 mL) and the reaction mixture was stirred for 1 h. at room temperature. The mixture was extracted with ethyl acetate. The combined organic layers were washed with water, brine, dried ($Na_2SO_4$), filtered and concentrated under reduced pressure to give 540 mg of the title compound (Yield: 95%).

(c) 2-(4-Bromo-5-deuterio-2-thienyl)-3-hydroxy-imidazolidin-4-one (Intermediate 29)

This compound was prepared in an analogous manner as described for Intermediate 2, starting from 2-aminoethanehydroxamic acid (Intermediate 1) and 4-bromo-5-deuterio-thiophene-2-carbaldehyde to afford the title compound (173 mg, 55%).
Intermediate 30

4-Bromo-5-methyl-thiophene-2-carbaldehyde

This compound was prepared in an analogous manner as described for Intermediate 29, starting from 2-(4-bromo-2-thienyl)-1,3-dioxolane and iodomethane to afford the title compound (597 mg, 94%).
Intermediate 31

4-bromo-5-(trideuteriomethyl)thiophene-2-carbaldehyde

This compound was prepared in an analogous manner as described for Intermediate 29, starting from 2-(4-bromo-2-thienyl)-1,3-dioxolane and iodomethane-d3 to afford the title compound (129 mg, 93%).
Intermediate 32

2-[[(1S)-1-phenylethyl]amino]ethanehydroxamic acid hydrochloride (a) Methyl 2-[[(1S)-1-phenylethyl]amino]acetate To a solution of (1S)-1-phenylethylamine (500 mg, 3.9 mmol) in acetonitrile (20 mL) was added methyl bromoacetate (371 µL, 3.9 mmol) and potassium carbonate (1.08 g, 7.8 mmol). The reaction mixture was stirred o/w at room temperature. The mixture was filtered and the filtrate was concentrated under vacuum to give the crude tile compound (703 mg, 93%). (11) Methyl 2-[tert-butoxycarbonyl-[(1S)-1-phenylethyl]amino]acetate
To a solution of methyl 2-[[(1S)-1-phenylethyl]amino]acetate (703 mg, 3.64 mmol) in water (15 mL) was added a solution of di-tert-butyl dicarbonate (1.19 g, 5.46 mmol) in dioxane (3 mL) and the mixture was stirred at room temperature for 3 h. The mixture was extracted with ethyl acetate. The organic layer was separated and washed with water, brine, dried ($Na_2SO_4$), filtered and concentrated under reduced pressure to give methyl 2-[tert-butoxycarbonyl-[(1S)-1-phenylethyl]amino]acetate in quantitative yield.

(c) 2-[tert-Butoxycarbonyl-[(1S)-1-phenylethyl]amino]acetic acid

To a solution of methyl 2-[tert-butoxycarbonyl-[(1S)-1-phenylethyl]amino]acetate (1.3 g, 3.87 mmol) in THF/MeOH=3/1 v/v % (40 mL) was added 1M LiOH-solution (10 mL) and the reaction mixture was stirred at room temperature o/n. Cold water was added to the mixture and 5% citric acid solution was added until pH<3. Ethyl acetate was added and after stirring, the organic phase was separated, washed with water, brine, dried ($Na_2SO_4$), filtered and concentrated under reduced pressure to give the 947 mg of the title compound (Yield: 88%).

(d) tert-Butyl N-[2-oxo-2-(tetrahydropyran-2-yloxyamino)ethyl]-N-[(1S)-1-phenylethyl]carbamate To a solution of 2-[tert-butoxycarbonyl-[(1S)-1-phenylethyl]amino]acetic acid (905 mg, 3.24 mmol) and O-tetrahydropyran-2-ylhydroxylamine (456 mg, 3.89 mmol) in DCM (25 mL) and DMF (4 mL) was added HATU (1.48 g, 3.89 mmol) and N-ethylmorpholine (1.23 mL, 9.7 mmol) and the reaction mixture was stirred for 30 min at rt. The reaction mixture was stopped by adding it dropwise to a mixture of water:brine (1/1 v/v %, 50 mL) and stirring the mixture for 15 min. EtOAc was subsequently added to the mixture and the organic layer was separated and washed with 5% citric acid solution and brine, dried ($Na_2SO_4$), filtered and concentrated to give 1.68 g of the title compound (Yield: 99%).

(e) tert-Butyl N-[2-(hydroxyamino)-2-oxo-ethyl]-N-[(1S)-1-phenylethyl]carbamate

To a solution of tert-butyl N-[2-oxo-2-(tetrahydropyran-2-yloxyamino)ethyl]-N-[(1S)-1-phenylethyl]carbamate (1.64 g, 3.24 mmol) in methanol (25 mL) was added p-toluenesulfonic acid monohydrate (1.23 g, 6.48 mmol) and the reaction mixture was stirred for 1 h at room temperature. Dichloromethane (225 mL) was added and the mixture was washed with 5% $NaHCO_3$-solution, water, brine, dried over sodium sulfate, filtered and concentrated under reduced pressure. The crude residue was purified by column chromatography (heptane to ethyl acetate=10/0 to 1/3 v/v %) to afford 775 mg of the title compound (yield: 81%).

(f) 2-[[(1S)-1-phenylethyl]amino]ethanehydroxamic acid hydrochloride (Intermediate 32)

To a solution of tert-butyl N-[2-(hydroxyamino)-2-oxo-ethyl]-N-[(1S)-1-phenylethyl]car-bamate (775 mg, 2.63 mmol) in dioxane (1.5 mL) was added 4M HCl in dioxane (5 mL). The reaction mixture was stirred at room temperature for 2 h. The mixture was concentrated under reduced pressure and traces of hydrochloric acid were removed by co-evaporation with dichloromethane (3×) to give 681 mg of the title compound (quantitative yield).
Intermediate 33

2,6-Difluoro-3-phenyl-benzoic acid (a) Methyl 3-bromo-2,6-difluoro-benzoate

This compound was prepared in an analogous manner as described for Intermediate 5a, starting from 3-bromo-2,6-difluoro-benzoic acid to afford 2.24 g of the title compound (yield: 84.6%).

(b) 2,6-Difluoro-3-phenyl-benzoic acid (Intermediate 33)

This compound was prepared in an analogous manner as described for Intermediate 16, starting from methyl 3-bromo-2,6-difluoro-benzoate and phenylboronic acid to afford 260 mg of the title compound (quantitative crude yield).

Intermediate 34

2,6-Difluoro-3-(1-methylpyrazol-4-yl)benzoic acid

This compound was prepared in an analogous manner as described for Intermediate 16, starting from methyl 3-bromo-2,6-difluoro-benzoate (Intermediate 33a) and 1-methyl-4-(4,4,5,5-tetramethyl-1,3,2-dioxaborolan-2-yl)-1H-pyrazole to afford 220 mg of the title compound (yield: 92%).

Intermediate 35

3-Ethynyl-2,6-difluoro-benzoic acid

This compound was prepared in an analogous manner as described for Intermediate 5, starting from methyl 3-bromo-2,6-difluoro-benzoate (Intermediate 33a) and trimethylsilylacetylene to afford 174.2 mg of the title compound (yield: 98.6%).

Intermediate 36

2,6-Difluoro-3-vinyl-benzoic acid

This compound was prepared in an analogous manner as described for Intermediate 14, starting from methyl 3-bromo-2,6-difluoro-benzoate (Intermediate 33a) and vinylboronic anhydride pyridine complex to afford 157.9 mg of the title compound (yield: 92.2%).

Intermediate 37

3-[3-(tert-Butoxycarbonylsulfamoylamino)prop-1-ynyl]-2,6-difluoro-benzoic acid

This compound was prepared in an analogous manner as described for Intermediate 11, starting from methyl 3-bromo-2,6-difluoro-benzoate (Intermediate 33a) and tert-butyl N-(prop-2-ynylsulfamoyl)carbamate (Intermediate 11a) to afford 75 mg of the title compound (quantitative yield).

Intermediate 38

2,6-Difluoro-3-(2-thienyl)benzoic acid

This compound was prepared in an analogous manner as described for Intermediate 16, starting from methyl 3-bromo-2,6-difluoro-benzoate (Intermediate 33a) and 2-(4,4,5,5-tetramethyl-1,3,2-dioxaborolan-2-yl)thiophene to afford 160 mg of the title compound (quantitative crude yield).

Intermediate 39

2,6-Difluoro-3-(5-fluoro-2-thienyl)benzoic acid

This compound was prepared in an analogous manner as described for Intermediate 16, starting from methyl 3-bromo-2,6-difluoro-benzoate (Intermediate 33a) and 2-(5-fluoro-2-thienyl)-4,4,5,5-tetramethyl-1,3,2-dioxaborolane to afford 180 mg of the title compound (quantitative crude yield).

Intermediate 40

2,6-Difluoro-3-(o-tolyl)benzoic acid

This compound was prepared in an analogous manner as described for Intermediate 16, starting from methyl 3-bromo-2,6-difluoro-benzoate (Intermediate 33a) and o-tolylboronic acid to afford 160 mg of the title compound (quantitative crude yield).

Intermediate 41

2,6-Difluoro-3-(1-naphthyl)benzoic acid

This compound was prepared in an analogous manner as described for Intermediate 16, starting from methyl 3-bromo-2,6-difluoro-benzoate (Intermediate 33a) and 1-naphthaleneboronic acid to afford 242 mg of the title compound (quantitative crude yield).

Intermediate 42

2,6-Difluoro-3-(2-naphthyl)benzoic acid

This compound was prepared in an analogous manner as described for Intermediate 16, starting from 3-bromo-2,6-difluorobenzoic acid and 2-naphthaleneboronic acid to afford 185 mg of the title compound (quantitative crude yield).

Intermediate 43

2,6-Difluoro-3-(4-fluorophenyl)benzoic acid

This compound was prepared in an analogous manner as described for Intermediate 16, starting from methyl 3-bromo-2,6-difluoro-benzoate (Intermediate 33a) and 4-fluorobenzeneboronic acid to afford 185 mg of the title compound (quantitative crude yield).

Intermediate A

3-Benzyloxy-2-(5-bromo-2-thienyl)imidazolidin-4-one (a) tert-Butyl N-[2-(benzyloxyamino)-2-oxo-ethyl]carbamate Boc-Gly-OH (2.5 g, 14.3 mmol) and O-benzylhydroxylamine hydrochloride (2.07 g, 13.0 mmol) were suspended in DCM (25 mL). HATU (4.93 g, 13.0 mmol) and NEM (3.3 mL, 25.9 mmol) were added subsequently to the reaction mixture and the mixture was stirred at room temperature o/n. The reaction mixture was concentrated to a small volume and subsequently diluted with ethyl acetate. The organic layer was washed with a 5% NaHCO$_3$-solution, 0.2M HCl-solution, water and brine, then dried over sodium sulfate, filtered and concentrated in vacuo to give 3.3 g of the crude product as an oil (yield 90.6%). This crude product was used in the next step without further purification.

(b) 2-Amino-N-benzyloxy-acetamide 2,2,2-trifluoroacetic acid tert-Butyl N-[2-(benzyloxyamino)-2-oxo-ethyl]carbamate (3.3 g, 11.8 mmol) was dissolved in dichloromethane (20 mL). Water (300 μL) and trifluoroacetic acid (20 mL) were added and the reaction mixture was stirred at room temperature for 3 h. The mixture was concentrated to a small volume and added dropwise to 300 mL of diethyl ether under vigorous stirring. After stirring for an additional hour at room temperature, the diethyl ether layer was decanted. Diethyl ether was added to the remaining precipitate and stirred again for 1 hour. The precipitate was filtered, washed with diethyl ether and dried under vacuum to give 2.87 g of 2-amino-N-benzyloxy-acetamide 2,2,2-trifluoroacetic acid as a white powder (yield: 82.7%).

(c) 3-Benzyloxy-2-(5-bromo-2-thienyl)imidazolidin-4-one (Intermediate A)

To a suspension of 2-amino-N-benzyloxy-acetamide 2,2,2-trifluoroacetic acid (1.54 g, 5.23 mmol) in acetonitril (26 mL) was added subsequently DiPEA (863 µL, 5.23 mmol) and 5-bromothiophene-2-carbaldehyde (622 µL, 5.23 mmol). The reaction mixture was refluxed for 2 h. The mixture was concentrated in vacuo to a small volume. Ethyl acetate was added and the mixture was washed with water and brine, dried over sodium sulfate, filtered and concentrated under reduced pressure to give 1.52 g of crude 3-benzyloxy-2-(5-bromo-2-thienyl)imidazolidin-4-one (yield: 83%).

Intermediate B

3-benzyloxy-2-(4-bromo-2-thienyl)imidazolidin-4-one

This compound was prepared in an analogous manner as described for Intermediate A, starting from 2-amino-N-benzyloxy-acetamide 2,2,2-trifluoroacetic acid and 4-bromo-thiophene-2-carboxaldehyde to afford the title compound (1.8 g, >95%).

Example 1

1-(2,6-Difluorobenzoyl)-2-(4-ethynyl-2-thienyl)-3-hydroxy-imidazolidin-4-one Chlorotrimethylsilane (18.9 µL, 0.15 mmol) was added to a solution of DiPEA (36.4 µL, 0.22 mmol) in dichloromethane (1 mL). The resulting mixture was added dropwise to a stirred suspension of 2-(4-ethynyl-2-thienyl)-3-hydroxy-imidazolidin-4-one (Intermediate 3, 10 mg, 0.07 mmol) in dichloromethane (1 mL). After stirring for 15 minutes at room temperature, the reaction mixture was cooled to 0° C. and DiPEA (27.4 µL, 0.15 mmol) was added followed by a solution of 2,6-difluorobenzoyl chloride (8.8 µL, 0.07 mmol) in dichloromethane (0.5 mL). The resulting solution was stirred for 15 minutes at 0° C. The reaction was quenched with 5% citric acid solution (4 mL). The water-layer was extracted with dichloromethane. The combined organic layers were washed with a solution of 5% $NaHCO_3$(4 mL), filtered over a PE filter and concentrated in vacuo to give an oil. The residue was dissolved in ethyl acetate (1 mL) and 1-methylpiperazine (15 µL, 0.15 mmol) in ethyl acetate (0.5 mL) was added. The reaction mixture was stirred at room temperature for 30 min. Ethyl acetate was added and the mixture was washed with 0.1M HCl-solution in water and brine. The organic layer was subsequently dried over sodium sulfate, filtered and concentrated under reduced pressure. Purification was performed using preparative HPLC to afford the title compound (9 mg, 37%). Data: LCMS (B) $R_t$: 8.833 min; m/z 392.9 [M−H+HCOOH]−.

Example 2

2-(5-Bromo-2-thienyl)-1-(2-fluorobenzoyl)-3-hydroxy-imidazolidin-4-one

(a) 3-Benzyloxy-2-(5-bromo-2-thienyl)-1-(2-fluorobenzoyl)imidazolidin-4-one To a cold (4° C.) solution of 3-benzyloxy-2-(5-bromo-2-thienyl)imidazolidin-4-one (Intermediate A, 70 mg, 0.2 mmol) in acetonitril (1 mL) and N,N-diisopropylethylamine (66 µL, 0.4 mmol) was added dropwise a solution of 2-fluorobenzoyl chloride (24 µL, 0.2 mmol) in acetonitril (1 mL). The reaction mixture was stirred for 2 h allowing to come to room temperature. The mixture was concentrated in vacuo to a small volume. Ethyl acetate was added and the mixture was washed with 0.1M HCl-solution, 5% $NaHCO_3$-solution, water and brine, dried over sodium sulfate, filtered and concentrated in vacuo. The crude residue was purified by column chromatography (heptane to ethyl acetate=10/0 to 0/10 v/v %) to afford 35 mg of the title compound (yield: 37%).

(b) 2-(5-Bromo-2-thienyl)-1-(2-fluorobenzoyl)-3-hydroxy-imidazolidin-4-one (Example 2)

To a cold (0° C.) solution of 3-benzyloxy-2-(5-bromo-2-thienyl)-1-(2-fluorobenzoyl)imidazolidin-4-one (35 mg, 0.07 mmol) in dichloromethane (4 mL) was added boron trifluoride methyl sulfide complex (15 µL, 0.15 mmol).The reaction mixture was stirred for 3 h allowing the temperature to reach room temperature. The mixture was quenched with methanol (0.5 mL) and stirred 30 minutes at room temperature. A 5% $NaHCO_3$-solution in water (2 mL) was added followed by dichloromethane and the layers were separated. The water layer was extracted with dichloromethane (3 mL). The combined organic layers were washed with water (5 mL) and filtered over a PE filter and concentrated in vacuo to give the crude title compound. Purification was performed using preparative HPLC to afford the title compound (6.5 mg, 31%). Data: LCMS (B) $R_t$: 9.670 min; m/z 384.9/386.9 [M+H]+ (bromide pattern).

Example 3

2-(5-Bromo-2-thienyl)-1-(2-chloro-6-fluoro-benzoyl)-3-hydroxy-imidazolidin-4-one This compound was prepared from Intermediate A and 2-chloro-6-fluorobenzoyl chloride according to procedures described in Example 2. Purification was performed using preparative HPLC to afford the title compound (14.0 mg, 55%). Data: LCMS (B) $R_t$: 10.212 min; m/z 462.9/464.8 [M−H+HCOOH]− (bromide/chloride pattern).

Example 4

2-(5-Bromo-2-thienyl)-1-(2,6-difluorobenzoyl)-3-hydroxy-imidazolidin-4-one

This compound was prepared from Intermediate A and 2,6-difluorobenzoyl chloride according to procedures described in Example 2. Purification was performed using preparative HPLC to afford the title compound (35 mg, 66%). Data: LCMS (B) $R_t$: 9.821 min; m/z 446.9/448.8 [M−H+HCOOH]− (bromide pattern).

Example 5

1-Benzoyl-2-(5-bromo-2-thienyl)-3-hydroxy-imidazolidin-4-one

This compound was prepared from Intermediate A and benzoyl chloride according to procedures described in Example 2. Purification was performed using preparative HPLC to afford the title compound (9 mg, 41%). Data: LCMS (B) $R_t$: 9.609 min; m/z 366.8/369.0 [M+H]$^+$ (bromide pattern).

Example 6

2-(5-Bromo-2-thienyl)-1-[2-fluoro-6-(trifluoromethyl)benzoyl]-3-hydroxy-imidazolidin-4-one This compound was prepared from Intermediate A and 2-fluoro-6-(trifluoromethyl)benzoyl chloride according to procedures described in Example 2. Purification was performed using preparative HPLC to afford the title compound (13 mg, 51%). Data: LCMS (B) $R_t$: 11.051 min; m/z 496.9/498.9 [M−H+HCOOH]$^-$ (bromide pattern).

Example 7

2-(4-Bromo-2-thienyl)-1-(2-chloro-6-fluoro-benzoyl)-3-hydroxy-imidazolidin-4-one This compound was prepared from Intermediate B and 2-chloro-6-fluorobenzoyl chloride according to procedures described in Example 2. Purification was performed using preparative HPLC to afford the title compound (33 mg, 56%). Data: LCMS (B) $R_t$: 10.020 min; m/z 462.8/464.9 [M−H+HCOOH]$^-$ (bromide/chloride pattern).

Example 8

2-(4-Bromo-2-thienyl)-1-(2,6-difluorobenzoyl)-3-hydroxy-imidazolidin-4-one (a) 3-Benzyloxy-2-(4-bromo-2-thienyl)-1-(2,6-difluorobenzoyl)imidazolidin-4-one To a suspension of 2-amino-N-benzyloxy-acetamide 2,2,2-trifluoroacetic acid (Intermediate Ab, 59 mg, 0.2 mmol) and 4-bromothiophene-2-carboxaldehyde (38 mg, 0.2 mmol) in acetonitrile (1 mL) was added N,N-diisopropylethylamine (33.0 μL, 0.2 mmol). The white suspension was heated for 2 h at 50° C. during which the suspension turned into a clear solution. The mixture was cooled on an ice-water bath to <5° C. and N,N-diisopropylethylamine (33.0 μL, 0.2 mmol) was added. Subsequently a solution of 2,6-difluorobenzoyl chloride (30 μL, 0.24 mmol) in acetonitrile (0.1 mL) was added dropwise keeping the temperature below 5° C. The temperature of the reaction mixture was allowed to come to room temperature. The mixture was partially diluted with ethyl acetate (5 mL) and water (3 mL) was added slowly. The resulting phases were separated and the water layer was extracted with ethyl acetate (3 mL). The combined organic layers were washed with water (5 mL), 5% NaHCO$_3$-solution (5 mL), water (5 mL) and brine (5 mL), filtered over a PE filter filled with Na$_2$SO$_4$ and concentrated under reduced pressure. The crude residue was purified by column chromatography (heptane to ethyl acetate=0 to 100 v/v %) to afford the title compound (72 mg, 72%) as a white solid.

(b) 2-(4-Bromo-2-thienyl)-1-(2,6-difluorobenzoyl)-3-hydroxy-imidazolidin-4-one (Example 8)

This compound was prepared in an analogous manner as described for Example 2b starting from 3-benzyloxy-2-(4-bromo-2-thienyl)-1-(2,6-difluorobenzoyl)imidazolidin-4-one. Purification was performed using preparative HPLC to afford the title compound (32 mg, 61%). Data: LCMS (B) $R_t$: 9.615 min; m/z 446.8/448.9 [M−H+HCOOH]$^-$ (bromide pattern).

Example 9

2-(4-Bromo-2-thienyl)-1-(2-fluorobenzoyl)-3-hydroxy-imidazolidin-4-one

This compound was prepared from Intermediate B and 2-fluorobenzoyl chloride according to procedures described in Example 2. Purification was performed using preparative HPLC to afford the title compound (18 mg, 31%). Data: LCMS (B) $R_t$: 9.410 min; m/z 384.8/386.9 [M+H]$^+$ (bromide pattern).

Example 10

2-(4-Bromo-2-thienyl)-1-(2,6-dichlorobenzoyl)-3-hydroxy-imidazolidin-4-one

This compound was prepared from Intermediate B and 2,6-dichlorobenzoyl chloride according to procedures described in Example 2. Purification was performed using preparative HPLC to afford the title compound (44 mg, 78%). Data: LCMS (B) $R_t$: 10.496 min; m/z 480.8/482.8 [M−H+HCOOH]$^-$ (bromide/dichloride pattern).

Example 11

2-(4-Bromo-2-thienyl)-1-[2-fluoro-6-(trifluoromethyl)benzoyl]-3-hydroxy-imidazolidin-4-one This compound was prepared from Intermediate B and 2-fluoro-6-(trifluoromethyl)benzoyl chloride according to procedures described in Example 2. Purification was performed using preparative HPLC to afford the title compound (48 mg, 81%). Data: LCMS (B) $R_t$: 10.908 min; m/z 496.9/498.9 [M−H+HCOOH]$^-$ (bromide pattern).

Example 12

1-Benzoyl-2-(4-bromo-2-thienyl)-3-hydroxy-imidazolidin-4-one

This compound was prepared from Intermediate B and benzoyl chloride according to procedures described in Example 2. Purification was performed using preparative HPLC to afford the title compound (37 mg, 72%). Data: LCMS (B) $R_t$: 9.294 min; m/z 366.9/368.8 [M+H]$^-$ (bromide pattern).

Example 13

1-(2-Fluorobenzoyl)-3-hydroxy-2-(5-methylsulfanyl-2-thienyl)imidazolidin-4-one

This compound was prepared in an analogous manner as described for Example 8a starting from Intermediate Ab, 5-methylsulfanylthiophene-2-carbaldehyde and 2-fluorobenzoyl chloride. Subsequent benzyl-deprotection was performed according to the procedure described in Example 2b. Purification was performed using preparative HPLC to afford the title compound (23.7 mg, 61%). Data: LCMS (B) $R_t$: 9.517 min; m/z 353.0 [M+H]$^+$.

Example 14

1-(2,6-Difluorobenzoyl)-3-hydroxy-2-(5-methylsulfanyl-2-thienyl)imidazolidin-4-one This compound was prepared in an analogous manner as described for Example 8a starting from Intermediate Ab, 5-methylsulfanylthiophene-2-carbaldehyde and 2,6-difluorobenzoyl chloride. Subsequent benzyl-deprotection was performed according to the procedure described in Example 2b. Purification was performed using preparative HPLC to afford the title compound (18.1 mg, 38%). Data: LCMS (B) $R_t$: 9.618 min; m/z 415.0 [M–H+HCOOH]⁻.

Example 15

1-(2-Chloro-6-fluoro-benzoyl)-3-hydroxy-2-(5-methylsulfanyl-2-thienyl)imidazolidin-4-one This compound was prepared in an analogous manner as described for Example 8a starting from Intermediate Ab, 5-methylsulfanylthiophene-2-carbaldehyde and 2-chloro-6-fluorobenzoyl chloride. Subsequent benzyl-deprotection was performed according to the procedure described in Example 2b. Purification was performed using preparative HPLC to afford the title compound (28.7 mg, 53%). Data: LCMS (B) $R_t$: 10.109 min; m/z 386.9/388.9 [M+H]⁺ (chloride pattern).

Example 16

1-(2,6-Difluorobenzoyl)-3-hydroxy-2-(5-nitro-2-thienyl)imidazolidin-4-one

This compound was prepared in an analogous manner as described for Example 8a starting from Intermediate Ab, 5-nitrothiophene-2-carbaldehyde and 2,6-difluorobenzoyl chloride. Subsequent benzyl-deprotection was performed according to the procedure described in Example 2b. Purification was performed using preparative HPLC to afford the title compound (3.7 mg, 11%). Data: LCMS (B) $R_t$: 9.010 min; m/z 414.0 [M–H+HCOOH]⁻.

Example 17

1-(2-Chloro-6-fluoro-benzoyl)-2-(5-ethyl-2-thienyl)-3-hydroxy-imidazolidin-4-one This compound was prepared in an analogous manner as described for Example 8a starting from Intermediate Ab, 5-ethylthiophene-2-carbaldehyde and 2-chloro-6-fluorobenzoyl chloride. Subsequent benzyl-deprotection was performed according to the procedure described in Example 2b. Purification was performed using preparative HPLC to afford the title compound (20.9 mg, 94%). Data: LCMS (B) $R_t$: 10.402 min; m/z 413.0/414.9 [M–H+HCOOH]⁻ (chloride pattern).

Example 18

1-(2,6-Difluorobenzoyl)-2-(5-ethyl-2-thienyl)-3-hydroxy-imidazolidin-4-one

This compound was prepared in an analogous manner as described for Example 8a starting from Intermediate Ab, 5-ethylthiophene-2-carbaldehyde and 2,6-difluorobenzoyl chloride. Subsequent benzyl-deprotection was performed according to the procedure described in Example 2b. Purification was performed using preparative HPLC to afford the title compound (18.8 mg, 67%). Data: LCMS (B) $R_t$: 9.956 min; m/z 396.9 [M–H+HCOOH]⁻.

Example 19

2-(5-Ethyl-2-thienyl)-1-(2-fluorobenzoyl)-3-hydroxy-imidazolidin-4-one

This compound was prepared in an analogous manner as described for Example 8a starting from Intermediate Ab, 5-ethylthiophene-2-carbaldehyde and 2-fluorobenzoyl chloride. Subsequent benzyl-deprotection was performed according to the procedure described in Example 2b. Purification was performed using preparative HPLC to afford the title compound (15.1 mg, 45%). Data: LCMS (B) $R_t$: 9.816 min; m/z 379.0 [M–H+HCOOH]⁻.

Example 20

1-(2,6-Difluorobenzoyl)-3-hydroxy-2-(5-nitro-3-thienyl)imidazolidin-4-one

This compound was prepared in an analogous manner as described for Example 8a starting from Intermediate Ab, 5-nitrothiophene-3-carbaldehyde and 2,6-difluorobenzoyl chloride. Subsequent benzyl-deprotection was performed according to the procedure described in Example 2b. Purification was performed using preparative HPLC to afford the title compound (34.7 mg, 55%). Data: LCMS (B) $R_t$: 8.459 min; m/z 414.0 [M–H+HCOOH]⁻.

Example 21

1-(2,6-Difluorobenzoyl)-3-hydroxy-2-(4-nitro-2-thienyl)imidazolidin-4-one

This compound was prepared in an analogous manner as described for Example 8a starting from Intermediate Ab, 4-nitrothiophene-2-carbaldehyde and 2,6-difluorobenzoyl chloride. Subsequent benzyl-deprotection was performed according to the procedure described in Example 2b. Purification was performed using preparative HPLC to afford the title compound (21.8 mg, 42%). Data: LCMS (B) $R_t$: 8.306 min; m/z 414.0 [M–H+HCOOH]⁻.

Example 22

2-(4-Bromothiazol-2-yl)-1-(2,6-difluorobenzoyl)-3-hydroxy-imidazolidin-4-one

This compound was prepared in an analogous manner as described for Example 8a starting from Intermediate Ab, 4-bromothiazole-2-carbaldehyde and 2,6-difluorobenzoyl chloride. Subsequent benzyl-deprotection was performed according to the procedure described in Example 2b. Purification was performed using preparative HPLC to afford the title compound (16.6 mg, 49%). Data: LCMS (B) $R_t$: 8.060 min; m/z 403.9/405.9 [M+H]⁺ (bromide pattern).

Example 23

2-(4-Bromo-2-furyl)-1-(2,6-difluorobenzoyl)-3-hydroxy-imidazolidin-4-one

This compound was prepared in an analogous manner as described for Example 8a starting from Intermediate Ab, 4-bromofuran-2-carbaldehyde and 2,6-difluorobenzoyl chloride. Subsequent benzyl-deprotection was performed according to the procedure described in Example 2b. Purification was performed using preparative HPLC to afford the title compound (27.7 mg, 48%). Data: LCMS (B) $R_t$: 8.997 min; m/z 430.9/432.9 [M−H+HCOOH]⁻ (bromide pattern).

Example 24

2-(2-Bromothiazol-4-yl)-1-(2,6-difluorobenzoyl)-3-hydroxy-imidazolidin-4-one

This compound was prepared in an analogous manner as described for Example 8a starting from Intermediate Ab, 2-bromothiazole-4-carbaldehyde and 2,6-difluorobenzoyl chloride. Subsequent benzyl-deprotection was performed according to the procedure described in Example 2b. Purification was performed using preparative HPLC to afford the title compound (40 mg, 66%). Data: LCMS (B) $R_t$: 7.658 min; m/z 403.9/406.0 [M+H]⁺ (bromide pattern).

Example 25

2-(2-Bromothiazol-5-yl)-1-(2,6-difluorobenzoyl)-3-hydroxy-imidazolidin-4-one (a) [2-(2-Bromothiazol-5-yl)-3-(2,6-difluorobenzoyl)-5-oxo-imidazolidin-1-yl] 2,6-difluorobenzoate To a suspension of 2-aminoethanehydroxamic acid (Intermediate 1, 36 mg, 0.40 mmol) in acetonitrile (1 mL) was added a solution of 2-bromothiazole-5-carbaldehyde (41 mg, 0.42 mmol) in acetonitrile (0.7 mL). The reaction mixture was stirred for 1 h. at reflux and at room temperature o/n. The mixture was cooled on an ice-water bath to <5° C. and N,N-diisopropylethylamine (257 μL, 1.56 mmol) was added. Subsequently a solution of 2,6-difluorobenzoyl chloride (108 μL, 0.86 mmol) in acetonitrile (0.5 mL) was added dropwise keeping the temperature below 5° C. The temperature of the reaction mixture was allowed to come to room temperature. The mixture was diluted with ethyl acetate (5 mL) and water (3 mL) was added slowly. The resulting phases were separated and the water layer was extracted with ethyl acetate (3 mL). The combined organic layers were washed with water (5 mL), 5% NaHCO₃-solution (5 mL), water (5 mL) and brine (5 mL), filtered over a PE filter filled with Na₂SO₄ and concentrated under reduced pressure. The crude residue was purified by column chromatography (heptane to ethyl acetate=0 to 100 v/v %) to afford the title compound (19 mg, 9%) as a white solid.

(b) 2-(2-Bromothiazol-5-yl)-1-(2,6-difluorobenzoyl)-3-hydroxy-imidazolidin-4-one (Example 25)

To a solution of [2-(2-bromothiazol-5-yl)-3-(2,6-difluorobenzoyl)-5-oxo-imidazolidin-1-yl] 2,6-difluorobenzoate (19 mg, 0.034 mmol) in ethyl acetate (0.5 mL) was added a solution of 1-methylpiperazine (6 μL, 0.054 mmol) in ethyl acetate (0.5 mL). The reaction mixture was stirred at room temperature for 10 min. Ethyl acetate was added and the mixture was washed with 0.1M HCl-solution in water and brine. The organic layer was subsequently dried over sodium sulfate, filtered and concentrated under reduced pressure. Purification was performed using preparative HPLC to afford the title compound (2.4 mg, 17%). Data: LCMS (B) $R_t$: 8.020 min; m/z 403.9/405.9 [M+H]⁺ (bromide pattern).

Example 26

2-(Benzothiophen-2-yl)-1-(2,6-difluorobenzoyl)-3-hydroxy-imidazolidin-4-one

This compound was prepared in an analogous manner as described for Example 8a starting from Intermediate Ab, benzothiophene-2-carbaldehyde and 2,6-difluorobenzoyl chloride. Subsequent benzyl-deprotection was performed according to the procedure described in Example 2b. Purification was performed using preparative HPLC to afford the title compound (33.4 mg, 69%). Data: LCMS (B) $R_t$: 10.280 min; m/z 419.0 [M−H+HCOOH]⁻.

Example 27

2-(Benzothiophen-2-yl)-1-(2-chloro-6-fluoro-benzoyl)-3-hydroxy-imidazolidin-4-one This compound was prepared in an analogous manner as described for Example 8a starting from Intermediate Ab, benzothiophene-2-carbaldehyde and 2-chloro-6-fluorobenzoyl chloride. Subsequent benzyl-deprotection was performed according to the procedure described in Example 2b. Purification was performed using preparative HPLC to afford the title compound (32.7 mg, 60%). Data: LCMS (B) $R_t$: 10.726 min; m/z 435.0/436.9 [M−H+HCOOH]⁻ (chloride-pattern).

Example 28

2-(5-Bromo-3-thienyl)-1-(2,6-difluorobenzoyl)-3-hydroxy-imidazolidin-4-one

This compound was prepared in an analogous manner as described for Example 8a starting from Intermediate Ab, 5-bromothiophene-3-carbaldehyde and 2,6-difluorobenzoyl chloride. Subsequent benzyl-deprotection was performed according to the procedure described in Example 2b. Purification was performed using preparative HPLC to afford the title compound (38 mg, 67%). Data: LCMS (B) $R_t$: 9.516 min; m/z 446.9/448.9 [M−H+HCOOH]⁻ (bromide-pattern).

Example 29

5-[1-(2-Chloro-6-fluoro-benzoyl)-3-hydroxy-4-oxo-imidazolidin-2-yl]thiophene-3-carbonitrile This compound was prepared in an analogous manner as described for Example 8a starting from Intermediate Ab, 5-formylthiophene-3-carbonitrile and 2-chloro-6-fluorobenzoyl chloride. Subsequent benzyl-deprotection was performed according to the procedure described in Example 2b. Purification was performed using preparative HPLC to afford the title compound (19 mg, 40%). Data: LCMS (B) $R_t$: 8.196 min; m/z 728.9/730.9 [2M−H]⁻ (chloride-pattern).

Example 30

5-[1-(2,6-Difluorobenzoyl)-3-hydroxy-4-oxo-imidazolidin-2-yl]thiophene-3-carbonitrile This compound was prepared in an analogous manner as described for Example 8a starting from Intermediate Ab, 5-formylthiophene-3-carbonitrile and 2,6-difluorobenzoyl chloride. Subsequent benzyl-deprotection was performed according to the procedure described in Example 2b. Purification was performed using preparative HPLC to afford the title compound (6 mg, 7%). Data: LCMS (B) $R_t$: 7.645 min; m/z 348.0 [M–H]$^-$.

Example 31

5-[1-(2-Fluorobenzoyl)-3-hydroxy-4-oxo-imidazolidin-2-yl]thiophene-3-carbonitrile This compound was prepared in an analogous manner as described for Example 8a starting from Intermediate Ab, 5-formylthiophene-3-carbonitrile and 2-fluorobenzoyl chloride. Subsequent benzyl-deprotection was performed according to the procedure described in Example 2b. Purification was performed using preparative HPLC to afford the title compound (8.7 mg, 18%). Data: LCMS (B) $R_t$: 7.338 min; m/z 330.0 [M–H]$^-$, 375.9 [M–H+HCOOH]$^-$.

Example 32

1-(2,6-Difluorobenzoyl)-3-hydroxy-2-(4-methyl-2-thienyl)imidazolidin-4-one

3-Benzyloxy-2-(4-bromo-2-thienyl)-1-(2,6-difluorobenzoyl)imidazolidin-4-one (Intermediate 8a, 50 mg, 0.1 mmol) was suspended in dioxane (1 mL) and potassium carbonate (21 mg, 0.15 mmol) was added. The solution was purged with nitrogen for 5 min, trimethylboroxin (50% solution in THF, 56 µL, 0.2 mmol) and PdCl$_2$(dppf).CH$_2$Cl$_2$ (8.2 mg, 0.01 mmol) were added. The reaction mixture was stirred for 18 h at 100° C. The reaction mixture was added to a stirred mixture of 5% citric acid solution/brine/ethyl acetate=1/1/1 v/v % (30 mL). The organic layer was separated, washed with water, brine, dried over sodium sulfate, filtered and concentrated under reduced pressure. The crude residue was purified by column chromatography (heptane to ethyl acetate=10/0 to 1/1 v/v %) to afford the title compound (21 mg, yield: 33%). Subsequent benzyl-deprotection was performed according to the procedure described in Example 2b. Purification was performed using preparative HPLC to afford the title compound (6.9 mg, 41%). Data: LCMS (B) $R_t$: 8.822 min; m/z 383.0 [M–H]$^-$.

Example 33

2-(4-Chloro-2-thienyl)-1-(2,6-difluorobenzoyl)-3-hydroxy-imidazolidin-4-one

This compound was prepared in an analogous manner as described for Example 8a starting from Intermediate Ab, 4-chlorothiophene-2-carbaldehyde and 2,6-difluorobenzoyl chloride. Subsequent benzyl-deprotection was performed according to the procedure described in Example 2b. Purification was performed using preparative HPLC to afford the title compound (13 mg, 16%). Data: LCMS (B) $R_t$: 9.339 min; m/z 402.9/405.0 [M–H+HCOOH]$^-$ (chloride-pattern).

Example 35

2-(4-Ethynyl-2-thienyl)-1-(2-fluorobenzoyl)-3-hydroxy-imidazolidin-4-one

This compound was prepared in an analogous manner as described for Example 1 starting from 2-(4-ethynyl-2-thienyl)-3-hydroxy-imidazolidin-4-one (Intermediate 3) and 2-fluorobenzoyl chloride. Purification was performed using preparative HPLC to afford the title compound (3 mg, 6%). Data: LCMS (B) $R_t$: 8.676 min; m/z 375.0 [M–H+HCOOH]$^-$.

Example 36

1-(2,6-Difluorobenzoyl)-3-hydroxy-2-(4-iodo-2-thienyl)imidazolidin-4-one

This compound was prepared in an analogous manner as described for Example 1 starting from 2-(4-ethynyl-2-thienyl)-3-hydroxy-imidazolidin-4-one (Intermediate 4) and 2,6-difluorobenzoyl chloride. Purification was performed using preparative HPLC to afford the title compound (7 mg, 8%). Data: LCMS (B) $R_t$: 9.941 min; m/z 494.9 [M–H+HCOOH]$^-$.

Example 37

2-(4-Bromo-5-fluoro-2-thienyl)-1-(2,6-difluorobenzoyl)-3-hydroxy-imidazolidin-4-one This compound was prepared in an analogous manner as described for Example 8a starting from Intermediate Ab, 4-bromo-5-fluoro-thiophene-2-carbaldehyde (prepared according to Badland et al, Bioorg. Med. Chem. Letters (2011) 21 528-530) and 2,6-difluorobenzoyl chloride. Subsequent benzyl-deprotection was performed according to the procedure described in Example 2b. Purification was performed using preparative HPLC to afford the title compound (28 mg, 24%). Data: LCMS (B) $R_t$: 10.567 min; m/z 464.9/466.9 [M–H+HCOOH]$^-$ (bromide-pattern).

Example 38

2-(4-Bromo-2-thienyl)-1-(4-ethynyl-2,6-difluoro-benzoyl)-3-hydroxy-imidazolidin-4-one (a) 4-Ethynyl-2,6-difluoro-benzoyl chloride 4-Ethynyl-2,6-difluoro-benzoic acid (Intermediate 5, 55 mg, 0.3 mmol) was suspended in dichloromethane (1 mL), DMF (10 µL) was added and the mixture was stirred at 4° C. under nitrogen atmosphere. Oxalyl chloride (28 µL, 0.33 mmol) was added and the reaction mixture was stirred for 2 h at 4° C. This mixture was used in the next step without work-up.

(b) 2-(4-Bromo-2-thienyl)-1-(4-ethynyl-2,6-difluoro-benzoyl)-3-hydroxy-imidazolidin-4-one (Example 38)

This compound was prepared in an analogous manner as described for Example 8a starting from Intermediate Ab, 4-Bromothiophene-2-carboxaldehyde and 4-ethynyl-2,6-difluoro-benzoyl chloride. Subsequent benzyl-deprotection was performed according to the procedure described in Example 2b. Purification was performed using preparative HPLC to afford the title compound (17 mg, 25%). Data: LCMS (B) $R_t$: 11.054 min; m/z 470.9/472.9 [M–H+HCOOH]$^-$ (bromide-pattern).

Example 39

2-(4-Bromo-2-thienyl)-1-[4-(2-cyclopropylethynyl)-2,6-difluoro-benzoyl]-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 4-(2-cyclopropylethynyl)-2,6-difluoro-benzoic acid (Intermediate 6). Purification was performed using preparative HPLC to afford the title compound (14 mg, 45%). Data: LCMS (B) $R_t$: 13.507 min; m/z 510.9/512.9 [M−H+HCOOH]⁻.

Example 40

N-[3-[4-[2-(4-bromo-2-thienyl)-3-hydroxy-4-oxo-imidazolidine-1-carbonyl]-3,5-difluoro-phenyl]-prop-2-ynyl]methanesulfonamide This compound was prepared in an analogous manner as described for Example 1 and Example 38a starting from 2-(4-bromo-2-thienyl)-3-hydroxy-imidazolidin-4-one (Intermediate 2) and 2,6-difluoro-4-[3-(methanesulfonamido)prop-1-ynyl]benzoic acid (Intermediate 9). Purification was performed using preparative HPLC to afford the title compound (14 mg, 45%). Data: LCMS (B) $R_t$: 13.507 min; m/z 510.9/512.9 [M−H+HCOOH]⁻.

Example 41

2-(5-Bromo-2-thienyl)-1-[(2-fluorophenyl)methyl]-3-hydroxy-imidazolidin-4-one (a) 2-[(2-Fluorophenyl)methylamino]ethanehydroxamic acid A solution of 2-fluorobenzaldehyde (351 µL, 3.33 mmol) in methanol (7 mL) was added to a solution of 2-aminoethanehydroxamic acid (300 mg, 3.33 mmol) in water (1.33 mL) and a 2N NaOH-solution in water (1.66 mL, 3.33 mmol). The reaction mixture was stirred for 5 min at room temperature after which a precipitation occurred. NaBH₄ (126 mg, 3.33 mmol) was added and the reaction mixture was stirred for 30 min at room temperature. Methanol was removed by evaporation under reduced pressure and the resulting solution was diluted by addition of water. After addition of 2M HCl-solution till pH ~7, dichloromethane/methanol=9/1 v/v % was added to the solution. The organic layer was then separated over a PE filter and concentrated in vacuo. The crude residue was purified by column chromatography (dichloromethane to methanol=9/1 to 8/2 v/v %) to afford 128 mg of the title compound (yield: 19%).

(b) 2-(5-Bromo-2-thienyl)-1-[(2-fluorophenyl)methyl]-3-hydroxy-imidazolidin-4-one (Example 41)

To a solution 2-[(2-fluorophenyl)methylamino]ethanehydroxamic acid (25 mg, 0.126 mmol) in ethanol (2 mL) was added 5-bromothiophene-2-carbaldehyde (24 mg, 0.126 mmol) and the reaction mixture was stirred at reflux temperature for 1 h. The solvent was evaporated under reduced pressure. The crude residue was purified by column chromatography (heptane to ethyl acetate=10/0 to 2/8 v/v). Purification was performed using preparative HPLC to afford the title compound (21 mg, 45%). Data: LCMS (B) $R_t$: 12.557 min; m/z 370.9/372.9 [M+H]⁺ (bromide pattern).

Example 42

2-(5-Bromo-3-thienyl)-1-[(2-fluorophenyl)methyl]-3-hydroxy-imidazolidin-4-one

This compound was prepared according to procedures described in Example 41 starting from 2-[(2-fluorophenyl)methylamino]ethanehydroxamic acid and 5-bromothiophene-3-carbaldehyde. Purification was performed using preparative HPLC to afford the title compound (24 mg, 51%). Data: LCMS (A) $R_t$: 12.271 min; m/z 370.9/372.9 [M+H]⁺ (bromide pattern).

Example 43

2-(4-Bromo-2-thienyl)-1-[(2-fluorophenyl)methyl]-3-hydroxy-imidazolidin-4-one

This compound was prepared according to procedures described in Example 41 starting from 2-[(2-fluorophenyl)methylamino]ethanehydroxamic acid and 4-bromothiophene-2-carbaldehyde. Purification was performed using preparative HPLC to afford the title compound (20 mg, 43%). Data: LCMS (A) $R_t$: 12.366 min; m/z 370.9/372.9 [M+H]⁺ (bromide pattern).

Example 44

2-(4-Bromo-2-thienyl)-1-[(2,6-difluorophenyl)methyl]-3-hydroxy-imidazolidin-4-one This compound was prepared according to procedures described in Example 41 starting from 2-[(2,6-difluorophenyl)methylamino]ethanehydroxamic acid and 4-bromothiophene-2-carbaldehyde. Purification was performed using preparative HPLC to afford the title compound (11 mg, 5%). Data: LCMS (A) $R_t$: 12.164 min; m/z 388.9/390.9 [M+H]⁺ (bromide pattern).

Separation of Enantiomers of Example 44

Example 45a and Example 45b 2-(4-Bromo-2-thienyl)-1-[(2,6-difluorophenyl)methyl]-3-hydroxy-imidazolidin-4-one (isomer 1 and isomer 2)

To a cold (0° C.) solution of 2-(4-bromo-2-thienyl)-1-[(2,6-difluorophenyl)methyl]-3-hydroxy-imidazolidin-4-one (Example 44, 100 mg, 0.26 mmol) in dichloromethane (2 mL) was added subsequently N,N-diisopropylethylamine (107 µL, 0.64 mmol) and a solution of (2S)-2-phenylbutanoyl chloride (49.5 mg, 0.27 mmol) in dichloromethane (0.5 mL). The reaction mixture was stirred for 30 min allowing the temperature to come to room temperature. The mixture was diluted with ethyl acetate and washed with water, brine, dried over sodium sulfate, filtered and the solvent was removed by evaporation at reduced pressure to give 69 mg of the crude product. The mixture of the two diastereomers was separated by column chromatography (heptane to ethyl acetate=100/0 to 75/25 v/v %) to afford the two separate diastereomers (diastereomer 1, first eluting from the column, obtained in 26 mg (yield: 19%) and diastereomer 2, last eluting, in 27 mg (yield: 20%)). ¹H-NMR showed for diastereomer 1>90% de, and for diastereomer 2>90% de.

Both diastereomers were reacted separately with 1.5 eq. of 1-methylpiperazine in ethyl acetate at room temperature o/n. After reaction, ethyl acetate was added and the mixture was washed with 0.1M HCl-solution, water, brine, dried over sodium sulfate, filtered and concentrated in vacuo. Enantiomeric enriched compounds were obtained after purification using preparative HPLC to afford Example 45a, 2-(4-bromo-2-thienyl)-1-[(2,6-difluorophenyl)methyl]-3- hydroxy-imidazolidin-4-one (isomer 1, less active isomer, 19 mg, >95%) and Example 45b, 2-(4-bromo-2-thienyl)-1-[(2,6-difluorophenyl)methyl]-3-hydroxy-imidazolidin-4-one (isomer 2, most active isomer, 22 mg, >95%). Data: Example 45a LCMS (B) $R_t$: 12.155 min; m/z 388.9/390.9 [M+H]$^+$ (bromide pattern). Example 45b LCMS (B) $R_t$: 12.135 min; m/z 388.9/390.9 [M+H]$^+$ (bromide pattern).

Separation of Enantiomers of Example 28

Example 46a and Example 46b 2-(5-Bromo-3-thienyl)-1-(2,6-difluorobenzoyl)-3-hydroxy-imidazolidin-4-one (isomer 1 and isomer 2)

These diastereomers were prepared in an analogous manner as described for Example 45a and 45b starting from 2-(5-bromo-3-thienyl)-1-(2,6-difluorobenzoyl)-3-hydroxy-imidazolidin-4-one (Example 28) and (2S)-2-phenylbutanoic acid.

The mixture of the two diastereomers was separated by column chromatography (toluene/ethyl acetate=96/4 v/v % isocratic) to afford the two separate diastereomers (diastereomer 1, first eluting from the column obtained in 109 mg (yield: 27%) and diastereomer 2, last eluting in 89 mg (yield: 22%)). $^1$H-NMR showed for diastereomer 1>90% de and for diastereomer 2>90% de.

Both diastereomers were reacted separately with 1-methylpiperazine according to the procedure as described in Example 45. Enantiomeric enriched compounds were obtained after purification using preparative HPLC to afford Example 46a, 2-(5-bromo-3-thienyl)-1-(2,6-difluorobenzoyl)-3-hydroxy-imidazolidin-4-one (isomer 1, less active isomer, 74 mg, 92%) and Example 46b, 2-(5-bromo-3-thienyl)-1-(2,6-difluorobenzoyl)-3-hydroxy-imidazolidin-4-one (isomer 2, most active isomer, 65 mg, >95%). Data: Example 46a LCMS (B) $R_t$: 9.523 min; m/z 446.9/448.9 [M−H+HCOOH]$^−$ (bromide pattern). Example 46b LCMS (B) $R_t$: 9.526 min; m/z 446.9/448.9 [M−H+HCOOH]$^−$ (bromide pattern).

Separation of Enantiomers of Example 39

Example 47a and Example 47b 2-(4-Bromo-2-thienyl)-1-[4-(2-cyclopropylethynyl)-2,6-difluoro-benzoyl]-3-hydroxy-imidazolidin-4-one (isomer 1 and isomer 2)

These diastereomers were prepared in an analogous manner as described for Example 45a and 45b starting from 2-(4-bromo-2-thienyl)-1-[4-(2-cyclopropylethynyl)-2,6-difluoro-benzoyl]-3-hydroxy-imidazolidin-4-one (Example 39) and (2S)-2-phenylbutanoic acid.

The mixture of the two diastereomers was separated by column chromatography (heptane to ethyl acetate=100/0 to 78/22 v/v %) to afford the two separate diastereomers (diastereomer 1, first eluting from the column obtained in 24 mg (yield: 15%) and diastereomer 2, last eluting in 63 mg (yield: 39%)). $^1$H-NMR showed for diastereomer 1>90% de and for diastereomer 2>90% de.

Both diastereomers were reacted separately with 1-methylpiperazine according to the procedure as described in Example 45. Enantiomeric enriched compounds were obtained after purification using preparative HPLC to afford Example 47a, 2-(4-bromo-2-thienyl)-1-[4-(2-cyclopropylethynyl)-2,6-difluoro-benzoyl]-3-hydroxy-imidazolidin-4-one (isomer 1, less active isomer, 14 mg, 77%) and Example 47b, 2-(4-bromo-2-thienyl)-1-[4-(2-cyclopropylethynyl)-2,6-difluoro-benzoyl]-3-hydroxy-imidazolidin-4-one (isomer 2, most active isomer, 20 mg, 64%). Data: Example 47a LCMS (B) $R_t$: 13.535 min; m/z 510.9/512.9 [M−H+HCOOH]$^−$ (bromide pattern). Example 47b LCMS (B) $R_t$: 13.520 min; m/z 510.9/512.9 [M−H+HCOOH]$^−$ (bromide pattern).

Separation of Enantiomers of Example 8

Example 48a and Example 48b 2-(4-Bromo-2-thienyl)-1-(2,6-difluorobenzoyl)-3-hydroxy-imidazolidin-4-one (isomer 1 and isomer 2)

These diastereomers were prepared in an analogous manner as described for Example 45a and 45b starting from 2-(4-bromo-2-thienyl)-1-(2,6-difluorobenzoyl)-3-hydroxy-imidazolidin-4-one (Example 8) and (2S)-2-phenylbutanoic acid.

The mixture of the two diastereomers was separated by column chromatography (toluene/ethyl acetate=97/3 v/v % isocratic) to afford the two separate diastereomers (diastereomer 1, first eluting from the column obtained in 310 mg (yield: 33%) and diastereomer 2, last eluting in 379 mg (yield: 40.6%)). $^1$H-NMR showed for diastereomer 1>90% de and for diastereomer 2>90% de.

Both diastereomers were reacted separately with 1-methylpiperazine according to the procedure as described in Example 45. Enantiomeric enriched compounds were obtained after purification using preparative HPLC to afford Example 48a, 2-(4-bromo-2-thienyl)-1-(2,6-difluorobenzoyl)-3-hydroxy-imidazolidin-4-one (isomer 1, less active isomer, 290 mg, 85%) and Example 48b, 2-(4-bromo-2-thienyl)-1-(2,6-difluorobenzoyl)-3-hydroxy-imidazolidin-4-one (isomer 2, most active isomer, 210 mg, 77%). Data: Example 48a LCMS (B) $R_t$: 9.551 min; m/z 446.9/448.8 [M−H+HCOOH]$^−$ (bromide pattern). Example 48b LCMS (B) $R_t$: 9.595 min; m/z 446.9/448.8 [M−H+HCOOH]$^−$ (bromide pattern).

Separation of Enantiomers of Example 4

Example 49a and Example 49b 2-(5-Bromo-2-thienyl)-1-(2,6-difluorobenzoyl)-3-hydroxy-imidazolidin-4-one (isomer 1 and isomer 2)

These diastereomers were prepared in an analogous manner as described for Example 45a and 45b starting from 2-(5-bromo-2-thienyl)-1-(2,6-difluorobenzoyl)-3-hydroxy-imidazolidin-4-one (Example 4) and (2S)-2-phenylbutanoic acid.

The mixture of the two diastereomers was separated by column chromatography (toluene/ethyl acetate=96/4 v/v % isocratic) to afford the two separate diastereomers (diastereomer 1, first eluting from the column obtained in 38 mg (yield: 27%) and diastereomer 2, last eluting in 42 mg (yield: 49%)). $^1$H-NMR showed for diastereomer 1>90% de and for diastereomer 2>90% de.

Both diastereomers were reacted separately with 1-methylpiperazine according to the procedure as described in Example 45. Enantiomeric enriched compounds were obtained after purification using preparative HPLC to afford Example 49a, 2-(5-bromo-2-thienyl)-1-(2,6-difluorobenzoyl)-3-hydroxy-imidazolidin-4-one (isomer 1, less active isomer, 19 mg, 67%) and Example 49b, 2-(5-bromo-2-thienyl)-1-(2,6-difluorobenzoyl)-3-hydroxy-imidazolidin-4-one (isomer 2, most active isomer, 19 mg, 67%). Data: Example 49a LCMS (B) $R_t$: 9.824 min; m/z 446.9/448.8 [M−H+HCOOH]⁻ (bromide pattern). Example 49b LCMS (B) $R_t$: 9.825 min; m/z 446.8/448.8 [M−H+HCOOH]⁻ (bromide pattern).

Example 50

2-(4-Bromo-2-thienyl)-1-[2,6-difluoro-4-(3-methylbut-1-ynyl)benzoyl]-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-4-(3-methylbut-1-ynyl)benzoic acid (Intermediate 7). Purification was performed using preparative HPLC to afford the title compound (32 mg, 45%). Data: LCMS (B) $R_t$: 14.513 min; m/z 513.0/515.0 [M−H+HCOOH]⁻ (bromide pattern).

Example 51

2-(4-Bromo-2-thienyl)-1-(2,6-difluoro-4-m ethoxybenzoyl)-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-4-methoxybenzoic acid. Purification was performed using preparative HPLC to afford the title compound (14 mg, 32%). Data: LCMS (B) $R_t$: 10.322 min; m/z 476.9/478.9 [M−H+HCOOH]⁻ (bromide pattern).

Example 52

1-(4-Bromo-2,6-difluoro-benzoyl)-2-(4-bromo-2-thienyl)-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 4-bromo-2,6-difluorobenzoic acid. Purification was performed using preparative HPLC to afford the title compound (13 mg, 27%). Data: LCMS (B) $R_t$: 11.692 min; m/z 524.8/526.8 [M−H+HCOOH]⁻ (dibromide pattern).

Example 53

1-(4-Benzylbenzoyl)-2-(4-bromo-2-thienyl)-3-hydroxy-imidazolidin-4-one

This compound was prepared in an analogous manner as described for Example 1 and Example 38a starting from 2-(4-bromo-2-thienyl)-3-hydroxy-imidazolidin-4-one (Intermediate 2) and 4-benzylbenzoic acid. Purification was performed using preparative HPLC to afford the title compound (16 mg, 35%). Data: LCMS (B) $R_t$: 13.338 min; m/z 501.0/503.0 [M−H+HCOOH]⁻ (bromide pattern).

Example 54

2-(4-Bromo-2-thienyl)-3-hydroxy-1-(4-phenoxybenzoyl)imidazolidin-4-one

This compound was prepared in an analogous manner as described for Example 1 and Example 38a starting from 2-(4-bromo-2-thienyl)-3-hydroxy-imidazolidin-4-one (Intermediate 2) and p-phenoxy benzoic acid. Purification was performed using preparative HPLC to afford the title compound (19 mg, 41%). Data: LCMS (B) $R_t$: 12.998 min; m/z 502.9/505.0 [M−H+HCOOH]⁻ (bromide pattern).

Example 55

2-(4-Bromo-2-thienyl)-1-(2-chlorobenzoyl)-3-hydroxy-imidazolidin-4-one

This compound was prepared in an analogous manner as described for Example 1 starting from 2-(4-bromo-2-thienyl)-3-hydroxy-imidazolidin-4-one (Intermediate 2) and 2-chlorobenzoyl chloride. Purification was performed using preparative HPLC to afford the title compound (13 mg, 32%). Data: LCMS (B) $R_t$: 9.888 min; m/z 444.9/446.9 [M−H+HCOOH]⁻ (bromide/chloride pattern).

Example 56

2-(4-Bromo-2-thienyl)-3-hydroxy-1-[2-(trifluoromethyl)benzoyl]imidazolidin-4-one This compound was prepared in an analogous manner as described for Example 1 starting from 2-(4-bromo-2-thienyl)-3-hydroxy-imidazolidin-4-one (Intermediate 2) and 2-(trifluoromethyl)benzoyl chloride. Purification was performed using preparative HPLC to afford the title compound (10 mg, 23%). Data: LCMS (B) $R_t$: 10.745 min; m/z 478.9/480.9 [M−H+HCOOH]⁻ (bromide pattern).

Example 57

2-(4-Bromo-2-thienyl)-1-(fu ran-3-carbonyl)-3-hydroxy-imidazolidin-4-one

This compound was prepared in an analogous manner as described for Example 1 and Example 38a starting from 2-(4-bromo-2-thienyl)-3-hydroxy-imidazolidin-4-one (Intermediate 2) and 3-furoic acid. Purification was performed using preparative HPLC to afford the title compound (17 mg, 47%). Data: LCMS (B) $R_t$: 8.112 min; m/z 356.9/358.9 [M+H]⁺ (bromide pattern).

Example 58

2-(4-Bromo-2-thienyl)-3-hydroxy-1-(thiophene-2-carbonyl)imidazolidin-4-one

This compound was prepared in an analogous manner as described for Example 1 and Example 38a starting from 2-(4-bromo-2-thienyl)-3-hydroxy-imidazolidin-4-one (Intermediate 2) and thiophene-2-carboxylic acid. Purification was performed using preparative HPLC to afford the title compound (13 mg, 35%). Data: LCMS (B) $R_t$: 9.154 min; m/z 372.9/374.9 [M+H]$^+$ (bromide pattern).

Example 59

2-(4-Bromo-2-thienyl)-1-(cyclopropanecarbonyl)-3-hydroxy-imidazolidin-4-one

This compound was prepared in an analogous manner as described for Example 1 and Example 38a starting from 2-(4-bromo-2-thienyl)-3-hydroxy-imidazolidin-4-one (Intermediate 2) and cyclopropanecarboxylic acid. Purification was performed using preparative HPLC to afford the title compound (10 mg, 30%). Data: LCMS (B) $R_t$: 7.515 min; m/z 330.9/333.0 [M+H]$^+$ (bromide pattern).

Example 60

2-(4-Bromo-2-thienyl)-1-(cyclobutanecarbonyl)-3-hydroxy-imidazolidin-4-one

This compound was prepared in an analogous manner as described for Example 1 and Example 38a starting from 2-(4-bromo-2-thienyl)-3-hydroxy-imidazolidin-4-one (Intermediate 2) and cyclobutanecarboxylic acid. Purification was performed using preparative HPLC to afford the title compound (9 mg, 26%). Data: LCMS (B) $R_t$: 8.793 min; m/z 388.9/391.0 [M−H+HCOOH]$^−$ (bromide pattern).

Example 61

2-(4-Bromo-2-thienyl)-1-(2-fluoro-2-methyl-propanoyl)-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2-fluoroisobutyric acid. Purification was performed using preparative HPLC to afford the title compound (6 mg, 17%). Data: LCMS (B) $R_t$: 9.063 min; m/z 351.0/353.0 [M+H]$^+$ (bromide pattern).

Example 62

(Trans)-2-(4-bromo-2-thienyl)-3-hydroxy-1-(4-phenylcyclohexanecarbonyl)imidazolidin-4-one This compound was prepared in an analogous manner as described for Example 1 and Example 38a starting from 2-(4-bromo-2-thienyl)-3-hydroxy-imidazolidin-4-one (Intermediate 2) and trans-4-phenylcyclohexanecarboxylic acid. Purification was performed using preparative HPLC to afford the title compound (17 mg, 38%). Data: LCMS (B) $R_t$: 13.565 min; m/z 449.0/451.0 [M+H]$^+$ (bromide pattern).

Example 63

2-(4-Bromo-2-thienyl)-3-hydroxy-1-(2,3,4,5,6-pentafluorobenzoyl)imidazolidin-4-one This compound was prepared in an analogous manner as described for Example 1 starting from 2-(4-bromo-2-thienyl)-3-hydroxy-imidazolidin-4-one (Intermediate 2) and pentafluorobenzoyl chloride. Purification was performed using preparative HPLC to afford the title compound (12 mg, 26%). Data: LCMS (B) $R_t$: 12.145 min; m/z 500.9/502.9 [M−H+HCOOH]$^−$ (bromide pattern).

Example 64

2-(4-Bromo-2-thienyl)-1-[2-fluoro-4-(trifluoromethyl)benzoyl]-3-hydroxy-imidazolidin-4-one This compound was prepared in an analogous manner as described for Example 1 starting from 2-(4-bromo-2-thienyl)-3-hydroxy-imidazolidin-4-one (Intermediate 2) and 2-fluoro-4-(trifluoromethyl)benzoyl chloride. Purification was performed using preparative HPLC to afford the title compound (22 mg, 49%). Data: LCMS (B) $R_t$: 12.168 min; m/z 496.9/498.9 [M−H+HCOOH]$^−$ (bromide pattern).

Example 65

2-(4-Bromo-2-thienyl)-1-(2-fluoro-6-methyl-benzoyl)-3-hydroxy-imidazolidin-4-one This compound was prepared in an analogous manner as described for Example 1 starting from 2-(4-bromo-2-thienyl)-3-hydroxy-imidazolidin-4-one (Intermediate 2) and 2-fluoro-6-methylbenzoyl chloride. Purification was performed using preparative HPLC to afford the title compound (8 mg, 20%). Data: LCMS (B) $R_t$: 10.126 min; m/z 442.9/444.9 [M−H+HCOOH]$^−$ (bromide pattern).

Example 66

2-(4-Bromo-2-thienyl)-1-(2-chloropyridine-3-carbonyl)-3-hydroxy-imidazolidin-4-one This compound was prepared in an analogous manner as described for Example 1 starting from 2-(4-bromo-2-thienyl)-3-hydroxy-imidazolidin-4-one (Intermediate 2) and 2-chloropyridine-3-carbonyl chloride. Purification was performed using preparative HPLC to afford the title compound (8 mg, 20%). Data: LCMS (B) $R_t$: 7.730 min; m/z 401.9/403.9 [M+H]$^+$ (bromide/chloride pattern).

Example 67

2-(4-Bromo-2-thienyl)-1-(cyclohexanecarbonyl)-3-hydroxy-imidazolidin-4-one

This compound was prepared in an analogous manner as described for Example 1 and Example 38a starting from 2-(4-bromo-2-thienyl)-3-hydroxy-imidazolidin-4-one (Intermediate 2) and cyclohexanecarboxylic acid. Purification was performed using preparative HPLC to afford the title compound (5 mg, 13%). Data: LCMS (B) $R_t$: 10.769 min; m/z 417.0/419.0 [M−H+HCOOH]$^−$ (bromide pattern).

Example 68

2-(4-Bromo-2-thienyl)-1-(2,4-dichlorobenzoyl)-3-hydroxy-imidazolidin-4-one

This compound was prepared in an analogous manner as described for Example 1 and Example 38a starting from 2-(4-bromo-2-thienyl)-3-hydroxy-imidazolidin-4-one (Intermediate 2) and 2,4-dichlorobenzoic acid. Purification was performed using preparative HPLC to afford the title com-

Example 69

2-(4-Bromo-2-thienyl)-1-(2,3-dichlorobenzoyl)-3-hydroxy-imidazolidin-4-one

This compound was prepared in an analogous manner as described for Example 1 and Example 38a starting from 2-(4-bromo-2-thienyl)-3-hydroxy-imidazolidin-4-one (Intermediate 2) and 2,3-dichlorobenzoic acid. Purification was performed using preparative HPLC to afford the title compound (14 mg, 32%). Data: LCMS (B) $R_t$: 11.249 min; m/z 478.8/480.8/482.9 [M−H+HCOOH]$^-$ (dichloro/bromide pattern).

Example 70

2-(4-Bromo-2-thienyl)-3-hydroxy-1-[4-(trifluoromethoxy)benzoyl]imidazolidin-4-one This compound was prepared in an analogous manner as described for Example 1 starting from 2-(4-bromo-2-thienyl)-3-hydroxy-imidazolidin-4-one (Intermediate 2) and 4-(trifluoromethoxy)benzoyl chloride. Purification was performed using preparative HPLC to afford the title compound (20 mg, 44%). Data: LCMS (B) $R_t$: 12.295 min; m/z 494.9/496.9 [M−H+HCOOH]$^-$ (bromide pattern).

Example 71

2-(4-Bromo-2-thienyl)-3-hydroxy-1-[4-(4-methylsulfonylphenyl)benzoyl]imidazolidin-4-one This compound was prepared in an analogous manner as described for Example 1 and Example 38a starting from 2-(4-bromo-2-thienyl)-3-hydroxy-imidazolidin-4-one (Intermediate 2) and 4'-(methylsulfonyl)[1,1'-biphenyl]-4-carboxylic acid. Purification was performed using preparative HPLC to afford the title compound (15 mg, 29%). Data: LCMS (B) $R_t$: 10.211 min; m/z 564.9/566.9 [M−H+HCOOH]$^-$ (bromide pattern).

Example 72

2-(4-Bromo-2-thienyl)-3-hydroxy-1-(2-methylbenzoyl)imidazolidin-4-one

This compound was prepared in an analogous manner as described for Example 1 and Example 38a starting from 2-(4-bromo-2-thienyl)-3-hydroxy-imidazolidin-4-one (Intermediate 2) and o-toluic acid. Purification was performed using preparative HPLC to afford the title compound (15 mg, 29%). Data: LCMS (B) $R_t$: 9.661 min; m/z 425.0/426.9 [M−H+HCOOH]$^-$ (bromide pattern).

Example 73

2-(4-Bromo-2-thienyl)-1-(3-fluoropyridine-4-carbonyl)-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 3-fluoroisonicotinic acid. Purification was performed using preparative HPLC to afford the title compound (4 mg, 10%). Data: LCMS (B) $R_t$: 7.318 min; m/z 385.9/397.9 [M+H]$^+$ (bromide pattern).

Example 74

1-(3-Bromo-2,6-difluoro-benzoyl)-2-(4-bromo-2-thienyl)-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 3-bromo-2,6-difluorobenzoic acid. Purification was performed using preparative HPLC to afford the title compound (15 mg, 31%). Data: LCMS (B) $R_t$: 11.010 min; m/z 524.8/526.8/528.8 [M−H+HCOOH]$^-$ (dibromide pattern).

Example 75

2-(4-Bromo-2-thienyl)-1-(2,6-difluoro-3-methoxybenzoyl)-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-3-methoxybenzoic acid. Purification was performed using preparative HPLC to afford the title compound (15 mg, 35%). Data: LCMS (B) $R_t$: 9.649 min; m/z 476.9/478.9 [M−H+HCOOH]$^-$ (bromide pattern).

Example 76

2-(4-Bromo-2-thienyl)-1-[2,6-difluoro-3-(trifluoromethyl)benzoyl]-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-3-(trifluoromethyl)benzoic acid. Purification was performed using preparative HPLC to afford the title compound (6 mg, 15%). Data: LCMS (B) $R_t$: 11.590 min; m/z 514.9/516.9 [M−H+HCOOH]$^-$ (bromide pattern).

Example 77

2-(4-Bromo-2-thienyl)-1-(2,6-difluoro-3-methylbenzoyl)-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-3-methylbenzoic acid. Purification was performed using preparative HPLC to afford the title compound (19 mg, 45%). Data: LCMS (B) $R_t$: 10.383 min; m/z 460.9/462.9 [M−H+HCOOH]$^-$ (bromide pattern).

Example 78

2-(4-Bromo-2-thienyl)-1-[4-(2-cyclohexylethynyl)-2,6-difluoro-benzoyl]-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 4-(2-cyclohexylethynyl)-2,6-difluorobenzoic acid (Intermediate 8). Purification was performed using preparative HPLC to afford the title compound (17 mg, 33%). Data: LCMS (B) $R_t$: 16.877 min; m/z 553.0/554.9 [M−H+HCOOH]− (bromide pattern).

Example 79

1-[4-(3-Aminoprop-1-ynyl)-2,6-difluoro-benzoyl]-2-(4-bromo-2-thienyl)-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 4-[3-(tert-butoxycarbonylamino)prop-1-ynyl]-2,6-difluoro-benzoic acid (Intermediate 10). Purification was performed, after Boc-deprotection, using preparative HPLC to afford the title compound (18 mg, 49%). Data: LCMS (B) $R_t$: 5.579 min; m/z 455.9/457.9 [M+H]+ (bromide pattern).

Example 80

2-(4-Bromo-2-thienyl)-1-[2,6-difluoro-4-[3-(sulfamoylamino)prop-1-ynyl] benzoyl]-3-hydroxy-4-oxo-imidazolidine This compound was prepared in an analogous manner as described for Example 1 and Example 38a starting from 2-(4-bromo-2-thienyl)-3-hydroxy-imidazolidin-4-one (Intermediate 2) and 4-[3-(tert-butoxycarbonylsulfamoylamino)prop-1-ynyl]-2,6-difluoro-benzoic acid (Intermediate 11). Purification was performed, after Boc-deprotection, using preparative HPLC to afford the title compound (11 mg, 68%). Data: LCMS (B) $R_t$: 8.757 min; m/z 578.9/580.9 [M−H+HCOOH]− (bromide pattern).

Example 81

1-[4-(3-Amino-3-methyl-but-1-ynyl)-2,6-difluoro-benzoyl]-2-(4-bromo-2-thienyl)-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 4-[3-(tert-butoxycarbonylamino)-3-methyl-but-1-ynyl]-2,6-difluoro-benzoic acid (Intermediate 12). Purification was performed, after Boc-deprotection, using preparative HPLC to afford the title compound (17 mg, 58%). Data: LCMS (B) $R_t$: 6.576 min; m/z 466.9/468.9 [M+H]+ (bromide pattern).

Example 82

2-(4-Bromo-2-thienyl)-1-(4-cyclopropyl-2,6-difluoro-benzoyl)-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 4-cyclopropyl-2,6-difluoro-benzoic acid (Intermediate 13). Purification was performed using preparative HPLC to afford the title compound (15 mg, 34%). Data: LCMS (B) $R_t$: 11.912 min; m/z 486.9/488.9 [M−H+HCOOH]− (bromide pattern).

Example 83

2-(4-Bromo-2-thienyl)-1-(2,6-difluoro-4-vinyl-benzoyl)-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-4-vinyl-benzoic acid (Intermediate 14). Purification was performed using preparative HPLC to afford the title compound (9 mg, 21%). Data: LCMS (B) $R_t$: 11.380 min; m/z 472.9/474.9 [M−H+HCOOH]− (bromide pattern).

Example 84

2-(4-Bromo-2-thienyl)-1-(2,6-difluoro-4-methyl-benzoyl)-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-4-methyl-benzoic acid (Intermediate 15). Purification was performed using preparative HPLC to afford the title compound (16 mg, 38%). Data: LCMS (B) $R_t$: 10.692 min; m/z 460.9/462.9 [M−H+HCOOH]− (bromide pattern).

Example 85

2-(4-Bromo-2-thienyl)-1-(2,6-difluoro-4-phenyl-benzoyl)-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-4-phenyl-benzoic acid (Intermediate 16). Purification was performed using preparative HPLC to afford the title compound (18 mg, 38%). Data: LCMS (B) $R_t$: 13.294 min; m/z 522.9/524.9 [M−H+HCOOH]− (bromide pattern).

Example 86

2-(4-Bromo-2-thienyl)-1-[2,6-difluoro-4-(1-methylpyrazol-4-yl)benzoyl]-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-4-(1-methylpyrazol-4-yl)benzoic acid (Intermediate 17). Purification was performed using preparative HPLC to afford the title compound (8 mg, 16%). Data: LCMS (B) $R_t$: 9.432 min; m/z 482.9/484.9 [M+H]+ (bromide pattern).

Example 87

2-(4-Bromo-2-thienyl)-1-[2,6-difluoro-4-(2-thienyl)benzoyl]-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-4-(2-thienyl)benzoic acid (Intermediate 18). Purification was performed using prepara-

Example 88

2-(4-Bromo-2-thienyl)-1-[2,6-difluoro-4-(3-pyridyl) benzoyl]-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-4-(3-pyridyl)benzoic acid (Intermediate 19). Purification was performed using preparative HPLC to afford the title compound (13 mg, 27%). Data: LCMS (B) $R_t$: 8.178 min; m/z 479.9/481.9 [M+H]$^+$ (bromide pattern).

Example 89

1-[4-[2-(1-Aminocyclopropyl)ethynyl]-2,6-difluoro-benzoyl]-2-(4-bromo-2-thienyl)-3-hydroxy-imidazolidin-4-one This compound was prepared from Intermediate B and 4-[2-[1-(tert-butoxycarbonylamino)cyclopropyl]ethynyl]-2,6-difluoro-benzoic acid (Intermediate 20) according to procedures described in Example 2. Purification was performed, after Boc-deprotection, using preparative HPLC to afford the title compound (2 mg, 5%). Data: LCMS (B) $R_t$: 6.919 min; m/z 482.0/484.0 [M+H]$^+$ (bromide pattern).

Example 90

2-(4-Bromo-2-thienyl)-1-[2,6-difluoro-4-[2-[1-(sulfamoylamino)cyclopropyl]ethynyl]benzoyl]-3-hydroxy-4-oxo-imidazolidine This compound was prepared from Intermediate B and 4-[2-[1-(tert-butoxycarbonylsulfamoylamino)cyclopropyl]ethynyl]-2,6-difluoro-benzoic acid (Intermediate 21) according to procedures described in Example 2. Purification was performed, after Boc-deprotection, using preparative HPLC to afford the title compound (4 mg, 10%). Data: LCMS (B) $R_t$: 9.712 min; m/z 604.9/606.9 [M+H]$^+$ (bromide pattern).

Example 91

N-[[4-[2-(4-Bromo-2-thienyl)-3-hydroxy-4-oxo-imidazolidine-1-carbonyl]-3,5-difluoro-phenyl] methyl]methanesulfonamide This compound was prepared in an analogous manner as described for Example 1 and Example 38a starting from 2-(4-bromo-2-thienyl)-3-hydroxy-imidazolidin-4-one (Intermediate 2) and 2,6-difluoro-4-(methanesulfonamidoethyl)benzoic acid (Intermediate 22). Purification was performed using preparative HPLC to afford the title compound (7 mg, 13%). Data: LCMS (B) $R_t$: 8.212 min; m/z 509.9/511.9 [M–H+HCOOH]$^-$ (bromide pattern).

Example 92

2-(4-Bromo-2-thienyl)-1-[4-(2-cyclohexylethyl)-2,6-difluoro-benzoyl]-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 4-(2-cyclohexylethyl)-2,6-difluoro-benzoic acid (Intermediate 23). Purification was performed using preparative HPLC to afford the title compound (0.6 mg). Data: LCMS (B) $R_t$: 17.607 min; m/z 557.0/559.0 [M–H+HCOOH]$^-$ (bromide pattern).

Example 93

2-(4-Bromo-2-thienyl)-1-[2,6-difluoro-4-[3-(sulfamoylamino)propyl] benzoyl]-3-hydroxy-4-oxo-imidazolidine This compound was prepared in an analogous manner as described for Example 1 and Example 38a starting from 2-(4-bromo-2-thienyl)-3-hydroxy-imidazolidin-4-one (Intermediate 2) and 4-[3-(tert-butoxycarbonylsulfamoylamino)propyl]-2,6-difluoro-benzoic acid (Intermediate 24). Purification was performed, after Boc-deprotection, using preparative HPLC to afford the title compound (12 mg, 37%). Data: LCMS (B) $R_t$: 8.569 min; m/z 538.9/540.9 [M+H]$^+$ (bromide pattern).

Example 94

2-(4-Bromo-2-thienyl)-1-[2,6-difluoro-4-[3-methyl-but-1-enyl]benzoyl]-3-hydroxy-imidazolidin-4-one (mixture of E and Z isomers)

This compound was prepared in an analogous manner as described for Example 1 and Example 38a starting from 2-(4-bromo-2-thienyl)-3-hydroxy-imidazolidin-4-one (Intermediate 2) and a 7:3 mixture of 2,6-difluoro-4-(3-methylbut-1-enyl)benzoic acid and 2,6-difluoro-4-isopentyl-benzoic acid (Intermediate 25). Purification was performed using preparative HPLC to afford the title compound as a 1:1 mixture of E and Z isomer (5 mg, 5%). Data: LCMS (B) $R_t$: 14.594/14.729 min; m/z 514.9/517.0 [M–H+HCOOH]$^-$ (bromide pattern).

Example 95

2-(4-Bromo-2-thienyl)-1-(2,6-difluoro-4-isopentyl-benzoyl)-3-hydroxy-imidazolidin-4-one This compound was isolated as a side-product during prep HPLC purification of Example 94 (25 mg, 25%). Data: LCMS (B) $R_t$: 15.196 min; m/z 517.0/519.0 [M–H+HCOOH]$^-$ (bromide pattern).

Example 96

2-(4-bromo-2-thienyl)-1-[2,6-difluoro-4-(1H-pyrazol-4-yl)benzoyl]-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 4-(1-tert-butoxycarbonylpyrazol-4-yl)-2,6-difluoro-benzoic acid (Intermediate 26). Purification was performed, after Boc-deprotection, using preparative HPLC to afford the title compound (1.3 mg, 34%). Data: LCMS (B) $R_t$: 8.486 min; m/z 466.9/468.9 [M–H+HCOOH]$^-$ (bromide pattern).

Example 97

2-(4-Bromo-2-thienyl)-1-[4-(dimethylamino)-2,6-difluoro-benzoyl]-3-hydroxy-imidazolidin-4-one This compound was prepared from Intermediate B and 4-(dimethylamino)-2,6-difluoro-benzoic acid (Intermediate 27) according to procedures described in Example 2. Purification was performed using preparative HPLC to afford the title compound (2 mg, 6%). Data: LCMS (B) $R_t$: 10.822 min; m/z 489.9/491.9 [M−H+HCOOH]$^-$ (bromide pattern).

Example 98

2-(5-Bromo-3-thienyl)-1-(2-fluorobenzoyl)-3-hydroxy-imidazolidin-4-one

This compound was prepared in an analogous manner as described for Example 1 starting from 2-(5-bromo-3-thienyl)-3-hydroxy-imidazolidin-4-one (Intermediate 28) and 2-fluorobenzoyl chloride. Purification was performed using preparative HPLC to afford the title compound (13 mg, 28%). Data: LCMS (B) $R_t$: 9.028 min; m/z 428.9/430.9 [M−H+HCOOH]$^-$ (bromide pattern).

Example 99

2-(5-Bromo-3-thienyl)-1-(2-chloro-6-fluoro-benzoyl)-3-hydroxy-imidazolidin-4-one This compound was prepared in an analogous manner as described for Example 1 starting from 2-(5-bromo-3-thienyl)-3-hydroxy-imidazolidin-4-one (Intermediate 28) and 2-chloro-6-fluorobenzoyl chloride. Purification was performed using preparative HPLC to afford the title compound (24 mg, 47%). Data: LCMS (B) $R_t$: 9.637 min; m/z 462.8/464.9 [M−H+HCOOH]$^-$ (bromide/chloride pattern).

Example 100

2-(5-Bromo-3-thienyl)-1-[2-fluoro-6-(trifluoromethyl)benzoyl]-3-hydroxy-imidazolidin-4-one This compound was prepared in an analogous manner as described for Example 1 starting from 2-(5-bromo-3-thienyl)-3-hydroxy-imidazolidin-4-one (Intermediate 28) and 2-fluoro-6-(trifluoromethyl)benzoyl chloride. Purification was performed using preparative HPLC to afford the title compound (16 mg, 27%). Data: LCMS (B) $R_t$: 10.480 min; m/z 496.9/498.9 [M−H+HCOOH]$^-$ (bromide pattern).

Example 101

1-(3-Bromo-2,6-difluoro-benzoyl)-2-(5-bromo-3-thienyl)-3-hydroxy-imidazolidin-4-one This compound was prepared in an analogous manner as described for Example 1 and Example 38a starting from 2-(5-bromo-3-thienyl)-3-hydroxy-imidazolidin-4-one (Intermediate 28) and 3-bromo-2,6-difluorobenzoic acid. Purification was performed using preparative HPLC to afford the title compound (16.7 mg, 35%). Data: LCMS (B) $R_t$: 10.797 min; m/z 524.8/526.8/528.8 [M−H+HCOOH]$^-$ (dibromide pattern).

Example 102

2-(5-Bromo-3-thienyl)-1-(2,6-difluoro-3-methyl-benzoyl)-3-hydroxy-imidazolidin-4-one This compound was prepared in an analogous manner as described for Example 1 and Example 38a starting from 2-(5-bromo-3-thienyl)-3-hydroxy-imidazolidin-4-one (Intermediate 28) and 2,6-difluoro-3-methylbenzoic acid. Purification was performed using preparative HPLC to afford the title compound (11.3 mg, 27%). Data: LCMS (B) $R_t$: 10.216 min; m/z 460.9/462.9 [M−H+HCOOH]$^-$ (bromide pattern).

Example 103

2-(5-Bromo-3-thienyl)-1-[2,6-difluoro-3-(trifluoromethyl)benzoyl]-3-hydroxy-imidazolidin-4-one This compound was prepared in an analogous manner as described for Example 1 and Example 38a starting from 2-(5-bromo-3-thienyl)-3-hydroxy-imidazolidin-4-one (Intermediate 28) and 2,6-difluoro-3-(trifluoromethyl)benzoic acid. Purification was performed using preparative HPLC to afford the title compound (19.6 mg, 41%). Data: LCMS (B) $R_t$: 11.390 min; m/z 514.9/516.9 [M−H+HCOOH]$^-$ (bromide pattern).

Example 104

2-(5-Bromo-3-thienyl)-1-(2,6-difluoro-3-methoxy-benzoyl)-3-hydroxy-imidazolidin-4-one This compound was prepared in an analogous manner as described for Example 1 and Example 38a starting from 2-(5-bromo-3-thienyl)-3-hydroxy-imidazolidin-4-one (Intermediate 28) and 2,6-difluoro-3-methoxybenzoic acid. Purification was performed using preparative HPLC to afford the title compound (18 mg, 41%). Data: LCMS (B) $R_t$: 9.467 min; m/z 476.9/478.9 [M−H+HCOOH]$^-$ (bromide pattern).

Example 105

1-(3-Amino-2,6-difluoro-benzoyl)-2-(4-bromo-2-thienyl)-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 3-amino-2,6-difluorobenzoic acid. Purification was performed using preparative HPLC to afford the title compound (5 mg, 12%). Data: LCMS (B) $R_t$: 8.035 min; m/z 461.9/463.9 [M−H+HCOOH]$^-$ (bromide pattern).

Example 106

2-(4-Bromo-2-thienyl)-1-(2,6-difluoro-3-nitro-benzoyl)-3-hydroxy-imidazolidin-4-one This compound was prepared from Intermediate B and 2,6-difluoro-3-nitrobenzoic acid according to procedures described in Example 2 and Example 38b. Purification was performed using preparative HPLC to afford the title compound (11 mg, 27%). Data: LCMS (B) R$_t$: 10.131 min; m/z 491.9/493.9 [M−H+HCOOH]$^−$ (bromide pattern).

Example 107

N-[3-[2-(4-bromo-2-thienyl)-3-hydroxy-4-oxo-imidazolidine-1-carbonyl]-2,4-difluoro-phenyl]methanesulfonamide This compound was prepared in an analogous manner as described for Example 1 and Example 38a starting from 2-(4-bromo-2-thienyl)-3-hydroxy-imidazolidin-4-one (Intermediate 2) and 2,6-difluoro-3-(methanesulfonamido)benzoic acid. Purification was performed using preparative HPLC to afford the title compound (18 mg, 36%). Data: LCMS (B) R$_t$: 8.289 min; m/z 493.9/495.9 [M−H]$^−$ (bromide pattern).

Example 108

4-[2-(4-Bromo-2-thienyl)-3-hydroxy-4-oxo-imidazolidine-1-carbonyl]piperidine-1-sulfonamide This compound was prepared in an analogous manner as described for Example 1 and Example 38a starting from 2-(4-bromo-2-thienyl)-3-hydroxy-imidazolidin-4-one (Intermediate 2) and 1-(tert-butoxycarbonylsulfamoyl)piperidine-4-carboxylic acid. Purification was performed, after Boc-deprotection, using preparative HPLC to afford the title compound (6 mg, 13%). Data: LCMS (B) R$_t$: 6.268 min; m/z 452.9/455.0 [M+H]$^+$ (bromide pattern).

Example 109

2-(4-Cyclopropyl-2-thienyl)-1-(2,6-difluorobenzoyl)-3-hydroxy-imidazolidin-4-one (a) 2-(4-Cyclopropyl-2-thienyl)-1,3-dioxolane (4-Bromo-2-thienyl)methanol (100 mg, 0.4 mmol), tricyclohexylphosphine (34 mg, 0.12 mmol), cesium carbonate (780 mg, 2.4 mmol) and cyclopropylboronic acid methyliminodiacetic acid anhydride (180 mg, 0.91 mmol) were dissolved in toluene/water=5/1 v/v % (6 mL) and the solution was degassed with nitrogen for 5 minutes. Palladium (II)acetate (13.4 mg, 0.06 mmol) was added under nitrogen atmosphere and the reaction mixture was refluxed at 100° C. for 3 hours. The crude reaction mixture was filtered over Decalite™. The filtrate was diluted with ethyl acetate and washed with water, brine, dried over sodium sulfate, filtered and concentrated under reduced pressure to afford the crude title compound (130 mg, yield: 73%).

(b) 4-Cyclopropylthiophene-2-carbaldehyde

To a solution of 2-(4-cyclopropyl-2-thienyl)-1,3-dioxolane (130 mg, 0.66 mmol) in THF (4 mL) was added 1M HCl-solution (4 mL) and the reaction mixture was stirred for 1 h at room temperature. The mixture was extracted with ethyl acetate (3×10 mL). The combined organic layers were washed with water (2×20 mL), brine (20 mL), dried (Na$_2$SO$_4$), filtered and concentrated in vacuo. The crude residue was purified by column chromatography (heptane to ethyl acetate=0 to 30 v/v %) to afford the title compound (55 mg, 55%).

(c) 3-Benzyloxy-2-(4-cyclopropyl-2-thienyl)-1-(2,6-difluorobenzoyl)imidazolidin-4-one To a suspension of 2-amino-N-benzyloxy-acetamide 2,2,2-trifluoroacetic acid (106 mg, 0.36 mmol) in acetonitril (1.8 mL) was added subsequently DiPEA (60 µL, 0.36 mmol) and 4-cyclopropylthiophene-2-carbaldehyde (55 mg, 0.36 mmol). The reaction mixture was refluxed for 1 h. The mixture was cooled (4° C.) and additional DiPEA (60 µL, 0.36 mmol) was added. A solution of 2,6-difluorobenzoyl-chloride (54 µL, 0.43 mmol) in acetonitrile (0.2 mL) was added drop-wise. The mixture was stirred at 4° C. for 1 h. Ethyl acetate was added and the mixture was washed with water and brine. The organic layer was separated, dried over sodium sulfate, filtered and concentrated under reduced pressure. The crude residue was purified by column chromatography (heptane/ethyl acetate=10/0 to 1/1 v/v %) to afford the title compound (74 mg, 45%).

(d) 2-(4-Cyclopropyl-2-thienyl)-1-(2,6-difluorobenzoyl)-3-hydroxy-imidazolidin-4-one (Example 109)

10% Palladium on charcoal (20 mg) was added to a solution of 3-benzyloxy-2-(4-cyclopropyl-2-thienyl)-1-(2,6-difluorobenzoyl)imidazolidin-4-one (74 mg, 0.16 mmol) in ethyl acetate (10 mL). The mixture was hydrogenated at atmospheric pressure at room temperature for 1 h. The palladium catalyst was removed by filtration and the solvent was removed by evaporation at reduced pressure. Purification was performed using preparative HPLC to afford the title compound (38 mg, 65%). Data: LCMS (B) R$_t$: 9.720 min; m/z 409.0 [M−H+HCOOH]+.

Separation of Enantiomers of Example 37

Example 110a and Example 110b 2-(4-Bromo-5-fluoro-2-thienyl)-1-(2,6-difluorobenzoyl)-3-hydroxy-imidazolidin-4-one (isomer 1 and isomer 2)

These diastereomers were prepared in an analogous manner as described for Example 45a and 45b starting from 2-(4-Bromo-5-fluoro-2-thienyl)-1-(2,6-difluorobenzoyl)-3-hydroxy-imidazolidin-4-one (Example 37) and (2R)-2-phenylbutanoic acid.

The mixture of the two diastereomers was separated by column chromatography (heptane/ethyl acetate=7/3 v/v % isocratic) to afford the two separate diastereomers (diastereomer 1, first eluting from the column obtained in 12 mg (yield: 42%) and diastereomer 2, last eluting in 8 mg (yield: 31%)). $^1$H-NMR showed for diastereomer 1>90% de and for diastereomer 2>90% de.

Both diastereomers were reacted separately with 1-methylpiperazine according to the procedure as described in Example 45. Enantiomeric enriched compounds were obtained after purification using preparative HPLC to afford Example 110a, 2-(4-Bromo-5-fluoro-2-thienyl)-1-(2,6-difluorobenzoyl)-3-hydroxy-imidazolidin-4-one (isomer 1, most active isomer, 11 mg, quant.) and Example 110b, 2-(4-bromo-2-thienyl)-1-(2,6-difluorobenzoyl)-3-hydroxy-imidazolidin-4-one (isomer 2, less active isomer, 8 mg, quant.). Data: Example 110a LCMS (B) R$_t$: 10.529 min; m/z 464.9/466.9 [M−H+HCOOH]$^−$ (bromide pattern). Example 110b LCMS (B) R$_t$: 10.551 min; m/z 464.9/466.9 [M−H+HCOOH]$^−$ (bromide pattern).

Example 111

2-(4-Bromo-5-deuterio-2-thienyl)-1-(2,6-difluorobenzoyl)-3-hydroxy-imidazolidin-4-one This compound was prepared in an analogous manner as described for Example 1 starting from 2-(4-bromo-5-deuterio-2-thienyl)-3-hydroxy-imidazolidin-4-one (Intermediate 29) and 2,6-difluorobenzoyl chloride. Purification was performed using preparative HPLC to afford the title compound (10 mg, 15%). Data: LCMS (B) $R_t$: 9.475 min; m/z 447.9/449.9 [M−H+HCOOH]⁻ (bromide pattern).

Example 112

2-(5-Chloro-4-methyl-2-thienyl)-1-(2,6-difluorobenzoyl)-3-hydroxy-imidazolidin-4-one (a) 5-Chloro-4-methyl-thiophene-2-carbaldehyde To a mixture of DMF (1.76 mL, 22.6 mmol) in DCM (5 mL) was added drop-wise a solution of phosphoroxychlorid (1.40 mL, 15.1 mmol) in DCM (5 mL) and the reaction mixture was stirred at room temperature for 1 h. 2-Chloro-3-methylthiophene (1.00 g, 7.54 mmol) was added and the reaction mixture was heated under reflux for 2 h. The reaction mixture was diluted with DCM and a sat. NaHCO₃-solution was added carefully. The waterlayer was separated and extracted with DCM. The combined organic layers were washed with 5% NaHCO₃-solution, water, dried (Na₂SO₄), filtered and concentrated. The crude residue was purified by column chromatography (heptane to ethyl acetate=0 to 30 v/v %) to afford the title compound (183 mg).

(b) 2-(5-Chloro-4-methyl-2-thienyl)-1-(2,6-difluorobenzoyl)-3-hydroxy-imidazolidin-4-one This compound was prepared in an analogous manner as described for Example 109c and Example 2b starting from 5-chloro-4-methyl-thiophene-2-carbaldehyde and 2,6-difluorobenzoyl chloride. Purification was performed, using preparative HPLC to afford the title compound (44 mg, 54%). Data: LCMS (B) $R_t$: 10.409 min; m/z 417.0/419.0 [M−H+HCOOH]⁻ (chloride pattern).

Example 113

2-(4-bromo-5-methyl-2-thienyl)-1-(2,6-difluorobenzoyl)-3-hydroxy-imidazolidin-4-one This compound was prepared in an analogous manner as described for Example 109c and Example 2b starting from 4-bromo-5-methyl-thiophene-2-carbaldehyde (Intermediate 30) and 2,6-difluorobenzoyl chloride. Purification was performed using preparative HPLC to afford the title compound (49 mg, 54%). Data: LCMS (B) $R_t$: 10.451 min; m/z 460.9/462.9 [M−H+HCOOH]⁻ (bromide pattern).

Example 114

2-[4-Bromo-5-(trideuteriomethyl)-2-thienyl]-1-(2,6-difluorobenzoyl)-3-hydroxy-imidazolidin-4-one This compound was prepared in an analogous manner as described for Example 109c and Example 2b starting from 4-bromo-5-(trideuteriomethyl)thiophene-2-carbaldehyde (Intermediate 31) and 2,6-difluorobenzoyl chloride. Purification was performed using preparative HPLC to afford the title compound (84 mg, 62%). Data: LCMS (B) $R_t$: 10.379 min; m/z 463.9/465.9 [M−H+HCOOH]⁻ (bromide pattern).

Example 115

2-(4-Bromo-5-chloro-2-thienyl)-1-(2,6-difluorobenzoyl)-3-hydroxy-imidazolidin-4-one This compound was prepared in an analogous manner as described for Example 109c and Example 2b starting from 4-bromo-5-chloro-thiophene-2-carbaldehyde (prepared according to Badland et al, Bioorg. Med. Chem. Letters (2011) 21 528-530, starting from 2-(4-bromo-2-thienyl)-1,3-dioxolane) and 2,6-difluorobenzoyl chloride. Purification was performed using preparative HPLC to afford the title compound (17 mg, 18%). Data: LCMS (B) $R_t$: 11.185 min; m/z 480.8/482.8/484.8 [M−H+HCOOH]⁻ (bromide/chloride pattern).

Example 116

1-(2,6-Difluorobenzoyl)-2-(5-fluoro-4-iodo-2-thienyl)-3-hydroxy-imidazolidin-4-one This compound was prepared in an analogous manner as described for Example 109d and Example 2b starting from 5-fluoro-4-iodo-thiophene-2-carbaldehyde (prepared according to Badland et al, Bioorg. Med. Chem. Letters (2011) 21 528-530, starting from 2-(4-bromo-2-thienyl)-1,3-dioxolane) and 2,6-difluorobenzoyl chloride. Purification was performed, using preparative HPLC to afford the title compound (17 mg, 36%). Data: LCMS (B) $R_t$: 10.508 min; m/z 512.9 [M−H+HCOOH]⁻.

Example 117

4-[2-(4-Bromo-2-thienyl)-3-hydroxy-4-oxo-imidazolidine-1-carbonyl]-3,5-difluoro-benzonitrile This compound was prepared in an analogous manner as described for Example 1 and Example 38a starting from 2-(4-bromo-2-thienyl)-3-hydroxy-imidazolidin-4-one (Intermediate 2) and 4-cyano-2,6-difluoro-benzoic acid (prepared according to procedures described in WO 2012160464). Purification was performed using preparative HPLC to afford the title compound (7 mg, 16%). Data: LCMS (B) $R_t$: 9.657 min; m/z 471.9/473.9 [M−H+HCOOH]⁻ (bromide pattern).

Example 118a and Example 118b 2-(4-Bromo-2-thienyl)-3-hydroxy-1-[(1S)-1-phenylethyl]imidazolidin-4-one This compound was prepared in an analogous manner as described for Intermediate 2, starting from Intermediate 32 and 4-bromothiophene-2-carbaldehyde to afford the title compound as a mixture of two diastereomers.

The mixture of the two diastereomers was separated by preparative HPLC to afford the two separate diastereomers (diastereomer 1, first eluting from the column, less active isomer, and diastereomer 2, last eluting, most active isomer). LCMS showed for both diastereomers >95% de. Example 118a, isomer 1, 5 mg, 6%). Data: LCMS (B) $R_t$: 12.734 min; m/z 367.0/369.0 [M+H]⁺ (bromide pattern). Example 118b, isomer 2, 13.4 mg, 17%). Data: LCMS (B) $R_t$: 13.185 min; m/z 367.0/369.0 [M+H]$^+$ (bromide pattern).

Example 119a and Example 119b 2-(4-Iodo-2-thienyl)-3-hydroxy-1-[(1S)-1-phenyl-ethyl]imidazolidin-4-one This compound was prepared in an analogous manner as described for Intermediate 2, starting from Intermediate 32 and 4-iodothiophene-2-carbaldehyde (prepared according to Bad land et al, Bioorg. Med. Chem. Letters (2011) 21 528-530, starting from 2-(4-Bromo-2-thienyl)-1,3-dioxolane) to afford the title compound as a mixture of two diastereomers.

The mixture of the two diastereomers was separated by preparative HPLC to afford the two separate diastereomers (diastereomer 1, first eluting from the column, less active isomer, and diastereomer 2, last eluting, most active isomer). LCMS showed for both diastereomers >95% de. Example 119a, isomer 1, 7.4 mg, 8%). Data: LCMS (B) $R_t$: 13.126 min; m/z 415.0 [M+H]$^+$. Example 119b, isomer 2, 18.3 mg, 20%). Data: LCMS (B) $R_t$: 13.562 min; m/z 415.0 [M+H]$^+$.

Example 120a and Example 120b 2-(5-Bromo-2-thienyl)-3-hydroxy-1-[(1S)-1-phenyl-ethyl]imidazolidin-4-one This compound was prepared in an analogous manner as described for Intermediate 2, starting from Intermediate 32 and 5-bromothiophene-2-carbaldehyde to afford the title compound as a mixture of two diastereomers.

The mixture of the two diastereomers was separated by preparative HPLC to afford the two separate diastereomers (diastereomer 1, first eluting from the column, less active isomer, and diastereomer 2, last eluting, most active isomer). LCMS showed for both diastereomers >95% de. Example 120a, isomer 1, 6.5 mg, 8%). Data: LCMS (B) $R_t$: 12.999 min; m/z 367.0/369.0 [M+H]$^+$ (bromide pattern). Example 120b, isomer 2, 8.8 mg, 11%). Data: LCMS (B) $R_t$: 13.457 min; m/z 367.0/369.0 [M+H]$^+$ (bromide pattern).

Example 121a and Example 121b 2-(5-Bromo-3-thienyl)-3-hydroxy-1-[(1S)-1-phenyl-ethyl]imidazolidin-4-one This compound was prepared in an analogous manner as described for Intermediate 2, starting from Intermediate 32 and 5-bromothiophene-3-carbaldehyde to afford the title compound as a mixture of two diastereomers.

The mixture of the two diastereomers was separated by preparative HPLC to afford the two separate diastereomers (diastereomer 1, first eluting from the column, less active isomer, and diastereomer 2, last eluting, most active isomer). LCMS showed for both diastereomers >95% de. Example 121a, isomer 1, 7.3 mg, 9%). Data: LCMS (B) $R_t$: 12.579 min; m/z 367.0/369.0 [M+H]$^+$ (bromide pattern). Example 121b, isomer 2, 13.9 mg, 17%). Data: LCMS (B) $R_t$: 13.095 min; m/z 367.0/369.0 [M+H]$^+$ (bromide pattern).

Example 122

2-(4-Bromo-2-thienyl)-1-(2,6-difluoro-3-phenyl-benzoyl)-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-3-phenyl-benzoic acid (Intermediate 33). Purification was performed using preparative HPLC to afford the title compound (16 mg, 33%). Data: LCMS (B) $R_t$: 12.409 min; m/z 522.9/524.9 [M−H+HCOOH]$^-$ (bromide pattern).

Example 123

2-(5-Bromo-3-thienyl)-1-(2,6-difluoro-3-phenyl-benzoyl)-3-hydroxy-imidazolidin-4-one This compound was prepared in an analogous manner as described for Example 1 and Example 38a starting from 2-(5-bromo-3-thienyl)-3-hydroxy-imidazolidin-4-one (Intermediate 28) and 2,6-difluoro-3-phenyl-benzoic acid (Intermediate 33). Purification was performed using preparative HPLC to afford the title compound (5 mg, 10%). Data: LCMS (B) $R_t$: 12.282 min; m/z 522.9/524.9 [M−H+HCOOH]$^-$ (bromide pattern).

Example 124

2-(5-Bromo-3-thienyl)-1-[2,6-difluoro-3-(1-methylpyrazol-4-yl)benzoyl]-3-hydroxy-imidazolidin-4-one This compound was prepared in an analogous manner as described for Example 1 and Example 38a starting from 2-(5-bromo-3-thienyl)-3-hydroxy-imidazolidin-4-one (Intermediate 28) and 2,6-difluoro-3-(1-methylpyrazol-4-yl)benzoic acid (Intermediate 34). Purification was performed using preparative HPLC to afford the title compound (1.9 mg, 4%). Data: LCMS (B) $R_t$: 9.012 min; m/z 482.9/484.9 [M+H]$^+$ (bromide pattern).

Example 125

2-(4-Bromo-2-thienyl)-1-[2,6-difluoro-3-(1-methylpyrazol-4-yl)benzoyl]-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-3-(1-methylpyrazol-4-yl)benzoic acid (Intermediate 34). Purification was performed using preparative HPLC to afford the title compound (17 mg, 35%). Data: LCMS (B) $R_t$: 9.242 min; m/z 482.9/484.9 [M+H]$^+$ (bromide pattern).

Example 126

[3-[2-(4-Bromo-2-thienyl)-3-hydroxy-4-oxo-imidazolidine-1-carbonyl]-2,4-difluoro-phenyl]boronic acid This compound was prepared in an analogous manner as described for Example 1 and Example 38a starting from 2-(4-bromo-2-thienyl)-3-hydroxy-imidazolidin-4-one (Intermediate 2) and 3-carboxy-2,4-difluorophenylboronic acid. Purification was performed using preparative HPLC to afford the title compound (3 mg, 7%). Data: LCMS (B) $R_t$: 7.588 min; m/z 490.9/492.9 [M−H+HCOOH]$^-$ (bromide pattern).

Example 127

2-(4-Bromo-2-thienyl)-1-(3-ethynyl-2,6-difluoro-benzoyl)-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 3-ethynyl-2,6-difluoro-benzoic acid (Intermediate 35). Purification was performed using preparative HPLC to afford the title compound (6 mg, 14%). Data: LCMS (B) $R_t$: 10.488 min; m/z 470.9/472.9 [M–H+HCOOH]$^-$ (bromide pattern).

Example 128

2-(4-Bromo-2-thienyl)-1-(2,6-difluoro-3-vinyl-benzoyl)-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-3-vinyl-benzoic acid (Intermediate 36). Purification was performed using preparative HPLC to afford the title compound (5 mg, 12%). Data: LCMS (B) $R_t$: 10.921 min; m/z 472.9/474.9 [M–H+HCOOH]$^-$ (bromide pattern).

Example 129

2-(5-Bromo-3-thienyl)-1-[2,6-difluoro-3-[3-(sulfamoylamino)prop-1-ynyl] benzoyl]-3-hydroxy-4-oxo-imidazolidine This compound was prepared in an analogous manner as described for Example 1 and Example 38a starting from 2-(4-bromo-2-thienyl)-3-hydroxy-imidazolidin-4-one (Intermediate 2) and 3-[3-(tert-butoxycarbonylsulfamoylamino)prop-1-ynyl]-2,6-difluoro-benzoic acid (Intermediate 37). Purification was performed, after Boc-deprotection, using preparative HPLC to afford the title compound (9 mg, 56%). Data: LCMS (B) $R_t$: 8.428 min; m/z 532.9/534.9 [M–H]$^-$ (bromide pattern).

Example 130

N-[3-[4-[2-(4-Bromo-2-thienyl)-3-hydroxy-4-oxo-imidazolidine-1-carbonyl]-3,5-difluoro-phenyl]prop-2-ynyl]acetamide This compound was prepared starting from 1-[4-(3-aminoprop-1-ynyl)-2,6-difluoro-benzoyl]-2-(4-bromo-2-thienyl)-3-hydroxy-imidazolidin-4-one (Example 79) and acetylchloride. Purification was performed using preparative HPLC to afford the title compound (7 mg, 35%). Data: LCMS (B) $R_t$: 8.914 min; m/z 541.9/543.9 [M+HCOOH—H]$^-$ (bromide pattern).

Example 131

2-(4-Bromo-2-thienyl)-1-[2,6-difluoro-3-(2-thienyl)benzoyl]-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-3-(2-thienyl)benzoic acid (Intermediate 38). Purification was performed using preparative HPLC to afford the title compound (13 mg, 27%). Data: LCMS (B) $R_t$: 12.298 min; m/z 528.9/530.9 [M+HCOOH—H]$^-$ (bromide pattern).

Example 132

2-(4-Bromo-2-thienyl)-1-[2,6-difluoro-3-(5-fluoro-2-thienyl)benzoyl]-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-3-(5-fluoro-2-thienyl)benzoic acid (Intermediate 39). Purification was performed using preparative HPLC to afford the title compound (3 mg, 6%). Data: LCMS (B) $R_t$: 12.915 min; m/z 546.9/548.9 [M+HCOOH—H]$^-$ (bromide pattern).

Example 133

2-(4-Bromo-2-thienyl)-1-[2,6-difluoro-3-(o-tolyl)benzoyl]-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-3-(o-tolyl)benzoic acid (Intermediate 40). Purification was performed using preparative HPLC to afford the title compound (15 mg, 30%). Data: LCMS (B) $R_t$: 13.067 min; m/z 536.9/538.9 [M+HCOOH—H]$^-$ (bromide pattern).

Example 134

2-(4-Bromo-2-thienyl)-1-[2,6-difluoro-3-(1-naphthyl)benzoyl]-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-3-(1-naphthyl)benzoic acid (Intermediate 41). Purification was performed using preparative HPLC to afford the title compound (15 mg, 30%). Data: LCMS (B) $R_t$: 14.161 min; m/z 572.9/595.0 [M+HCOOH—H]$^-$ (bromide pattern).

Example 135

2-(4-Bromo-2-thienyl)-1-[2,6-difluoro-3-(2-naphthyl)benzoyl]-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-3-(2-naphthyl)benzoic acid (Intermediate 42). Purification was performed using preparative HPLC to afford the title compound (16 mg, 30%). Data: LCMS (B) $R_t$: 13.826 min; m/z 573.0/574.9 [M+HCOOH—H]$^-$ (bromide pattern).

Example 136

2-(4-Bromo-2-thienyl)-1-[2,6-difluoro-3-(4-fluorophenyl)benzoyl]-3-hydroxy-imidazolidin-4-one This compound was prepared in an analogous manner as described for Example 1 and Example 38a starting from 2-(4-bromo-2-thienyl)-3-hydroxy-imidazolidin-4-one (Intermediate 2) and 2,6-difluoro-3-(4-fluorophenyl)benzoic acid (Intermediate 43). Purification was performed using preparative HPLC to afford the title compound (13 mg, 26%). Data: LCMS (B) $R_t$: 12.681 min; m/z 540.9/542.9 [M+HCOOH—H]$^-$ (bromide pattern).

Example 137

Biochemical IDO1 Assay

To determine the inhibitory activity of compounds on IDO1, the NFK GreenScreen™ assay was used, which makes use of a chemical probe to detect NFK (Seegers, N., et al., J. Biol. Screen. 19: 1266; 2014). Compounds were serially diluted in dimethylsulfoxide (DMSO) and finally in IDO1 reaction buffer, consisting of 50 mM $NaH_2PO_4$, pH7.0, supplemented with 0.05% Tween-20 (cat. No. P7949; Sigma Aldrich) and 1% glycerol. Recombinant full-length IDO1 (Seegers, N., et al.) and all other assay components were diluted in IDO1 reaction buffer. 10 µl of compound solution, 20 µl of enzyme solution supplemented with 20 mM ascorbic acid, 20 µg/ml catalase, and 20 µM methylene blue were combined in the well of a black 384-well plate (cat. no. 3573; Corning, Corning, N.Y., USA) and incubated for 30 min at room temperature. Subsequently, 10 µl of 0.4 mM of the substrate L-tryptophan was added, i.e., the final concentration of L-tryptophan was 100 µM. The DMSO concentration in the assay was 0.3%. The concentration of IDO1 was 25 nM. Incubation was continued for 60 min at room temperature. Then, 10 µl of NFK Green™ (NTRC, Oss, The Netherlands) was added, the plate was sealed, and the reaction was developed for 3 hours at 37° C. To determine the production of N-formyl kynurenine (NFK), the seal was removed and fluorescence was read on an EnVision multimode reader (Perkin Elmer, Waltham, Mass., USA). $IC_{50}$ were calculated using XLfit™ software (ID Business Solutions, Ltd., Surrey, U.K.). The $IC_{50}$ of 1-MT in this assay is >100 µM. The $IC_{50}$ values of all exemplified compounds were found to be smaller than 25 µM. Compounds of examples 3, 10, 11, 12, 13, 14, 16, 18, 22, 23, 29, 30, 31, 35, 45a, 46a, 49a, 53, 54, 56, 64, 67, 68, 71, 92, 95, 97, 100, 108, 109 and 126 showed an $IC_{50}$ value >1 µM and <5 µM and compounds of examples 1, 2, 4, 7, 8, 9, 20, 21, 28, 33, 36, 37, 38, 39, 40, 41, 42, 43, 44, 45b, 46b, 47a, 47b, 48a, 48b, 49b, 50, 51, 52, 55, 63, 65, 66, 69, 73, 74, 75, 76-91, 93, 94, 96, 98, 99, 101-107, 111-117, 118b, 119b, 120b, 121b, 122, 123, 124, 125, 127, 128 and 129-136 showed an $IC_{50}$ of <1 µM.

Example 138

Cell-Based Assay for IDO1

A-375 melanoma cells were purchased from LGC Standards GmbH (Wesel, Germany) and cultured in DMEM tissue culture medium (Life Technologies, Bleiswijk, The Netherlands), supplemented with 10% (v/v) bovine calf serum. Compounds were dissolved in DMSO and diluted in DMEM. Final DMSO concentration in the assay was 0.4% (v/v). Eight thousand cells per well in 35 µl were seeded in a black 384-well tissue plate (cat. No. 781086; Greiner Bio-One GmbH, Frickenhausen, Germany) and allowed to adhere by incubation at 37° C., 95% humidity, and 5% CO2 overnight. Then, 5 µl of compound solution was added to the cells 1 hour prior to stimulation with 5 µl of 500 ng/ml interferon-γ (R&D Systems, Minneapolis, Minn., USA) diluted in DMEM medium. At the same time, 5 µl of L-tryptophan in 20 mM Hepes buffer pH 7.4 was added. Incubation was continued for 48 hours. To determine NFK levels, 12 µl NFK Green™ (NTRC, Oss, The Netherlands) was added to each well, and the plate was sealed and incubated for 4 hours at 37° C. Fluorescence was measured on an EnVision multimode reader (Perkin Elmer, Waltham, Mass., USA). $IC_{50}$ were calculated using XLfit™ software (ID Business Solutions, Ltd., Surrey, U.K.). Compounds of examples 1, 2, 4, 7, 8, 9, 11, 12, 20, 28, 33, 35-44, 45b, 46a, 46b, 47b, 48a, 48b, 49a, 49b, 50-52, 55, 63-66, 68, 69, 71, 73-78, 80-89, 94, 95, 97-106, 109, 110a, 110b, 111-117, 118b, 119b, 120b, 121b, 122-125, 127, 128 and 130-136 showed an $IC_{50}$ value of <5 µM Example 139

Biochemical Assay for TDO

The NFK GreenScreen™ assay was also used to determine the inhibitory activity of compounds on TDO (Seegers, N., et al., J. Biol. Screen. 19: 1266; 2014). Compounds were serially diluted in DMSO and finally in TDO reaction buffer, consisting of 100 mM $NaH_2PO_4$, pH 7.0, supplemented with 0.01% Tween-20 (cat. No. P7949; Sigma Aldrich). Recombinant TDO (Seegers, N., et al.) and all other assay components were diluted in TDO reaction buffer. 10 µl of compound solution and 20 µl of enzyme solution supplemented with 200 µM ascorbic acid were combined in the well of a black 384-well plate (cat. no. 3573; Corning, Corning, N.Y., USA), and incubated for 60 min at room temperature. Subsequently, 10 µl of 0.8 mM of the substrate L-tryptophan was added, i.e., the final concentration of L-tryptophan was 200 µM. The DMSO concentration in the assay was 0.3%. The concentration of TDO was 50 nM. Incubation was continued for 15 min at room temperature. Then, 10 µl of NFK Green™ (NTRC, Oss, The Netherlands) was added and the reaction was developed as described in Example 138 for the IDO1 assay. Fluorescence was read and $IC_{50}$ were calculated also as described above for IDO1. The $IC_{50}$ values of all exemplified compounds were found to be higher than 25 µM.

Example 140

Cytochrome P450 Assays

To determine the inhibitory potency of compounds on CYP3A4 enzyme, the P450-Glo CYP3A4 luciferin isopropylacetal (Luc-IP) assay was used (Promega, Madison, Wis., USA, Cat. No. V9920). The assay makes use of a luminogenic isopropylacetal (IPA) substrate that is a derivative from beetle luciferin, a substrate of luciferase enzymes. The IPA substrate is converted by CYP3A4 to luciferin, which in turn reacts with luciferase to produce an amount of light that is directly proportional to the activity of CYP3A4. Compounds were serially diluted in DMSO and finally in 400 mM $K_2HPO_4$, pH 7.4. 5 µl of compound solution and 5 µl of CYP3A4/substrate solution were combined in the well of a white 384-well Optiplate (Perkin Elmer). The DMSO concentration in the assay was 0.1%. After incubation for 10 minutes at room temperature in the dark, 10 µl of NADPH regeneration system was added and incubation was continued for 10 min. Then, 20 µl of Luciferin Detection Reagent was added to stop the reaction, and incubation was continued for another 20 min. Luminescence was measured on an Envision multimode reader and $IC_{50}$ values were calculated using XLfit™. Concentrations of enzyme, substrate and other reagents were set according to the instructions of the manufacturer (Promega document TB325, revision 3/15).

Instead of in a 96-well plate, the assay was performed in 384-well white Perkin Elmer Optiplate (cat. no. 6007290).

A similar assay was used to determine the inhibitory potency of compounds on CYP2D6. The P450-Glo CYP2D6 Luc-IP assay (Promega; Cat. No. V9890) makes use of a luminogenic substrate (ME EGE) that is converted to luciferin by CYP2D6. This assay was performed according to the instruction of the manufacturer (Promega document TB325, revision 3/15), with the difference that it was performed in a 384-well white Perkin Elmer Optiplates (cat. no. 6007290), instead of a 96-well plate. All volumes mentioned in the manufacturer's instruction were divided by a factor 2.5. The DMSO concentration during the incubation phase of the assay was 0.1%. The $IC_{50}$ values of all exemplified compounds were found to be higher than 10 µM in both assays.

The invention claimed is:

1. A compound of Formula I:

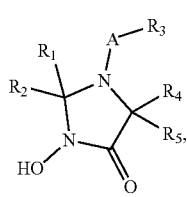

Formula I or a pharmaceutically acceptable salt thereof wherein,
$R^1$ is selected from the group consisting of:

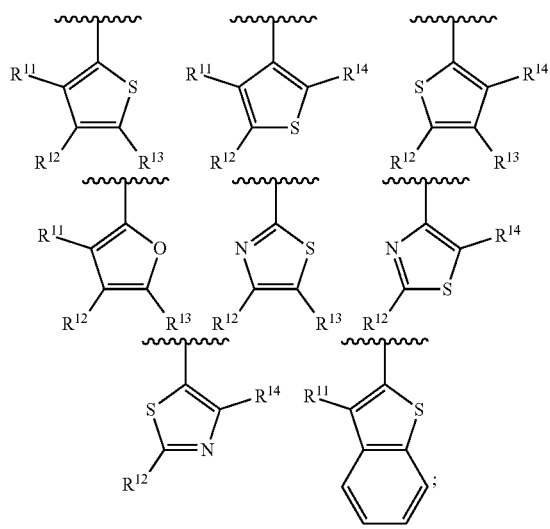

wherein $R^{11}$ is H, halogen, (1-2C)alkyl or (1-2C)alkoxy, all alkyl and alkoxy groups optionally being substituted with one or more halogen;

$R^{12}$ is halogen, (1-2C)alkyl, (2-3C)alkynyl, (1-2C)alkylthio, (3-8C)cycloalkyl, cyano or nitro, all alkyl and cycloalkyl groups optionally being substituted with one or more halogen;

$R^{13}$ is H, halogen, (1-2C)alkyl, (1-2C)alkoxy, deuterium or $C^2H_3$ (trideuteriomethyl), all alkyl and alkoxy groups optionally being substituted with one or more halogen;

$R_{14}$ is H, halogen, (1-2C)alkyl or (1-2C)alkoxy, all alkyl and alkoxy groups optionally being substituted with one or more halogen;

$R^2$ is selected from the group consisting of:
 a) hydrogen, and
 b) (1-6C)alkyl,
wherein (1-6C)alkyl optionally can be substituted, $R^3$ is selected from the group consisting of:
 a) (6-10C)aryl,
 b) (1-9C)heteroaryl,
 c) (3-8C)cycloalkyl,
 d) (2-7C)heterocycloalkyl, and
 e) (1-6C)alkyl,
wherein all groups optionally can be substituted, $R^4$ is selected from the group consisting of:
 a) hydrogen, and
 b) (1-6C)alkyl,
wherein (1-6C)alkyl optionally can be substituted, $R^5$ is selected from the group consisting of:
 a) hydrogen, and
 b) (1-6C)alkyl,
wherein (1-6C)alkyl optionally can be substituted, A is selected from the group consisting of $CH(R^a)$ and $C(O)$, and $R_a$ is selected from the group consisting of:
 a) hydrogen, and
 b) (1-6C)alkyl,
wherein (1-6C)alkyl optionally can be substituted with fluorine or hydroxyl.

2. The compound according to claim 1 wherein $R^2$ is hydrogen, and A is C(O) or $CH(R^a)$.

3. The compound according to claim 1, wherein $R^4$ and $R^5$ are hydrogen.

4. The compound according to claim 1, wherein $R^1$ is selected from the group consisting of:

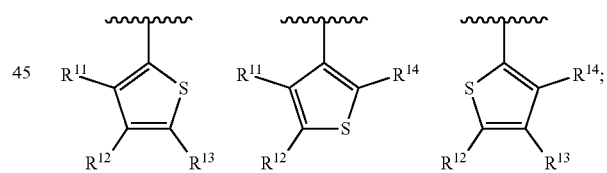

wherein $R^{11}$ is H, halogen, (1-2C)alkyl or (1-2C)alkoxy, all alkyl and alkoxy groups optionally being substituted with one or more halogen;

$R^{12}$ is halogen, (1-2C)alkyl, (2-3C)alkynyl, (1-2C)alkylthio, (3-8C)cycloalkyl, cyano or nitro, all alkyl and cycloalkyl groups optionally being substituted with one or more halogen;

$R^{13}$ is H, halogen, (1-2C)alkyl, (1-2C)alkoxy, deuterium or $C^2H_3$ (trideuteriomethyl), all alkyl and alkoxy groups optionally being substituted with one or more halogen; and $R^{14}$ is H, halogen, (1-2C)alkyl or (1-2C)alkoxy, all alkyl and alkoxy groups optionally being substituted with one or more halogen.

5. The compound according to claim 1, wherein $R^1$ is selected from the group consisting of:

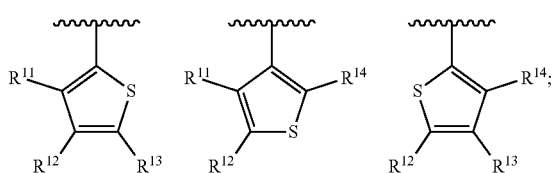

wherein $R^{11}$, $R^{14}$ is H,
$R^{12}$ is chlorine, bromine, iodine, nitro, (1-2C)alkyl, or (2-3C)alkynyl, all alkyl groups optionally being substituted with one or more halogen, and
$R^{13}$ is H, deuterium, $C^2H_3$ (trideuteriomethyl) or halogen.

6. The compound according to claim 1, 5 wherein $R^3$ is selected from the group consisting of (6-10C)aryl, (1-9C)heteroaryl, (3-8C)cycloalkyl, (2-7C)heterocycloalkyl, and (1-6C)alkyl, wherein all groups optionally can be substituted.

7. The compound according to claim 1, wherein $R^3$ is

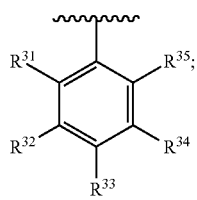

wherein $R^{31}$ and $R^{35}$ are independently selected from the group consisting of:
hydrogen, halogen, cyano, (1-6C)alkyl, (2-3C)alkenyl, (2-3C)alkynyl and (1-2C),alkoxy, all allkyl and alkoxy groups optionally being substituted with one or more halogen;
$R^{32}$ and $R^{34}$ are independently selected from the group consisting of:
hydrogen, halogen, nitro, B(OH)$_2$, cyano, (1-6C)alkyl, (2-6C)alkenyl, (2-6C)alkynyl, (1-2C)alkoxy, (3-8C)cycloalkyl, (2-7C)heterocycloalkyl, (6-10C)aryl or (1-9C)heteroaryl, aminosulfonylamino(2-6C)alkynyl, (1-6C)alkylsylfonylamino(2-6C)alkynyl, and (1-6C)carbonylamino(1-6C)alkynyl, each alkyl, alkenyl, alkynyl, alkoxy, cycloalkyl, heterocycloalkyl, aryl or heteroaryl optionally being substituted with one or more halogen, (1-3C)alkyl, (1-3C)alkoxy or cyano, $OR^{321}$, $N(R^{322},R^{323})$, $C(O)R^{324}$, $CH(R^b)N(R^{322},R^{323})$;
$R^{321}$ is selected from the group consisting of: hydrogen, (1-6C)alkyl, (1-4C)alkoxyl[(2-4C)alkoxy]$_m$(1-6C)alkyl, (3-8C)cycloalkyl, (2-7C)heterocycloalkyl, (6-10C)aryl, (1-9C)heteroaryl), (2-7C)heterocycloalkyl(1-6C)alky, (3-8C)cycloalkyl(1-6C)alkylsulfonyl, and heterocycloalkyl groups optionally substituted with one or more halogen, one or more (1-3C)alkyl;
m is 0-4;
$R^{322}$ and $R^{323}$ are independently selected from the group consisting of:
hydrogen, (1-6C)alkyl, (1-6C)alkylcarbonyl, (1-6C)alkylsulfonyl, and aminosulfonyl, all alkyl groups optionally substituted with one or more halogen;
$R^{324}$ is selected from the group consisting of: (1-6C)alkyl, (1-6C)alkylamino, (1-6C)alkoxy(1-6C)alkylamino, (6-10C)arylamino, (1-9C)heteroarylamino, and (2-7C)heterocycloalkylamino;
$R^b$ is selected from the group consisting of: hydrogen and (1-6C)alkyl; and $R^{33}$ is selected from the group consisting of:
hydrogen, halogen, cyano, (1-6C)alkyl, (2-3C)alkenyl, (2-6C)alkynyl, (1-3C)alkoxy, (6-10C)aryl, (1-5C)heteroaryl, (2-7C)heterocycloalkyl, (3-8C)cycloalkyl, (6-10C)aryloxy, (1-6C)alkylsulfonylamino(1-6C)alkyl, aminosulfonylamino(1-6C)alkyl, (3-8C)cycloalkyl(1-6C)alkyl, (1-6C)alkylcarbonylamino(2-6C)alkynyl, amino(2-6C)alkynyl, aminosulfonylamino(2-6C)alkynyl, (3-8C)cycloalkyl(2-3C)alkynyl, (1-6C)alkylsulfonylamino(2-6C)alkynyl, (1-3C)alkyl(2-3C)alkenyl, (6-10C)aryl(1-6C)alkyl, (1-3C)alkylsulfonyl(6-10C)aryl, and di[(1-6C)alkyl]amino, all alkyl and alkoxy groups optionally being substituted with one or more halogen, all (1-5C)heteroaryl groups optionally being substituted with one or more halogen, one or more (1-6C)alkyl.

8. The compound according to claim 1, wherein $R^3$ is

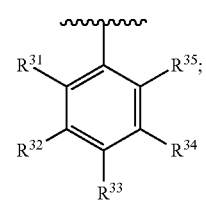

$R^{31}$ and $R^{35}$ are independently selected from the group consisting of: hydrogen, fluoro and chloro;
$R^{32}$ and $R^{34}$ are independently selected from the group consisting of:
hydrogen, halogen, nitro, B(OH)$_2$, cyano, (1-6C)alkyl, (2-6C)alkenyl, (2-6C)alkynyl, (1-2C)alkoxy, (3-8C)cycloalkyl, (2-7C)heterocycloalkyl, (6-10C)aryl or (1-9C)heteroaryl, aminosulfonylamino(2-6C)alkynyl, (1-6C)alkylsylfonylamino(2-6C)alkynyl, and (1-6C)carbonylamino(1-6C)alkynyl, each alkyl, alkenyl, alkynyl, alkoxy, cycloalkyl, heterocycloalkyl, aryl or heteroaryl optionally being substituted with one or more halogen, (1-3C)alkyl, (1-3C)alkoxy or cyano, $OR^{321}$, $N(R^{322},R^{323})$, $C(O)R^{324}$, $CH(R^b)N(R^{322},R^{323})$;
$R^{321}$ is selected from the group consisting of: hydrogen, (1-6C)alkyl, (1-4C)alkoxyl[(2-4C)alkoxy]$_m$(1-6C)alkyl, (3-8C)cycloalkyl, (2-7C)heterocycloalkyl, (6-10C)aryl, (1-9C)heteroaryl), (2-7C)heterocycloalkyl(1-6C)alkyl, and (3-8C)cycloalkyl(1-6C)alkyl, all alkyl, alkoxy, cycloalkyl, heterocycloalkyl groups optionally substituted with one or more halogen, one or more (1-3C)alkyl;
m is 0-4;
$R^{322}$ and $R^{323}$ are independently selected from the group consisting of:
hydrogen, (1-6C)alkyl, (1-6C)alkylcarbonyl, (1-6C)alkylsulfonyl, and aminosulfonyl, all alkyl groups optionally substituted with one or more halogen;
$R^{324}$ is selected from the group consisting of: (1-6C)alkyl, (1-6C)alkylamino, (1-6C)alkoxy(1-6C)alkylamino, (6-10C)arylamino, (1-9C)heteroarylamino, and (2-7C)heterocycloalkylamino;
$R^b$ is selected from the group consisting of: hydrogen and (1-6C)alkyl;
$R^{33}$ is selected from the group consisting of:
hydrogen, halogen, (1-6C)alkyl, (2-3C)alkenyl, (2-6C)alkynyl, (1-3C)alkoxy, (6-10C)aryl, (1-5C)heteroaryl, (3-8C)cycloalkyl, (1-6C)alkylsulfonylamino(1-6C)alkyl, aminosulfonylamino(1-6C)alkyl, (3-8C)cycloalkyl (1-6C)alkyl, amino(2-6C)alkynyl, aminosulfonylamino(2-6C)alkynyl, (3-8C)cycloalkyl(2-3C)alkynyl, (1-6C)alkylsulfonylamino(2-6C)alkynyl, (1-3C)alkoxy(1-6C)alkylaminocarbonyl, and di[(1-6C)alkyl]amino, all alkyl and alkoxy groups optionally being substituted with one or more halogen, all (1-5C)heteroaryl groups optionally being substituted with one or more halogen, one or more (1-6C)alkyl.

9. A method of inhibiting indoleamine 2.3-dioxygenase (IDO1) with the compound according to claim 1 or a pharmaceutically acceptable salt thereof.

10. A pharmaceutical composition comprising a compound of Formula I according to claim 1 or a pharmaceutically acceptable salt thereof and one or more pharmaceutically acceptable excipients.

11. The pharmaceutical composition according to claim 10, furthur comprising at least one additional therapeutically active agent.

12. The compound according to claim 1, a pharmaceutically acceptable salt thereof or a pharmaceutical composition comprising the compound according to claim 1, wherein the compound or salt thereof has an inhibitory potency on indoleamine 2,3-dioxygenase (IDO1) with an $IC_{50}$ of 25 µM or less.

13. The compound according to claim 1, wherein $R^2$ is hydrogen, and A is C(O) or CH($R^a$).

14. The compound according to claim 1, wherein $R^3$ is selected from the group consisting of (6-10C)aryl, (1-9C)heteroaryl and (3-8C)cycloalkyl, wherein all groups optionally can be substituted.

15. The compound according to claim 1, a pharmaceutically acceptable salt thereof or a pharmaceutical composition comprising the compound according to claim 1, wherein the compound or salt thereof has an inhibitory potency on indoleamine 2,3-dioxygenase (IDO1) with an $IC_{50}$ of 20 µM or less.

16. The compound according to claim 1, a pharmaceutically acceptable salt thereof or a pharmaceutical composition comprising the compound according to claim 1, wherein the compound or salt thereof has an inhibitory potency on indoleamine 2,3-dioxygenase (IDO1) with an $IC_{50}$ of 10 µM or less.

17. The compound according to claim 1, a pharmaceutically acceptable salt thereof or a pharmaceutical composition comprising the compound according to claim 1, wherein the compound or salt thereof has an inhibitory potency on indoleamine 2,3-dioxygenase (IDO1) with an $IC_{50}$ of 5 µM or less.

* * * * *